United States Patent
Rivera et al.

(10) Patent No.: US 12,263,156 B2
(45) Date of Patent: Apr. 1, 2025

(54) USE OF SMALL MOLECULE INHIBITORS OF THE BFRB:BFD INTERACTION IN BIOFILMS

(71) Applicants: Board of Supervisors of Louisiana State University and Agricultural and Mechanical College, Baton Rouge, LA (US); University of Kansas, Lawrence, KS (US); The Board of Regents for Oklahoma State University, Stillwater, OK (US)

(72) Inventors: Mario Rivera, Baton Rouge, LA (US); Huili Yao, Baton Rouge, LA (US); Richard A. Bunce, Stillwater, OK (US); Baskar Nammalwar, San Diego, CA (US); Krishna Kumar Gnanasekaran, Mississauga (CA); Kate Eshelman, Alexandria, VA (US); Achala N. D. Punchi Hewage, Lawrence, KS (US); Scott Lovell, Shawnee, KS (US); Anabel Soldano, Baton Rouge, LA (US)

(73) Assignees: Board of Supervisors of Louisiana State University and Agricultural and Mechanical College, Baton Rouge, LA (US); The Board of Regents for Oklahoma State University, Lawrence, KS (US); University of Kansas, Stillwater, OK (US)

( * ) Notice: Subject to any disclaimer, the term of this patent is extended or adjusted under 35 U.S.C. 154(b) by 581 days.

(21) Appl. No.: 17/502,975

(22) Filed: Oct. 15, 2021

(65) Prior Publication Data
US 2022/0117937 A1 Apr. 21, 2022

Related U.S. Application Data

(60) Provisional application No. 63/120,405, filed on Dec. 2, 2020, provisional application No. 63/092,571, filed on Oct. 16, 2020.

(51) Int. Cl.
*A61P 31/04* (2006.01)
*A61K 31/4035* (2006.01)

(52) U.S. Cl.
CPC .......... *A61K 31/4035* (2013.01); *A61P 31/04* (2018.01)

(58) Field of Classification Search
None
See application file for complete search history.

(56) References Cited

U.S. PATENT DOCUMENTS

2014/0296310 A1 10/2014 Alex et al.
2022/0031661 A1* 2/2022 Rivera .................. A61K 31/496

FOREIGN PATENT DOCUMENTS

WO WO-2017049409 A1 * 3/2017

OTHER PUBLICATIONS

Kaneko et al., "The Transition Metal Gallium Disrupts Pseudomonas aeruginosa Iron Metabolism and has Antimicrobial and Antibiofilm Activity", Journal of Clinical Investigation, (2007), vol. 117, No. 4, pp. 877-887. 10.1172/JCI30783.
Kang et al., "Interdependence between iron acquisition and biofilm formation in Pseudomonas aeruginosa", Journal of Microbiology, (2018), vol. 56, pp. 449-457. 10.1007/s12275-018-8114-3.
Keyer et al., "Superoxide Accelerates DNA-Damage by Elevating Free-Iron Levels", Proc. Natl. Acad Sci., (1996), vol. 93, pp. 13635-13649. DOI: doi.org/10.1073/pnas.93.24.13635.
Koenig et al., "Ventilator-Associated Pneumonia: Diagnosis, Treatment, and Prevention", Clin. Microbio. Rev., (2006), vol. 19, pp. 637-657.
Kolpen et al., "Increased bactericidal activity of colistin on Pseudomonas aeruginosa biofilms in anaerobic conditions", Pathogens and Disease, (2016), vol. 74, No. 1, 7 pages, ftv086. 10.1093/femspd/ftv086.
Konstan et al., "Risk factors for rate of decline in forced expiratory volume in one second in children and adolescents with cystic fibrosis", J Pediatr., (2007), vol. 151, pp. 134-139, 139 e1. 10.1016/j.jpeds.2007.03.006.

(Continued)

*Primary Examiner* — John S Kenyon
(74) *Attorney, Agent, or Firm* — Venable LLP; Keith G. Haddaway; Hemant Khanna

(57) ABSTRACT

The present invention discloses methods of inhibiting biofilm formation, increasing bacteriocidal activity within a biofilm, treating bacteria within a biofilm, or remediating a biofilm in or on a subject, comprising administering to the subject an effective amount of a compound according to Formula I:

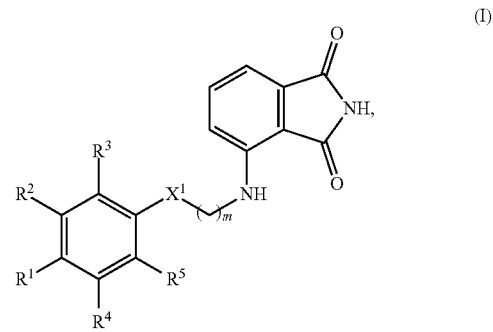

wherein $R^{1-5}$ are defined herein.

20 Claims, 13 Drawing Sheets
(9 of 13 Drawing Sheet(s) Filed in Color)
Specification includes a Sequence Listing.

(56) References Cited

OTHER PUBLICATIONS

Koulenti et al., "Spectrum of practice in the diagnosis of nosocomial pneumonia in patients requiring mechanical ventilation in European intensive care units", Crit. Care Med., (2009), vol. 37, pp. 2360-2368.
Lakemeyer et al., "Thinking Outside the Box-Novel Antibacterials To Tackle the Resistance Crisis", Angewandte Chemie Int. Ed Engl., (2018), vol. 57, No. 44, pp. 14440-14475. 10.1002/anie.201804971.
Lam et al., "Production of Mucold Microcolonies by Pseudomonas aeruginosa Within Infected Lungs in Cystic Fibrosis", Infect. Immun., (1980), vol. 28, pp. 546-556. PMCID PMC550970.
Lawrence et al., "Optical sectioning of microbial biofilms", J Bacterial., (1991), vol. 173, pp. 6558-6567. 10.1128/jb.173.20.6558-6567.1991.
Laxminarayan et al., "Antibiotic resistance-the need for global solutions", Lancet Infect. Dis., (2013), vol. 13, No. 12, pp. 1057-1098.
Li et al., "Colistin: the re-emerging antibiotic for multidrug-resistant Gram-negative bacterial infections", Lancet Infectious Diseases, (2006), vol. 6, No. 9, pp. 589-601. 10.1016/SI473-3099(06)70580-I.
Li, "Reviving Polymyxins: Achievements, Lessons and the Road Ahead. In Polymyxin Antibiotics: From Laboratory Bench to Bedside", Advances in Experimental Medicine and Biology, (2019), vol. 1145, pp. 1-8.
Liu et al., "A Synthetic Dual Drug Sideromycin Induces Gram-Negative Bacteria To Commit Suicide with a Gram-Positive Antibiotic", Journal of Medicinal Chemistry, (2018), vol. 61, No. 9, pp. 3845-3854. 10.1021/acs.jmedchem.8b00218.
Lora-Tamayo et al., "Clinical Use of Colistin in Biofilm-Associated Infections", Advances in Experimental Medicine and Biology, (2019), vol. 1145, pp. 181-195.
Ma et al., "Bacterioferritin A Modulates Catalase A (KatA) Activity and Resistance to Hydrogen Peroxide in Pseudomonas aeruginosa", J Bacterial., (1999), vol. 181, pp. 3730-3742.
Madeira et al., "The EMBL-EBI search and sequence analysis tools APIs in 2019", Nucleic Acids Research, (2019), vol. 47, No. W1, pp. W636-W641. 10.1093/nar/gkz268.
Marques et al., "Discrepancy between viable counts and light output as viability measurements, following ciprofloxacin challenge of self-bioluminescent Pseudomonas aeruginosa biofilms", Journal of Antimicrobial Chemotherapy, (2005), vol. 56, No. 4, pp. 665-671. 10.1093/jac/dki285.
Marques et al., "Pharmacodynamics of ciprofloxacin against Pseudomonas aeruginosa planktonic and biofilm-derived cells", Letters in Applied Microbiology, (2019), vol. 68, No. 4, pp. 350-359. 10.1111/lam.13126.
McCoy et al., "Phaser crystallographic software", J Appl. Cryst., (2007), vol. 40, pp. 658-674. 10.1107/S0021889807021206.
Mettrick et al., "The Iron-chelator, N,N'-bis (2-hydroxybenzyl) Ethylenediamine-N,N'-Diacetic acid is an Effective Colistin Adjunct against Clinical Strains of Biofilm-Dwelling Pseudomonas aeruginosa", Antibiotics, (2020), vol. 9, 14 pages. 10.3390/antibiotics9040144.
Minandri et al., "Promises and fallures of gallium as an antibacterial agent", Future Microbial., (2014), vol. 9, pp. 379-397. 10.2217/fmb.14.3.
Moreau-Marquis et al., "Tobramycin and FDA-approved iron chelators eliminate Pseudomonas aeruginosa biofilms on cystic fibrosis cells", American Journal of Respiratory Cell and Molecular Biology, (2009), vol. 41, No. 3, pp. 305-313. 10.1165/rcmb.2008-02990C.
Nation et al., "Colistin in the 21st century", Current Opinion in Infectious Disease, (2009), vol. 22, No. 6, pp. 535-543. 10.1097/QCO.0b013e328332e672.
O'Connor et al., "Chemical genetics", Chem Soc Rev., (2011), vol. 40, No. 8, pp. 4332-4345.
Oliver, "Recent findings on the viable but nonculturable state in pathogenic bacteria", FEMS Microbiology Reviews, (2010), vol. 34, No. 4, pp. 415-425. 10.1111/j.1574-6976.2009.00200.x.

O'May et al., "Iron-binding compounds impair Pseudomonas aeruginosa biofilm formation, especially under anaerobic conditions", Journal of Medical Microbiology, (2009), vol. 58, pp. 765-773. 10.1099/jmm.0.004416-0.
Otsu, "A Threshold Selection Method for Gray-Level Histograms", IEEE Transactions on Systems, Man, and Cybernetics, (1979), vol. 9, No. 1, pp. 62-66.
Pamp et al., "Tolerance to the antimicrobial peptide colistin in Pseudomonas aeruginosa biofilms is linked to metabolically active cells, and depends on the pmr and mexAB-oprM genes", Molecular Microbiology, (2008), vol. 68, No. 1, pp. 223-240. 10.1111/j.1365-2958.2008.06152.x.
Parsek et al., "Bacterial biofilms: an emerging link to disease pathogenesis", Annual Review of Microbiology, (2003), vol. 57, pp. 677-701. 10.1146/annurev.micro.57.030502.090720.
Post et al., "Connecting iron acquisition and biofilm formation in the ESKAPE pathogens as a strategy for combatting antibiotic resistance", Medcherncomm, (2019), vol. 10, No. 4, pp. 505-512. 10.1039/c9md00032a.
Punchi et al., "Small Molecule Inhibitors of the BfrB-Bfd Interaction Decrease Pseudomonas aeruginosa Fitness and Potentiate Fluoroquinolone Activity", J Am. Chem. Soc., (2019), vol. 141, No. 20, pp. 8171-8184. 10.1021/jacs.9b00394.
Rivera, "Bacterioferritin: Structure Function and Protein-Protein Interactions", In Handbook of Porphyrin Science, (2014), vol. 30, pp. 136-179.
Rivera, "Bacterioferritin: Structure, Dynamics and Protein-Protein Interactions at Play in Iron Storage and Mobilization" Acc. Chem. Res., (2017), vol. 50, pp. 331-340. 10.1021/acs.accounts.6b00514.
Romling et al., "Biofilm infections, their resilience to therapy and innovative treatment strategies", Journal of Internal Medicine, (2012), vol. 272, No. 6, pp. 541-561. 10.1111/jolm.12004.
Rui et al., "Protein dynamics and ion traffic in bacterioferritin", Biochemistry (2012), vol. 51, No. 49, pp. 9900-9910.
Ruvinsky et al., "Local packing modulates diversity of iron pathways and cooperative behavior in eukaryotic and prokaryotic ferritins", J Chem. Phys., (2014), vol. 140, No. 11, 9 pages, 115104.
Sebaugh, "Guidelines for accurate EC50/IC50 estimation", Pharmaceutical Statistics, (2011), vol. 10, No. 2, pp. 128-134. 10.1002/pst.426.
Singh et al., "A Component of Innate Immunity Prevents Bacterial Biofilm Development", Nature, (2002), vol. 417, No. 6888, pp. 552-555. 10.1038/417552a.
Soldano et al., "Inhibiting Iron Mobilization from Bacterioferritin in Pseudomonas aeruginosa Impairs Biofilm Formation Irrespective of Environmental Iron Availability", ACS Infect. Dis., (2020), vol. 6, No. 3, pp. 447-458. 10.1021/acsinfecdis.9b00398.
Spring, "Chemical genetics to chemical genomics: small molecules offer big insights", Chem. Soc. Rev., (2005), vol. 34, No. 6, pp. 472-482.
Stewart et al., "Antibiotic resistance of bacteria in biofilms", Lancet, (2001), vol. 358, No. 9276, pp. 135-138. 10.1016/s0140-6736(01)05321-1.
Stover et al., "Complete Genome Sequence of Pseudomonas aeruginosa PA01, an Opportunistic Pathogen", Nature, (2000), vol. 406, pp. 959-964. 10.1038/35023079.
Sutherland, "Biofilm exopolysaccharides: a strong and sticky framework", Microbiology, (2001), vol. 147, pp. 3-9. 10.1099/00221287-147-1-3.
Tacconelli et al., "Discovery, research, and development of new antibiotics: the WHO priority list of antibiotic-resistant bacteria and tuberculosis", Lancet Infect. Dis., (2018), vol. 18, pp. 318-327. 10.1016/S1473-3099(17)30753-3.
Tawakoli et al., "Comparison of different live/dead stainings for detection and quantification of adherent microorganisms in the initial oral biofilm", Clinical Oral Investigations, (2013), vol. 17, No. 3, pp. 841-850. 10.1007/s00784-012-0792-3.
The Pharma Letter, "Healthcare-Associated Gram-Negative market to be worth $3.6 billion by 2026; report", Press Release, (Sep. 20, 2017); <https://www.globaldata.com/healthcare-associated-gram-negative-market-to-be-worth-3-6-billion-by-2026/>. screen shot of website.

(56) References Cited

OTHER PUBLICATIONS

Verderosa et al., "Bacterial Biofilm Eradication Agents: A Current Review", Frontiers in Chemistry, (2019), vol. 7, 17 pages. 10.3389/fchem.2019.00824.
Visca et al., "The dual personality of iron chelators: growth inhibitors or promoters?", Antimicrobial Agents and Chemotherapy, (2013), vol. 57, No. 5, pp. 2432-2433. 10.1128/AAC.02529-12.
Vonrhein et al., "Data Processing and Analysis with the autoPROC toolbox", Acta Cryst. D Biol Cryst., (2011), vol. D67, pp. 293-302. 10.1107/S0907444911007773.
Adams et al., "PHENIX: A Comprehensive Python-Based System for Macromolecular Structure Solution", Acta Cryst., (2010), vol. D66, pp. 213-221. 10.1107/S0907444909052925.
Anderl et al., "Role of nutrient limitation and stationary-phase existence in Klebsiella pneumoniae biofilm resistance to ampicillin and ciprofloxacin", Antimicrobial Agents and Chemotherapy, (2003), vol. 47, No. 4, pp. 1251-1256. 10.1128/aac.47.4.1251-1256.2003.
Andrews et al., "Control of iron metabolism in bacteria", Met. Ions Life Sci., (2013), vol. 12, pp. 203-239.
Andrews, "Determination of Minimum Inhibitory Concentrations", J Antimicrob. Chemother., (2001), vol. 48, Suppl. 1, pp. 5-16. 10.1093/jac/48.suppl_1.5.
Anwar et al., "Dynamic interactions of biofilms of mucoid Pseudomonas aeruginosa with tobramycin and piperacillin", Antimicrobial Agents and Chemotherapy, (1992), vol. 36, No. 6, pp. 1208-1214. 10.1128/aac.36.6.1208.
Anwar et al., "Enhanced activity of combination of tobramycin and piperacillin for eradication of sessile biofilm cells of Pseudomonas aeruginosa", Antimicrobial Agents and Chemotherapy, (1990), vol. 34, No. 9, pp. 1666-1671. 10.1128/aac.34.9.1666.
Ayrapetyan et al., "Bridging the gap between viable but non-culturable and antibiotic persistent bacteria", Trends in Microbiology, (2015), vol. 23, No. 1, pp. 7-13. 10.1016/j.tim.2014.09.004.
Ballouche et al., "Iron Metabolism: A Promising Target for Antibacterial strategies", Recent Patents on Anti-Infective Drug Discovery, (2009), vol. 4, pp. 190-205.
Banin et al., "Chelator-induced dispersal and killing of Pseudomonas aeruginosa cells in a biofilm", Applied Environmental Microbiology, (2006), vol. 72, No. 3, pp. 2064-2069. 10.1128/AEM.72.3.2064-2069.2006.
Banin et al., "Iron and Pseudomonas aeruginosa biofilm formation", Proc. Natl. Acad Sci., (2005), vol. 102, pp. 11076-11081. 10.1073/pnas.0504266102.
Benson et al., "Heme Uptake and Metabolism in Bacteria", Met. Ions Life Sci., (2013), vol. 12, pp. 279-332.
Blaskovich et al., "Polishing the tarnished silver bullet: the quest for new antibiotics", Essays Biochem., (2017), vol. 61, No. 1, pp. 103-114.
Boucher et al., "Bad Bugs, No. Drugs: No. ESKAPE! An Update from the Infectious Diseases Society of America", Clin. Infect. Dis., (2009), vol. 48, pp. 1-11. 10.1086/595011.
Brauner et al., "Distinguishing between resistance, tolerance and persistence to antibiotic treatment", Nature Reviews Microbiology, (2016), vol. 14, pp. 320-330. 10.1038/nrmicro.2016.34.
Bullen et al., "Iron and Infection: The Heart of the Matter", FEMS Immunol. Med Microbial., (2005), vol. 43, pp. 325-330. 10.1016/j.femsim.2004.11.010.
Burrows, "The Therapeutic Pipeline for Pseudomonas aeruginosa Infections", ACS Infect. Dis., (2018), vol. 4, pp. 1041-1047. 10.1021/acsinfecdis.8b00112.
CDC, "Antibiotic Resistance Threats in the United States", (2019), 150 pages. rwww.cdc.gov/drugresistance/threat-report-2019/ (Reference broken into two parts).
Centola et al., "Gallium(III)-Salophen as a Dual Inhibitor of Pseudomonas aeruginosa Heme Sensing and Iron Acquisition", ACS Infectious Diseases, (2020), vol. 6, No. 8, pp. 2073-2085. 10.1021/acsinfecdis.0c00138.
Ceri et al., "The Calgary Biofilm Device: new technology for rapid determination of antibiotic susceptibilities of bacterial biofilms", Journal of Clinical Microbiology, (1999), vol. 37, No. 6, pp. 1771-1776. 10.1128/JCM.37.6.1771-1776.1999.
Chellat et al. "Targeting Antibiotic Resistance", Angewandte Chemie Int. Ed Engl., (2016), vol. 55, pp. 6600-6026. 10.1002/anie.201506818.
Chen et al., "MolProbity: All-Atom Structure Validation for Macromolecular Crystallography", Acta Cryst., (2010), vol. D66, pp. 12-21. 10.1107/S0907444909042073.
Ciccone et al., "Multicomponent mixtures for cryoprotection and ligand solubilization", Biotechnology Reports, (2015), vol. 7, No. a1, pp. 120-127. 10.1016/j.btre.2015.05.008.
Clark et al., "DNA Replication and the Division Cycle in *Escherichia coli*", J Mol. Biol., (1967), vol. 23, pp. 99-112. 10.1016/S0022-2836(67)80070-6.
Cornelis et al., "Iron homeostasis and management of oxidative stress response in bacteria", Metallomics, (2011), vol. 3, No. 6, pp. 540-549.
Costerton et al., "Bacterial Biofilms: A Common Cause of Persistent Infection", Science, (1999), vol. 284, pp. 1318-1322. 10. 1 126/science.284.5418.1318.
Crabbe et al., "Antimicrobial Tolerance and Metabolic Adaptations in Microbial Biofilms", Trends in Microbiology, (2019), vol. 27, pp. 850-863. 10.1016/j.tim.2019.05.003.
Crull et al., "Change in Pseudomonas aeruginosa prevalence in cystic fibrosis adults over time", BMC Pulm Med., (2016), vol. 16, 7 pages. 10.1186/sl2890-016-0333-y.
Davies, "Understanding biofilm resistance to antibacterial agents", Nature Reviews Drug Discovery, (2003), vol. 2, No. 2, pp. 114-122. 10.1038/nrdl008.
Emsley et al., "Features and Development of Coot", Acta Cryst., (2010), vol. D66, pp. 486-501. 10.1107/S0907444910007493.
Eshelman et al., "Inhibiting the BfrB:Bfd Interaction in Pseudomonas aeruginosa Causes Irreversible Iron Accumulation in Bacterioferritin and Iron Deficiency in the Bacterial Cell", Metallomics, (2017), vol. 9, No. 6, pp. 646-659. DOI: 10.1039/C7MT00042A.
Evans, "An Introduction to Data Reduction: Space-Group Determination, scaling and intentisy statistics", Acta Cryst., (2011), vol. D67, pp. 282-292. 10.1107/S090744491003982X.
Ezadi et al., "Antimicrobial Susceptibility Testing for Polymyxins: Challenges, Issues, and Recommendations", Journal of Clinical Microbiology, (2019), vol. 57, No. 4, 21 pages. e01390-18 10.1128/JCM.01390-18.
Foley et al., "Targeting iron assimilation to develop new antibacterials", Expert Opin. Drug Discov., (2012), vol. 7, No. 9, pp. 831-847.
Friedman et al., "Genes involved in matrix formation in Pseudomonas aeruginosa PAI4 biofilms", Molecular Microbiology, (2004), vol. 51, No. 3, pp. 675-690. 10.1046/j. 1365-2958.2003.03877.x.
Frontline, "Hunting the Nightmare Bacteria", (2011), Frontline, PBS, Season 2, Television Episode 13.
Gnanasekaran et al., "4,7-Diaminoisoindoline-1,3-dione", Organic Preparations and Procedures International, (2018), vol. 50, No. 3, pp. 372-374. 10.1080/00304948.2018.1462072.
Goss et al., "Gallium disrupts bacterial iron metabolism and has therapeutic effects in mice and humans with lung infections", Sci. Transl. Med., (2018), vol. 10, No. 460, 29 pages. 10.1126/scitranslmed.aat7520.
Haagensen et al., "Differentiation and distribution of colistin- and sodium dodecyl sulfate-tolerant cells in Pseudomonas aeruginosa biofilms", J Bacterial., (2007), vol. 189, No. 1, pp. 28-37. 10.1128/JB.00720-06.
Harmsen et al., "An update on Pseudomonas aeruginosa biofilm formation, tolerance, and dispersal", FEMS Immunology and Medical Microbiology, (2010), vol. 59, No. 3, pp. 253-268. 10.1111/j.1574-695X.2010.00690.x.
Heinzl et al., "Iminoguanidines as Allosteric Inhibitors of the Iron-Regulated Heme Oxygenase (HemO) of Pseudomonas aeruginosa", J Med Chem., (2016), vol. 59, pp. 6929-6942. 10.1021/acs.jmedchem.6b00757.
Hennessy et al., "Ferene-a new spectrophotometric reagent for iron", Can. J Chem., (1984), vol. 62, pp. 721-724. 10.1139/v84-121.

(56) References Cited

OTHER PUBLICATIONS

Hentzer et al., "Attenuation of Pseudomonas aeruginosa virulence by quorum sensing inhibitors", EMBO Journal, (2003), vol. 22, No. 15, pp. 3803-3815. 10.1093/emboj/cdg366.
Heydorn et al., "Quantification of biofilm structures by the novel computer program COMSTAT", Microbiology, (2000), vol. 146, Pt. 10, pp. 2395-2407. 10.1099/00221287-146-10-2395.
Hoiby et al., "Antibiotic resistance of bacterial biofilms", International Journal of Antimicrobial Agents, (2010), vol. 35, No. 4, pp. 322-332. 10.1016/j.ijantimicag.2009.12.011 Dec. 16, 2021.
Hood et al., "Nutritional immunity: transition metals at the pathogen-host interface", Nat. Rev. Microbial., (2012), vol. 10, No. 8, pp. 525-537.
James et al., "Biofilms in chronic wounds", Wound Repair and Regeneration, (2008), vol. 16, pp. 37-44. 10.1111/j.1524-475X.2007.00321.x.
Ji et al., "Iron transport-mediated drug delivery: practical syntheses and in vitro antibacterial studies of tris-catecholate siderophore-aminopenicillin conjugates reveals selectively potent antipseudomonal activity", Journal of the American Chemical Society, (2012), vol. 134, No. 24, pp. 9898-9901. 10.1021/ja303446w.
Johnson et al., "Ncbi Blast: a better web interface", Nucleic Acids Research, (2008), vol. 36, pp. W5-9. 10.1093/nar/gkn201.
Kabsch, "Automatic Indexing of Rotation Diffraction Patterns", J Appl. Cryst., (1988), vol. 21, pp. 67-72. 10.1107/S002188988700937.
Kadam et al., "Recent Advances in Non- Conventional Antimicrobial Approaches for Chronic Wound Biofilms: Have We Found the 'Chink in the Armor'?", Biomedicines, (2019), vol. 7, 26 pages. 10.3390/biomedicines7020035.
Vrany et al., "Comparison of recalcitrance to ciprofloxacin and levofloxacin exhibited by Pseudomonas aeruginosa biofilms displaying rapid-transport characteristics", Antimicrobial Agents and Chemotherapy, (1997), vol. 41, No. 6, pp. 1352-1358. 10.1128/AAC.41.6.1352.
Walters et al., "Contributions of antibiotic penetration, oxygen limitation, and low metabolic activity to tolerance of Pseudomonas aeruginosa biofilms to ciprofloxacin and tobramycin", Antimicrobial Agents and Chemotherapy, (2003), vol. 47, No. 1, pp. 317-323. 10.1128/aac.47.1.317-323.2003.
Wang et al., "Characterization of the Bacterioferritin/Bacterioferritin Associated Ferredoxin Protein-Protein Interactions in Solution and Determination of Binding Energy Hot Spots", Biochemistry, (2015), vol. 54, pp. 6162-6175. 10.1021/acs.biochem.5b00937.
Weeratunga et al., "Binding of Pseudomonas aeruginosa Apobacterioferritin-Associated Ferredoxin to Bacterioferritin B Promotes Heme Mediation of Electron Delivery and Mobilization of Core Mineral Iron", Biochemistry, (2009), vol. 48, pp. 7420-7431. 10.1021/bi900561a.
Weeratunga et al., "Structural Studies of Bacterioferritin B (BfrB) from Pseudomonas aeruginosa Suggest a Gating Mechanism for Iron Uptake via the Ferroxidase Center", Biochemistry, (2010), vol. 49, pp. 1160-1175. 10.1021/bi9015204.
Weinberg, "Iron Availability and Infection", Biochim. et Biophys. Acta, (2009), vol. 1790, pp. 600-605. 10.1016/j.bbagen.2008.07.002.
Werner et al., "Stratified growth in Pseudomonas aeruginosa biofilms", Applied and Environmental Microbiology, (2004), vol. 70, No. 10, pp. 6188-6196. 10.1128/AEM.70.10.6188-6196.2004.
Wijerathne et al., "Bfd, a New Class of [2Fe—2S] Protein That Functions in Bacterial Iron Homeostasis, Requires a Structural Anion Binding Site", Biochemistry, (2018), vol. 57, pp. 5533-5543. 10.1021/acs.biochem.8b00823.
Windus et al., "Fatal Rhizopus Infections in Hemodialysis Patients Receiving Deferoxamine", Annals of Internal Medicine, (1987), vol. 107, No. 5, pp. 678-680. 10.7326/0003-4819-107-5-678.
Winsor et al., "Enhanced annotations and features for comparing thousands of Pseudomonas genomes in the Pseudomonas genome database", Nucleic Acids Research, (2016), vol. 44, pp. D646-D653. 10.1093/nar/gkv1227.
Xu et al. "Spatial physiological heterogeneity in Pseudomonas aeruginosa biofilm is determined by oxygen availability", Applied and Environmental Microbiology, (1998), vol. 64, No. 10, pp. 4035-4039. 10.1128/AEM.64.10.4035-4039.1998.
Yamamoto et al., "Trade-off between oxygen and iron acquisition in bacterial cells at the air-liquid interface", FEMS Microbiology Ecology, (2011), vol. 77, No. 1, pp. 83-94. 10.1111/j.1574-6941.2011.01087.x.
Yao et al., "Concerted motions networking pores and distant ferroxidase centers enable bacterioferritin function and iron traffic", Biochemistry (2015), vol. 54, No. 8, pp. 1611-1627.
Yao et al., "The Structure of the BfrB-Bfd Complex Reveals Protein-Protein Interactions Enabling Iron Release from Bacterioferritin", Journal of the American Chemical Society, (2012), vol. 134, pp. 13470-13481. 10.1021/ja305180n.
Yao et al., "Two Distinct Ferritin-Like Molecules in P. aeruginosa: The Product of the bfrA Gene is a Bacterial Ferritin (FtnA) not a bacterioferritin (Bfr)", Biochemistry, (2011), vol. 50, No. 23, pp. 5236-5248. 10.1021/bi2004119.
"Hunting the Nightmare Bacteria." Frontline. PBS. Season 2, episode 13. Television.
Abramoff et al., "Image processing with Image", J. Biophotonics International, (2004), vol. 11, pp. 36-42.
Arora et al. "Modified microplate method for rapid and efficient estimation of siderophore produced by bacteria", 3 Biotech, (2017), vol. 7, No. 6, p. 381.
Belenky et al., "Bactericidal Antibiotics Induce Toxic Metabolic Perturbations", Cell Reports, (2015), vol. 13, No. 5, pp. 968-980.
Chen et al., "Initial Drug Dissolution from Amorphous Solid Dispersions Controlled by Polymer Dissolution and Drug-Polymer Interaction", Pharm Res., (2016), vol. 33, No. 10, pp. 2445-2458.
Chung, "A specific iron stain for iron-binding proteins in polyacrylamide gels: application to transferrin and lactoferrin", Anal Biochem., (1985), vol. 148, No. 2, pp. 498-502.
Weinstein et al., "Methods for Dilution Antimicrobial Susceptibility Tests for Bacteria That Grow Aerobically", Clinical and Laboratory Standards Institute, (2018), M07 11th.
Diederichs et al., "Improved R-factors for Diffraction Data Analysis in Macromolecular Crystallography", Nature Structural Biology, (1997), vol. 4, pp. 269-275.
Dwyer et al., "Antibiotics induce redox-related physiological alterations as part of their lethality", Proc Natl Acad Sci U S A., (2014), vol. 111, No. 20, pp. E2100-E2109.
Dwyer et al., "Gyrase inhibitors induce an oxidative damage cellular death pathway in *Escherichia coli*", Mol Syst Biol., (2007), vol. 3, pp. 91.
Evans, "Biochemistry. Resolving some old problems in protein crystallography", Science, (2012), vol. 336, No. 6084, pp. 986-987.
Evans, "Scaling and assessment of data quality", Acta Crystallogr D Biol Crystallogr., (2006), vol. 62, (Pt 1), pp. 72-82.
Fish, "Rapid colorimetric micromethod for the quantitation of complexed iron in biological samples", Methods Enzymol., (1988), vol. 158, pp. 357-364.
Hedayati et al., "An optimised spectrophotometric assay for convenient and accurate quantitation of intracellular iron from iron oxide nanoparticles", Int J Hyperthermia, (2018), vol. 34, No. 4, pp. 373-381.
Jacobs et al., "A Highly Virulent Isolate of Acinetobacter baumannii, as a Model Strain for the Evaluation of Pathogenesis and Antimicrobial Treatments", MBio., (2014), vol. 5, No. 3, pp. e01076-14. 10.1128/mBio.01076-14.
Jing et al., "Methods for measuring aptamer-protein equilibria: a review", Anal Chem Acta, (2011), vol. 686, Nos. 1-2, pp. 9-18.
Karplus et al., "Linking crystallographic model and data quality", Science, (2012), vol. 336, No. 6084, pp. 1030-1033.
Konstan et al., "MBCHB for the Scientific Advisory Group and the Investigators and Coordinators of the Epidemiologic Study of Cystic Fibrosis, Risk factors for rate of decline in forced expiratory volume in one second in children and adolescents with cystic fibrosis", J Pediatr., (2007), vol. 151, No. 2, pp. 134-139, 139 e1.
Lepre et al., "Theory and Applications of NMR-Based Screening in Pharmaceutical Research", Chem. Rev., (2004), vol. 104, No. 8, pp. 3641-3675.

(56) References Cited

OTHER PUBLICATIONS

Liebschner et al., "Polder maps: improving OMIT maps by excluding bulk solvent", Acta Cryst. (2017), vol. 73, No. 2, pp. 148-157.
McNicholas et al., "Presenting your Structures: The CCPmg Molecular-Graphics Software", Acta Crystallogr D Biol Crystallogr., (2011), vol. 67, No. 4, pp. 386-394.
Mehi et al., "Perturbation of iron homeostasis promotes the evolution of antibiotic resistance", Mol Biol Evol., (2014), vol. 31, No. 10, pp. 2793-2804.
National Center for Biotechnology Information. PubChem Compound Summary for CID 66659363, 4-[2-(4-Hydroxyphenyl)ethylamino]isoindole-1,3-dione. Created Nov. 30, 2012.
O'Toole et al., "Initiation of biofilm formation in Pseudomonas fluorescens WCS365 proceeds via multiple, convergent signaling pathways: a genetic analysis", Mol Microbiol., (1998), vol. 28, No. 3, pp. 449-461.
Schwyn, "Universal chemical assay for the detection and determination of siderophores", Analytical biochemistry, (1987), vol. 160, No. 1, pp. 47-56.
Weiss, "Global indicators of X-ray data quality", Journal of Applied Crystallography, (2001), vol. 34, No. 2, pp. 130-135.
Yeom et al., "Iron homeostasis affects antibiotic-mediated cell death in Pseudomonas species", J Biol Chem., (2010), vol. 285, No. 29, pp. 22689-22695.
Hewage et al., Small Molecule Inhibitors of the BfrB-Bfd Interaction Decrease 1-7 Pseudomonas aeruginosa Fitness and Potentiate Fluoroquinolone Activity, Journal of the American Chemical Society 141, pp. 8171-8184, Apr. 30, 2019; p. 8175, figure 3(8), structures 12-13, 16.

* cited by examiner

USE OF SMALL MOLECULE INHIBITORS OF THE BFRB:BFD INTERACTION IN BIOFILMS

CROSS-REFERENCE TO RELATED APPLICATIONS

The present application claims the benefit of and priority to U.S. Provisional Patent Application 63/092,571 filed on Oct. 16, 2020 and U.S. Provisional Patent Application 63/120,405 filed on Dec. 2, 2020, each of which is incorporated herein by reference in its entirety.

U.S. GOVERNMENT RIGHTS

This invention was made with government support under grant number AI125529 awarded by the National Institutes of Health, and grant number 1158469 awarded by the National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Dec. 29, 2021, is named 144240_551862_SL.txt and is 37,820 bytes in size.

TECHNICAL FIELD

The present technology relates generally to methods useful for inhibiting biofilm formation and as well as treating bacterial cells embedded in mature films.

SUMMARY

In an aspect, the present invention includes methods of inhibiting biofilm formation, providing or increasing bacteriocidal activity within a biofilm, treating bacteria within a biofilm, or remediating a biofilm in or on a subject, the method comprising administering to the subject a compound according to Formula I

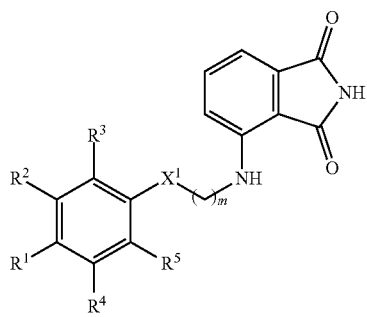

or a pharmaceutically acceptable salt and/or a solvate thereof, wherein
$R^1$ is $C_1$-$C_6$ alkoxy, H, OH, or halo;
$R^2$ and $R^3$ are each independently $C_1$-$C_6$ alkoxy, H, or OH;
$R^4$ and $R^5$ are each independently H or halo;
$X^1$ is $CH_2$ or O; and
m is 0, 1, 2, 3, 4, or 5;

provided that:
at least one of $R^1$, $R^2$, and $R^3$ is OH or $C_1$-$C_6$ alkoxy;
when $X^1$ is O, m is not 0; and
when $R^2$ is OH, $R^1$, $R^3$, $R^4$, and $R^5$ are each independently H, and $X^1$ is $CH_2$, then m is not 0; and
wherein the subject is suffering from or at risk of suffering from a bacterial infection.

In an embodiment of the invention, the method includes administering to the subject a pharmaceutical composition. In this embodiment the pharmaceutical composition can include the compound of Formula I and a pharmaceutically acceptable carrier. In this embodiment the pharmaceutical composition can be formulated for topical administration. In this embodiment the subject can be a human or a surface.

In an embodiment of the invention, the method includes administering an effective amount of fluoroquinolone antibiotic to the subject, administering an effective amount of aminoglycoside antibiotic to the subject, or administering an effective amount of polymyxin antibiotic to the subject.

In an embodiment of the invention, the bacterial infection can be a Gram-negative bacterial infection. Bacterial infections include, but are not limited to, a *Pseudomonas aeruginosa* infection, an *Acinetobacter baumannii* infection, a *Klebsiella pneumonia* infection, a *Yersinia pestis* infection, a *Shigella dysenteriae* infection, an *Enterobacter* sp. infection, an *Acinetobacter* sp. infection, a *Salmonella typhimurium* infection, a *Serratia* sp. infection, or a combination of any two or more thereof.

In an embodiment of the invention, $R^1$, $R^2$, and $R^3$ can each independently be H or OH; $R^4$ and $R^5$ can each independently be H or halo; $X^1$ can be $CH_2$ or O; and m can be 0, 1, 2, 3, 4, or 5; provided that at least one of $R^1$, $R^2$, and $R^3$ is OH. In this embodiment, $X^1$ can be $CH_2$.

In an embodiment of the invention, the compound is of Formula IA

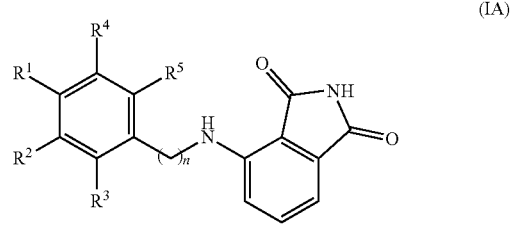

or a pharmaceutically acceptable salt and/or a solvate thereof, wherein n is 1, 2, or 3; provided that $R^2$ is not OH when n is 1 and $R^1$, $R^3$, $R^4$, and $R^5$ are each independently H. In this embodiment, one of $R^1$ and $R^3$ can be OH, one of $R^1$ and $R^3$ can be H, and $R^2$ can be H. Also in this embodiment, $R^4$ and $R^5$ can each independently be H, bromine, chlorine, or fluorine. Also in this embodiment, $R^4$ and $R^5$ can each independently be H or chlorine.

In an embodiment of the invention, the compound can be selected from

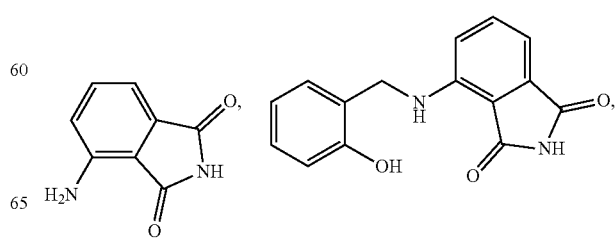

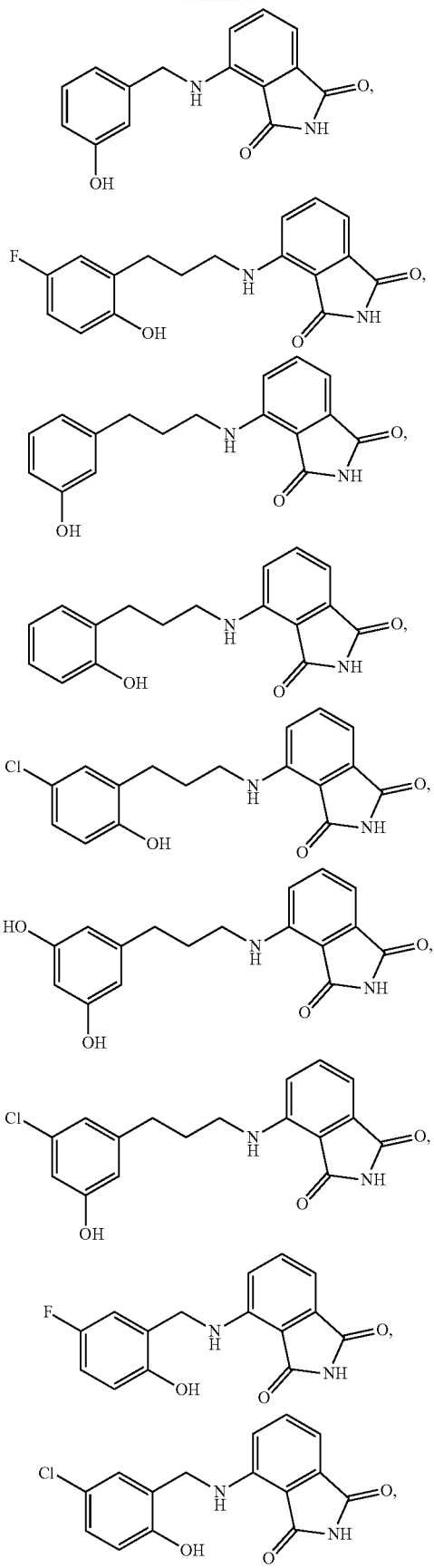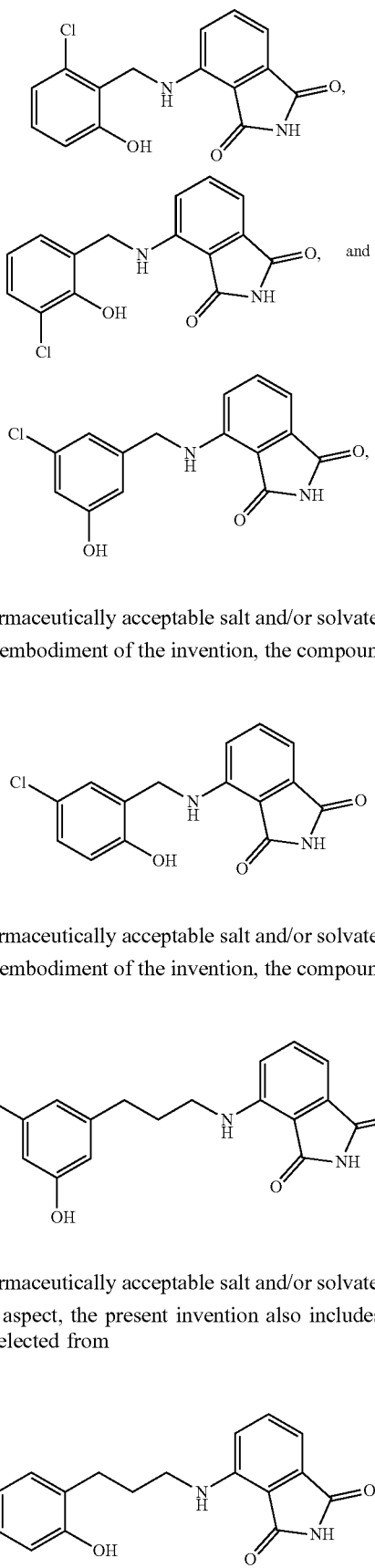

or a pharmaceutically acceptable salt and/or solvate thereof.

In an embodiment of the invention, the compound can be or a pharmaceutically acceptable salt and/or solvate thereof.

In an embodiment of the invention, the compound can be or a pharmaceutically acceptable salt and/or solvate thereof.

In an aspect, the present invention also includes a compound selected from

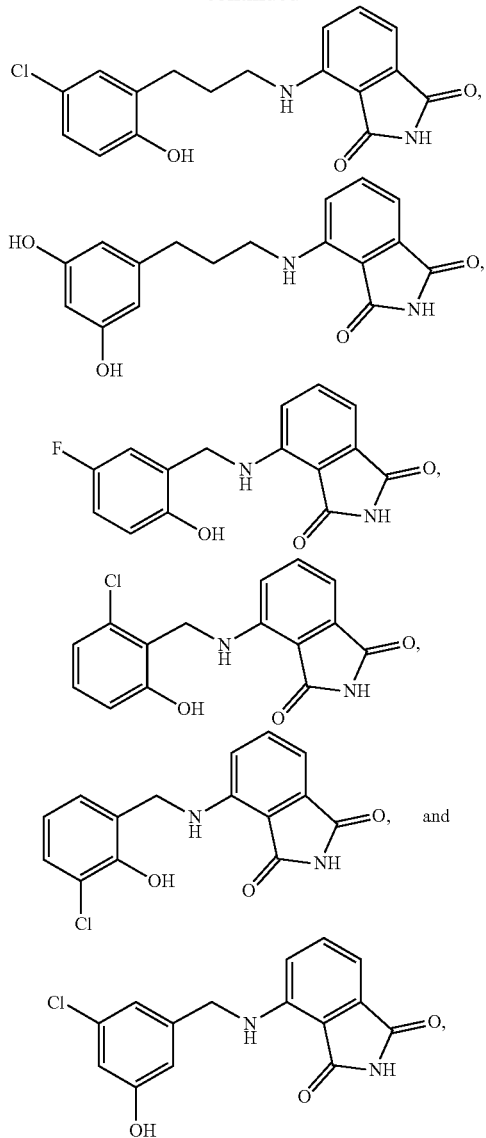

or a pharmaceutically acceptable salt and/or solvate thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 12 shows multiple sequence alignment of representative bacterioferritins. Annotated bacterioferritin sequences from different strains of Acintobacter baumannii (NCBI accession numbers in violet) and Klebsiella pneumoniae (NCBI accession numbers in orange) are placed below the Pseudomonas aeruginosa BfrB sequence (NCBI accession number in black). Residues buried at the P. aeruginosa BfrB-Bfd interface are denoted by and hot spot residues at the BfrB-Bfd interface are denoted by (Δ). Conserved residues across the alignment are in red, conservative substitutions in green and semi-conservative substitutions in blue. FIG. 12 discloses SEQ ID NOS 1, 32, and 2-20, respectively, in order of appearance.

FIG. 13 shows multiple sequence alignment of representative bacterioferritin-associated ferredoxins (Bfd). Annotated Bfd sequences from different strains of Acinetobacter baumannii (NCBI accession numbers in violet) and Klebsiella pneumoniae (NCBI accession numbers in orange) are placed below the *Pseudomonas aeruginosa* Bfd sequence (NCBI accession number in black). Conserved cysteine residues coordinating iron in the [2Fe-2S] cluster are highlighted by (↓), residues buried at the *P. aeruginosa* BfrB-Bfd interface are denoted by (*) and hot spot residues at the BfrB-Bfd interface are denoted by (A). Conserved residues across the alignment are in red, conservative substitutions in green and semi-conservative substitutions in blue. FIG. 13 discloses SEQ ID NOS 21, 33, 33, 22-24, 24, 24-25, 24, 24, 26-29, 29, 29, and 29-31, respectively, in order of appearance.

DETAILED DESCRIPTION

Figure 1:
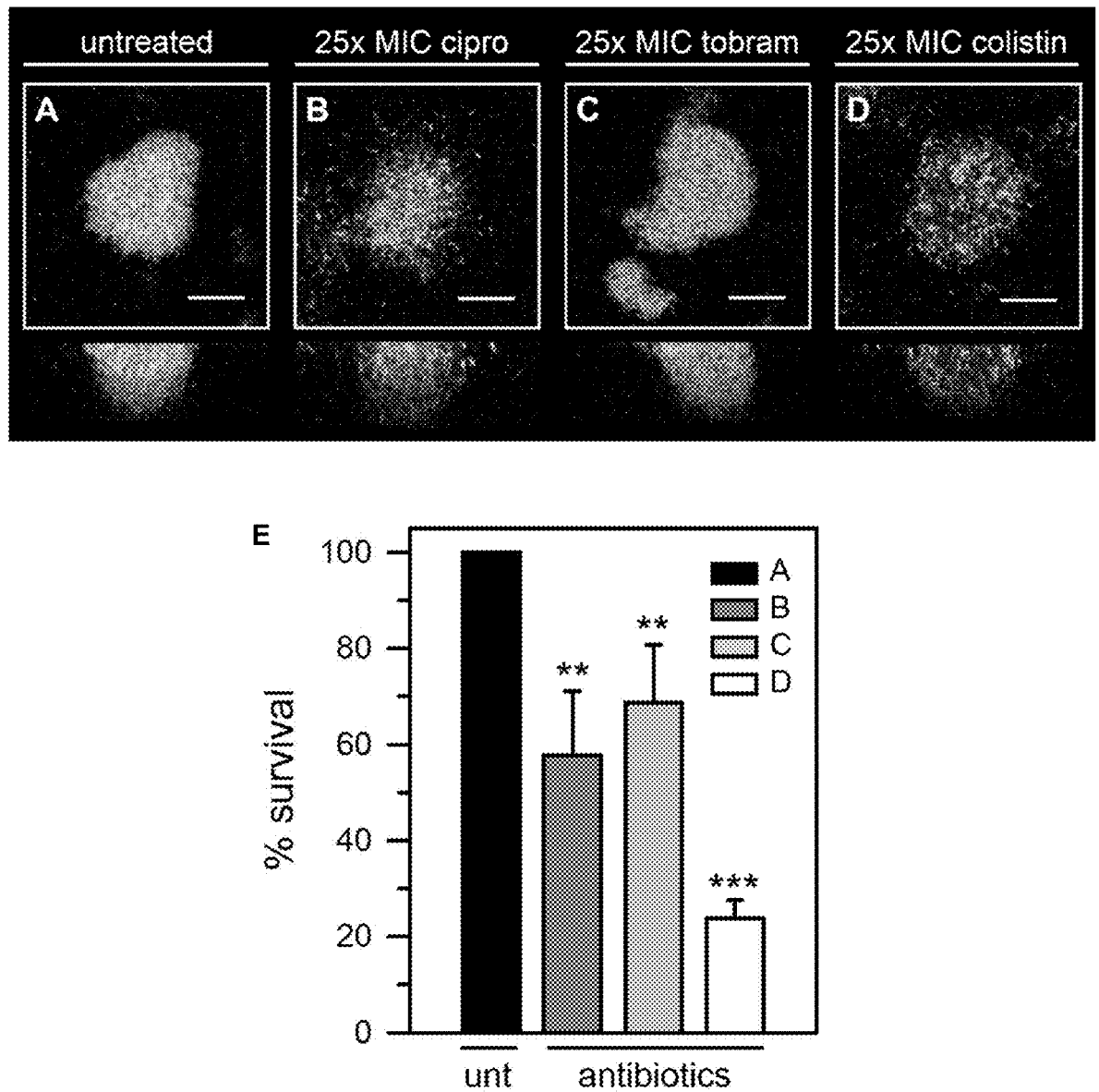
FIG. 1 illustrates that *P. aeruginosa* cells embedded in mature biofilms cultured in flow cells are tolerant to ciprofloxacin and tobramycin and susceptible to colistin. EYFP-expressing *P. aeruginosa* PAO1 biofilms were cultured for three days by flowing AB media supplemented with 15 µM Fe and then treated for 24 h by flowing the same media containing antibiotic. Biofilms were counterstained with Sytox Red and imaged with the aid of CLSM. Top-down views (x-y plane) are depicted with side views (x-z plane) at the bottom. Viable cell mass is in yellow and dead cells and extracellular DNA in red. (A) shows the untreated (DMSO) control. (B) shows treatment at 25× the MIC of ciprofloxacin (19 µM). (C) shows treatment at 25× the MIC of tobramycin (27 µM). (D) shows treatment at 25× the MIC of colistin (20 µM). (E) shows % survival obtained from viable biomass calculated with the aid of COMSTAT software. The scale of the bars represents 20 µm. $p<0.01$ denoted by  and $p<0.001$ by * relative to untreated.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term—for example, "about 10 wt. %" would mean "9 wt. % to 11 wt. %." It is to be understood that when "about" precedes a term, the term is to be construed as disclosing "about" the term as well as the term without modification by "about"—for example, "about 10 wt. %" discloses "9 wt. % to 11 wt. %" as well as disclosing "10 wt. %."

The phrase "and/or" as used in the present disclosure will be understood to mean any one of the recited members individually or a combination of any two or more thereof—for example, "A, B, and/or C" would mean "A, B, C, A and B, A and C, or B and C."

The phrase "treating bacteria in a biofilm" as used in the present disclosure will be understood by persons of ordinary skill in the art to mean reducing the number of bacteria in a biofilm.

The phrase "remediating a biofilm" as used in the present disclosure will be understood by persons of ordinary skill in the art to mean retarding or eliminating biofilm formation, reversing biofilm formation, or dissipating a biofilm. "Effective amount" refers to the amount of a compound or composition required to produce a desired effect. One example of an effective amount includes amounts or dosages that yield acceptable toxicity and bioavailability levels for therapeutic (pharmaceutical) use including, but not limited to, the treatment of a bacterial infection. As used herein, a "subject" or "patient" is a mammal, such as a cat, dog, rodent or primate. Typically the subject is a human, and, preferably, a human suffering from or suspected of suffering from pain. The term "subject" and "patient" can be used interchangeably. As used herein, "subject" also includes surfaces. Surfaces include, but are not limited to, foods, food packaging, materials, medical devices (e.g., indwelling medical devices), tools, utensils, machines, such as food processing equipment, and devices used in processing foods, such as implements.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyl, heterocyclylalkyl, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; and nitriles (i.e., CN).

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Alkyl groups may be substituted or unsubstituted. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Cycloalkyl groups may be substituted or unsubstituted. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1] hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be monosubstituted or substituted more than once, such as, but not limited to, 2,2-, 2,3-, 2,4- 2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. Cycloalkylalkyl groups may be substituted or unsubstituted. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be monosubstituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups may be substituted or unsubstituted. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, CH=CH(CH3), CH=C(CH3)2, C(CH3)=CH2, C(CH3)=CH(CH3), C(CH2CH3)=CH2, among others. Representative substituted alkenyl groups may be mono substituted or substituted more than once, such as, but not limited to, mono-, di- or tri-substituted with substituents such as those listed above.

Cycloalkenyl groups include cycloalkyl groups as defined above, having at least one double bond between two carbon atoms. Cycloalkenyl groups may be substituted or unsubstituted. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Cycloalkenylalkyl groups may be substituted or unsubstituted. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups may be substituted or unsubstituted. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CH, —C≡CCH$_3$, —CH$_2$C≡CCH$_3$, —C≡CCH$_2$CH(CH$_2$CH$_3$)$_2$, among others. Representative substituted alkynyl groups may be monosubstituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Aryl groups may be substituted or unsubstituted. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. The phrase "aryl groups" includes groups containing fused rings, such as fused aromatic-aliphatic ring systems (e.g., indanyl, tetrahydronaphthyl, and the like). Representative substituted aryl groups may be mono-substituted (e.g., tolyl) or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. Aralkyl groups may be substituted or unsubstituted. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring atoms, of which one or more is a heteroatom such as, but not limited to, N, O, and S. Heterocyclyl groups may be substituted or unsubstituted. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. The phrase includes heterocyclyl groups that have other groups, such as alkyl, oxo or halo groups, bonded to one of the ring members, referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be monosubstituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring atoms, of which, one or more is a heteroatom such as, but not limited to, N, O, and S. Heteroaryl groups may be substituted or unsubstituted. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Heterocyclylalkyl groups may be substituted or unsubstituted. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Heteroaralkyl groups may be substituted or unsubstituted. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Alkoxy groups may be substituted or unsubstituted. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms. Similarly, "aryloyl" and "aryloyloxy" refer to —C(O)-aryl groups and —O—C(O)-aryl groups.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxyl" as used herein refers to a —COOH group.

The term "ester" as used herein refers to —COOR and —C(O)O-G groups. R is independently a substituted or unsubstituted alkyl, cycloalkyl, alkenyl, alkynyl, aryl, aralkyl, heterocyclylalkyl or heterocyclyl group as defined herein. G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, NY, (3rd Edition, 1999) which can be added or removed using the procedures set forth therein and which is hereby incorporated by reference in its entirety and for any and all purposes as if fully set forth herein.

The term "amide" (or "amido") includes C- and N-amide groups, i.e., —C(O)NR$_2$, and —NRC(O)R groups, respectively. Each R is independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NRC (O)—(C$_{1-5}$ alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NRC(O)OR and —OC(O)NR$_2$ groups, respectively. Each R is independently a substituted or unsubstituted alkyl, alkenyl, alkynyl, cycloalkyl, aryl, aralkyl, heterocyclylalkyl, or heterocyclyl group as defined herein. Any R directly attached to a N atom may also be H.

The term "amine" (or "amino") as used herein refers to —NR$_2$ groups, wherein each R is independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$_2$ and —NRSO$_2$R groups, respectively. Each R is independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while "sulfides" include —SR groups, "sulfoxides" include —S(O)R groups, "sulfones" include —SO$_2$R groups, and "sulfonyls" include —SO$_2$OR. Each R is independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR—C(O)—NR$_2$ groups. Each R is independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR)NR$_2$ and —NRC(NR)R, wherein each R is independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NRC(NR)NR$_2$, wherein each R is independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R)=C(R)N$_2$ and —NRC(R)=C(R)R, wherein each R is independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxyl" as used herein can refer to —OH or its ionized form, —O$^-$. A "hydroxyalkyl" group is a hydroxyl-substituted alkyl group, such as HO—CH$_2$—.

The term "imide" refers to —C(O)NRC(O)R, wherein each R is independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR(NR) and —N(CR$_2$) groups, wherein each R is independently hydrogen or a substituted or unsubstituted alkyl, cycloalkyl, alkenyl, alkynyl, aryl aralkyl, heterocyclyl or heterocyclylalkyl group as defined herein, with the proviso that both R groups are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

The term "azido" refers to —N$_3$.

The term "trialkylammonium" refers to a —N(alkyl)$_3$ group. A trialkylammonium group is positively charged and thus typically has an associated anion, such as halogen anion.

The term "isocyano" refers to —NC.

The term "isothiocyano" refers to —NCS.

The term "pentafluorosulfanyl" refers to —SF$_5$.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g. Na$^+$, Li$^+$, K$^+$, Ca$^{2+}$, Mg$^{2+}$, Zn$^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

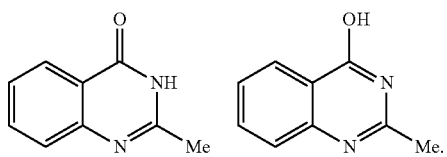

As another example, guanidines may exhibit the following isomeric forms in protic organic solution, also referred to as tautomers of each other:

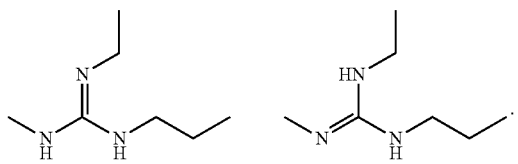

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

The Present Technology

Antibiotic resistant infections are a worldwide threat to public health. The challenge posed by the emergence of antibiotic resistant strains is compounded by slow to nearly stalled development of new antibiotics and validation of new targets.[96-98] Hence, antibiotic resistant infections have the potential to undermine many achievements in modern medicine, such as organ transplantation, major surgery and cancer chemotherapy. The World Health Organization (WHO) published a priority list for research and development of new antibiotics to combat multi-drug resistant bacteria, and assigned critical priority to the Gram-negative carbapenem-resistant *Acinetobacter baumanii* and *Pseudomonas aeruginosa*, and third-generation cephalosporin resistant Enterobacteriaceae.[1] *P. aeruginosa* is one of the leading Gram-negative pathogens associated with hospital infections due to their propensity to colonize urinary catheters and endotracheal tubes,[11-12] and accelerate lung function decay that lowers the survival of cystic fibrosis patients.[8-9] Multidrug resistant forms of *A. baumannii*, defined as resistant to three or more antibiotic drugs, account for approximately 63% of *A. baumannii* infections, and are a primary cause of pneumonia or blood stream infections among critically ill patients. The risk of mortality from both bacteria is high, especially among ventilator-associated pneumonia (VAP) patients and sepsis.[113-114] In addition to the presence of multi-drug resistant bacteria, biofilms have been implicated as a cause of antibiotic tolerant infections, even in cases where the bacteria within the biofilm have not developed a particular drug resistance.

A characteristic of biofilms is their high tolerance to antimicrobial agents. Tolerance is a physiological condition which does not involve mutation and enables bacteria to survive in the presence of antibiotics.[39-42] The persistent biofilm phenotype is thought to arise from several factors, including restricted penetration of antibiotic molecules due to interactions with components of the biofilm matrix, slow cell metabolism in the biofilm, differential expression of specific genes, and the presence of persister cells. In addition, biofilms are composed of distinct subpopulations that exhibit different physiological activity; cells in the biofilm interior exhibit low metabolic activity, distinct from the high metabolism of cells near the surface.[39, 43-44] The dissimilar metabolic activity is thought to result from a concentration gradient of $O_2$ and nutrients, which are high at the biofilm surface and low in the deeper layers of the biofilm.[44-45] Commercial antibiotics that interfere with cell replication (e.g. ciprofloxacin), or protein translation (e.g. tobramycin), preferentially treat the metabolically active bacteria in the outer biofilm layers, whereas cells in the biofilm interior survive,[43, 46-48] despite the ability of both antibiotics to diffuse into the inner regions of the biofilm.[43, 49] In contrast, some antimicrobials that affect membrane structure, such as colistin, a "last-line" therapy to treat multi-drug resistant infections,[50-52] can treat cells in the deeper biofilm layers.[48] Therefore, there is an unmet need in the art for therapeutics that treat, inhibit, or remediate bacterial biofilms in order to increase the effectiveness of commercial antibiotics that typically are ineffective against biofilms. In turn, this also speaks to the continuing need for the development of new antibiotics that can treat bacteria that reside both within and outside of a biofilm.

A. baumannii and P. aeruginosa biofilms have been implicated in diseases such as cystic fibrosis, periodontitis and urinary tract infections, partly because of an ability to colonize indwelling medical devices. The hospital cost per patent-infection ranges between $16,000-65,000, with most expenses occurring in the upper part of this range. Worldwide, the infection rates in developing countries occur at a higher frequency than in European countries and the US, especially infections causing VAP and central venous catheter-related bloodstream infections. Infections due to MDR A. baumannii are also common in combat zones, after natural disasters and in instances of high hospital trauma. The CDC has stated that "This bacteria is a serious concern and requires prompt and sustained action to ensure the problem does not grow."[96] A. baumannii has also been profiled in the mass media, most notably in a recent Frontline documentary entitled "*Hunting the Nightmare Bacteria.*"[115] According to a recent GlobalData report, a recognized leader in providing business information and analytics, "The global marketplace for healthcare-associated infections (HAIs) caused by Gram-negative bacteria across the seven major pharmaceutical markets (7MM) is projected to exceed $3.6 billion in sales by 2026, at a Compound Annual Growth Rate (CAGR) of 10.8% from 2016-2026."[116] Responding to this call requires vibrant research and continued investment in the early stages of drug development, in order to ensure a pipeline of novel ideas and approaches.[11] In this context, strategies that interfere with bacterial iron acquisition and homeostasis are regarded as having potential as new therapeutic interventions.[55, 76, 99-100] Iron is essential for bacteria because of its involvement in multiple metabolic processes, including respiration and fundamental enzymatic reactions.[101] Pathogenic bacteria must obtain iron from the host, but host nutritional immunity maintains extremely low concentrations of free iron, thus denying the essential nutrient to invading pathogens.[22, 86, 102-103] In addition, the very low solubility of the ferric ion ($Fe^{3+}$) severely limits its bioavailability, and the reactivity of the soluble ferrous iron ($Fe^{2+}$) toward hydrogen peroxide and oxygen induces oxidative stress. Consequently, the processes of bacterial iron homeostasis (acquisition, storage and utilization) are highly regulated to ensure sufficiency for metabolic needs while preventing iron-induced toxicity.[23-24] Herein, the present technology provides an unprecedented approach to dysregulate iron homeostasis in P. aeruginosa and A. baumannii which utilizes small molecule probes designed to block the interaction between the iron storage protein bacterioferritin B (BfrB) and its cognate partner, the bacterioferritin-associated ferredoxin (Bfd).

Bacteria store iron reserves in bacterial ferritin (Ftn) and in bacterioferritin (Bfr).[28, 104-105] roughly spherical and hollow structures of Bfr and bacterial Ftn, which are formed from 24 identical subunits, have an outer diameter of ~120 Å, an inner diameter of ~80 Å, and an interior cavity that can store up to ~3,000 iron ions in the form of a $Fe^{3+}$ mineral. Bfrs, which exist only in bacteria, bind 12 heme groups buried under the external protein surface, with the heme propionates protruding into the interior cavity.[104-105] Despite sharing a nearly identical subunit fold and quaternary structures, the eukaryotic Ftns and the Bfrs share less than 20% sequence similarity, which results in divergent subunit packing, 24-mer dynamics and function.[28, 106-108] Although in P. aeruginosa the ftnA and bfrB genes encode a bacterial ferritin (FtnA) and a bacterioferritin (BfrB), respectively,[29, 31] BfrB functions as the main iron storage protein.[23] Importantly, the mobilization of iron stored in BfrB requires specific interactions with Bfd.[23, 28, 31] A crystal structure of the BfrB-Bfd complex revealed that up to 12 Bfd molecules can bind at identical sites on the BfrB surface, at the interface of subunit dimers, above a heme molecule.[30] Characterization of the complex in solution showed that the 12 Bfd binding sites are equivalent and independent, and that Bfd binds to BfrB with a $K_d$ of approximately 3 μM.[110] These investigations also revealed that M1, Y2 and L5 in Bfd form a continuous set of interactions with L68 and E81 in BfrB, which contribute significantly to the stabilization of the BfrB-Bfd complex. In agreement, the $K_d$ values for the association between Bfd and the L68A or E81A mutants of BfrB are approximately 100-fold larger, and the association between Bfd and the BfrB L68A/E81A double mutant is undetectable.[110]

Importantly, alignment of the P. aeruginosa BfrB and Bfd sequences against Bfir and Bfd sequences from E. coli 0157, Klebsiella pneumoniae, Yersinia pestis, Shigella dysenteriae, Enterobacter sp., Acinetobacter sp., Salmonella typhimurium and Serratia sp. shows that the key residues at the interface of the BfrB:Bfd complex in P. aeruginosa are conserved in the sequences of Bfr and Bfd proteins in the above-listed Gram-negative pathogens.[30, 110] Hence, inhibitors of the BfrB-Bfd complex in P. aeruginosa will inhibit the equivalent complex in these other Gram-negative organisms and be a target for small-molecule inhibition and intervention.

The repercussions of blocking the BfrB-Bfd interaction on P. aeruginosa iron metabolism have been investigated by deleting the bfd gene. These investigations, which showed an irreversible accumulation of $Fe^{3+}$ in BfrB with concomitant iron deprivation in the cytosol, established the BfrB-Bfd interaction as a novel target to rationally induce iron homeostasis dysregulation in bacteria.[23] Consequently, it is important to discover small molecule inhibitors of the BfrB-Bfd interaction, which can (in addition to their use for treating bacterial infections) be used as chemical probes to study bacterial iron homeostasis and uncover additional vulnerabilities in the bacterial cell exposed by iron metabolism dysregulation.[28, 105]

The present technology provides methods useful for inhibiting biofilm formation and as well as treating bacterial cells embedded in biofilms.

In an aspect, the present technology provides a method of inhibiting biofilm formation in or on a subject, the method comprising administering to the subject a compound according to Formula I

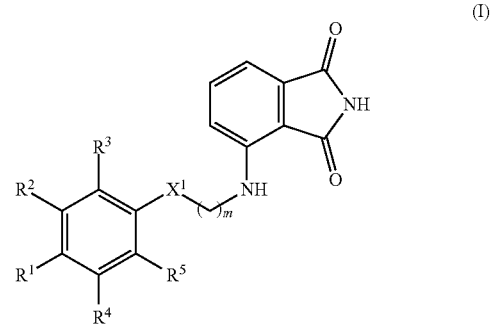

or a pharmaceutically acceptable salt and/or a solvate thereof, wherein
$R^1$ is $C_1$-$C_6$ alkoxy, H, OH, or halo;
$R^2$ and $R^3$ are each independently $C_1$-$C_6$ alkoxy, H, or OH;

R⁴ and R⁵ are each independently H or halo;
X¹ is CH₂ or O; and
m is 0, 1, 2, 3, 4, or 5;
provided that:
  at least one of R¹, R², and R³ is OH or C₁-C₆ alkoxy;
  when X¹ is O, m is not 0; and
  when R² is OH, R¹, R³, R⁴, and R⁵ are each independently H, and X¹ is CH₂, then m is not 0; and
wherein the subject is suffering from or at risk of suffering from a bacterial infection. Throughout the present disclosure, a compound according to Formula I (or a pharmaceutically acceptable salt and/or a solvate thereof) are also referred to as "a compound of the present technology," "compounds of the present technology," or the like. In any embodiment herein, the method may include administering an effective amount of the compound (wherein the effective amount is effective to inhibit biofilm formation). In any embodiment herein, the method may further include administering one or more of a fluoroquinolone antibiotic (e.g., ciprofloxacin), an aminoglycoside antibiotic (e.g., tobramycin), and a polymyxin antibiotic (e.g., colistin) to the subject, such as administering an effective amount of fluoroquinolone antibiotic to the subject, administering an effective amount of aminoglycoside antibiotic (e.g., tobramycin) to the subject, and/or administering an effective amount of polymyxin antibiotic (e.g., colistin) to the subject. In any embodiment herein, it may be that the bacterial infection comprises a Gram-negative bacterial infection. In any embodiment herein, it may be that the bacterial infection comprises a *Pseudomonas aeruginosa* infection, an *Acinetobacter baumannii* infection, a *Klebsiella pneumonia* infection, a *Yersinia pestis* infection, a *Shigella dysenteriae* infection, an *Enterobacter* sp. infection, an *Acinetobacter* sp. infection, a *Salmonella typhimurium* infection, a *Serratia* sp. infection, or a combination of any two or more thereof. In any embodiment herein, the administration may include oral administration, parenteral administration, nasal administration, or topical administration. In any of these embodiments, the administration may further include subcutaneous injections, intravenous injections, intraperitoneal injections, or intramuscular injections.

In an aspect, the present technology provides a method of remediating a biofilm in or on a subject, the method comprising administering to the subject a compound according to Formula I or a pharmaceutically acceptable salt and/or a solvate thereof, wherein the subject is suffering from a bacterial infection. In any embodiment herein, the method may include administering an effective amount of the compound (wherein the effective amount is effective to inhibit biofilm formation). In any embodiment herein, the method may further include administering one or more of a fluoroquinolone antibiotic, an aminoglycoside antibiotic (e.g., tobramycin), and a polymyxin antibiotic (e.g., colistin) to the subject, such as administering an effective amount of fluoroquinolone antibiotic to the subject, administering an effective amount of aminoglycoside antibiotic (e.g., tobramycin) to the subject, and/or administering an effective amount of polymyxin antibiotic (e.g., colistin) to the subject. In any embodiment herein, it may be that the bacterial infection comprises a Gram-negative bacterial infection. In any embodiment herein, it may be that the bacterial infection comprises a *Pseudomonas aeruginosa* infection, an *Acinetobacter baumannii* infection, a *Klebsiella pneumonia* infection, a *Yersinia pestis* infection, a *Shigella dysenteriae* infection, an *Enterobacter* sp. infection, an *Acinetobacter* sp. infection, a *Salmonella typhimurium* infection, a *Serratia* sp. infection, or a combination of any two or more thereof. In any embodiment herein, the administration may include oral administration, parenteral administration, nasal administration, or topical administration. In any of these embodiments, the administration may further include subcutaneous injections, intravenous injections, intraperitoneal injections, or intramuscular injections.

In an aspect, the present technology provides a method of increasing bacteriocidal activity within a biofilm in or on a subject, the method comprising administering to the subject a compound according to Formula I or a pharmaceutically acceptable salt and/or a solvate thereof. In an aspect, the present technology provides a method of inhibiting bacterial growth/proliferation/activity within a biofilm in or on a subject, the method comprising administering to the subject a compound according to Formula I or a pharmaceutically acceptable salt and/or a solvate thereof. In an aspect, the present technology provides a method of increasing bacterial lysis within a biofilm in or on a subject, the method comprising administering to the subject a compound according to Formula I or a pharmaceutically acceptable salt and/or a solvate thereof. In an aspect, the present technology provides a method of treating bacteria within a biofilm in or on a subject, the method comprising administering to the subject a compound according to Formula I or a pharmaceutically acceptable salt and/or a solvate thereof. In any aspect, it may be that the method includes administering an effective amount of the compound. In any embodiment herein, the method may further include administering one or more of a fluoroquinolone antibiotic, an aminoglycoside antibiotic (e.g., tobramycin), and a polymyxin antibiotic (e.g., colistin) to the subject, such as administering an effective amount of fluoroquinolone antibiotic to the subject, administering an effective amount of aminoglycoside antibiotic (e.g., tobramycin) to the subject, and/or administering an effective amount of polymyxin antibiotic (e.g., colistin) to the subject. In any aspect, it may be that the bacteria in the biofilm include Gram-negative bacteria. In any aspect, it may be that the bacteria in the biofilm include *Pseudomonas aeruginosa*, *Acinetobacter baumannii*, *Klebsiella pneumonia*, *Yersinia pestis*, *Shigella dysenteriae*, *Enterobacter* sp., *Acinetobacter* sp., *Salmonella typhimurium*, *Serratia* sp., or a combination of any two or more thereof. In any aspect and any embodiment herein, the administration may include oral administration, parenteral administration, nasal administration, or topical administration. In any of these embodiments, the administration may further include subcutaneous injections, intravenous injections, intraperitoneal injections, or intramuscular injections.

In any aspect and any embodiment herein (hereafter simply referred to as "in any embodiment herein" or "any embodiment disclosed herein" or the like), it may be at least one of R¹, R², and R³ is OH, and the remaining R¹, R², and R³ are each independently H or OH; R⁴ and R⁵ are each independently H or halo; X¹ is CH₂ or O; and m is 0, 1, 2, 3, 4, or 5; provided that when X¹ is O, m is not 0; and provided that when $R^2$ is OH, $R^1$, $R^3$, $R^4$, and $R^5$ are each independently H, and $X^1$ is $CH_2$, m is not 0.

In any embodiment disclosed herein, it may be that the compound of Formula I is of Formula IA

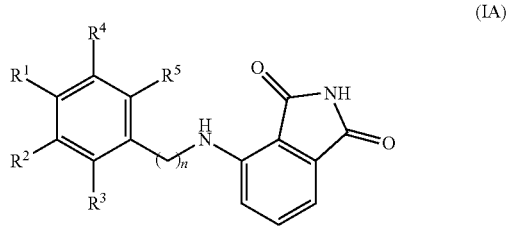

(IA)

or a pharmaceutically acceptable salt and/or a solvate thereof, wherein n is 1, 2, or 3; provided that $R^2$ is not OH when n is 1 and $R^1$, $R^3$, $R^4$, and $R^5$ are each independently H. In any embodiment disclosed herein, it may be that one of $R^1$ and $R^3$ is OH, one of $R^1$ and $R^3$ is H, and $R^2$ is H. In any embodiment disclosed herein, it may be that $R^4$ and $R^5$ are each independently H, bromine, chlorine, or fluorine. In any embodiment disclosed herein, it may be that $R^4$ and $R^5$ are each independently H or chlorine.

In any embodiment herein, it may be a composition is provided that includes any one of the herein-described embodiments of compounds of Formula I and also includes a pharmaceutically acceptable carrier. In any embodiment herein, it may be that a compound of the present technology is part of a pharmaceutical composition, the pharmaceutical composition including an effective amount of the compound of any one of the aspects and embodiments of compounds of Formula I and a pharmaceutically acceptable carrier.

Thus, the instant present technology provides compostions, pharmaceutical compositions and medicaments comprising any of the compounds disclosed herein (e.g., compounds of Formula I) and a pharmaceutically acceptable carrier or one or more excipients or fillers. The compositions may be used in the methods and treatments described herein. Such compositions and medicaments include a therapeutically effective amount of any compound as described herein, including but not limited to a compound of Formula I. The pharmaceutical composition may be packaged in unit dosage form. The unit dosage form is effective in treating a bacterial infection when administered to a subject in need thereof.

The pharmaceutical compositions and medicaments may be prepared by mixing one or more compounds of the present technology, pharmaceutically acceptable salts thereof, stereoisomers thereof, tautomers thereof, or solvates thereof, with pharmaceutically acceptable carriers, excipients, binders, diluents or the like. The compounds and compositions described herein may be used to prepare formulations and medicaments that prevent or treat a bacterial infection. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

For oral, buccal, and sublingual administration, powders, suspensions, granules, tablets, pills, capsules, gelcaps, and caplets are acceptable as solid dosage forms. These can be prepared, for example, by mixing one or more compounds of the instant present technology, or pharmaceutically acceptable salts or tautomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aqueous and nonaqueous (e.g., in a fluorocarbon propellant) aerosols are typically used for delivery of compounds of the present technology by inhalation.

Forms for the topical administration of compounds of the present technology on a surface include powders, sprayspastes, creams, lotions, gels, solutions, and patches. Dosage forms for the topical (including buccal and sublingual) or transdermal administration of compounds of the present technology include powders, sprays, ointments, pastes, creams, lotions, gels, solutions, and patches. The active component may be mixed under sterile conditions with a pharmaceutically-acceptable carrier or excipient, and with any preservatives, or buffers, which may be required. Powders and sprays can be prepared, for example, with excipients such as lactose, talc, silicic acid, aluminum hydroxide, calcium silicates and polyamide powder, or mixtures of these substances. The ointments, pastes, creams and gels may also contain excipients such as animal and vegetable fats, oils, waxes, paraffins, starch, tragacanth, cellulose derivatives, polyethylene glycols, silicones, bentonites, silicic acid, talc and zinc oxide, or mixtures thereof. Absorption enhancers can also be used to increase the flux of the compounds of the present technology across the skin. The rate of such flux can be controlled by either providing a rate controlling membrane (e.g., as part of a transdermal patch) or dispersing the compound in a polymer matrix or gel.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant present technology.

Those skilled in the art are readily able to determine an effective amount by simply administering a compound of the present technology to a patient in increasing amounts until, for example, culture of the bacterial infection indicates a reduction in the number of bacteria and/or the symptoms of the bacterial infection decrease (e.g., as indicated by the patient). The compounds of the present technology can be administered to a patient at dosage levels in the range of about 0.1 to about 1,000 mg per day. For a normal human adult having a body weight of about 70 kg, a dosage in the range of about 0.01 to about 100 mg per kg of body weight per day may be sufficient (e.g., a dosage in the range of about 0.01 to about 10 mg per kg of body weight per day may be sufficient). The specific dosage used, however, can vary or may be adjusted as considered appropriate by those of ordinary skill in the art. For example, the dosage can depend on a number of factors including the requirements of the patient, the severity of the bacterial infection and the pharmacological activity of the compound being used. The determination of optimum dosages for a particular patient is well known to those skilled in the art.

Various assays and model systems can be readily employed to determine the therapeutic effectiveness of the treatment according to the present technology. Effectiveness of the compositions and methods of the present technology may also be demonstrated by a culture of the bacterial infection indicating a reduction in the number of bacteria subsequent to administering a compound and/or composition of the present technology and/or the symptoms of the bacterial infection decrease (e.g., as indicated by the patient).

For each of the indicated conditions described herein, test subjects will exhibit a 10%, 20%, 30%, 50% or greater reduction, up to a 75-90%, or 95% or greater, reduction, in one or more symptom(s) caused by, or associated with, the disorder in the subject, compared to placebo-treated or other suitable control subjects.

As indicated earlier in this disclosure, the compounds of the present technology can also be administered to a patient along with other conventional therapeutic agents that may be useful in the treatment of a bacterial infection, such as a fluoroquinolone antibiotic, an aminoglycoside antibiotic, and/or a polymyxin antibiotic. In any embodiment herein, a compound and/or composition of the present technology may be administered along with an effective amount of a fluoroquinolone antibiotic, an effective amount of a aminoglycoside antibiotic, and/or a polymyxin antibiotic. The administration may include oral administration, parenteral administration, nasal administration, or topical administration. In any of these embodiments, the administration may include subcutaneous injections, intravenous injections, intraperitoneal injections, or intramuscular injections. In any of these embodiments, the administration may include oral administration. The methods of the present technology can also comprise administering, either sequentially or in combination with one or more compounds of the present technology, a conventional therapeutic agent (e.g., a fluoroquinolone antibiotic, a aminoglycoside antibiotic, and/or a polymyxin antibiotic) in an amount that can potentially or synergistically be effective for the treatment of a bacterial infection.

In an aspect, a compound of the present technology is administered to a patient in an amount or dosage suitable for therapeutic use. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising a compound of the present technology can vary from $1 \times 10^{-4}$ g/kg to 1 g/kg, preferably, $1 \times 10^{-3}$ g/kg to 1.0 g/kg. Dosage of a compound of the present technology can also vary from 0.01 mg/kg to 100 mg/kg or, preferably, from 0.1 mg/kg to 10 mg/kg.

A compound of the present technology can also be modified, for example, by the covalent attachment of an organic moiety or conjugate to improve pharmacokinetic properties, toxicity or bioavailability (e.g., increased in vivo half-life). The conjugate can be a linear or branched hydrophilic polymeric group, fatty acid group or fatty acid ester group. A polymeric group can comprise a molecular weight that can be adjusted by one of ordinary skill in the art to improve, for example, pharmacokinetic properties, toxicity or bioavailability. Exemplary conjugates can include a polyalkane glycol (e.g., polyethylene glycol (PEG), polypropylene glycol (PPG)), carbohydrate polymer, amino acid polymer or polyvinyl pyrolidone and a fatty acid or fatty acid ester group, each of which can independently comprise from about eight to about seventy carbon atoms. Conjugates for use with a compound of the present technology can also serve as linkers to, for example, any suitable substituents or groups, radiolabels (marker or tags), halogens, proteins, enzymes, polypeptides, other therapeutic agents (for example, a pharmaceutical or drug), nucleosides, dyes, oligonucleotides, lipids, phospholipids and/or liposomes. In one aspect, conjugates can include polyethylene amine (PEI), polyglycine, hybrids of PEI and polyglycine, polyethylene glycol (PEG) or methoxypolyethylene glycol (mPEG). A conjugate can also link a compound of the present technology to, for example, a label (fluorescent or luminescent) or marker (radionuclide, radioisotope and/or isotope) to comprise a probe of the present technology. Conjugates for use with a compound of the present technology can, in one aspect, improve in vivo half-life. Other exemplary conjugates for use with a compound of the present technology as well as applications thereof and related techniques include those generally described by U.S. Pat. No. 5,672,662, which is hereby incorporated by reference herein.

The examples herein are provided to illustrate advantages of the present technology and to further assist a person of ordinary skill in the art with preparing or using the compounds of the present technology. The examples herein are also presented in order to more fully illustrate the preferred aspects of the present technology. The examples should in no way be construed as limiting the scope of the present technology, as defined by the appended claims. The examples can include or incorporate any of the variations, aspects, or embodiments of the present technology described above. The variations, aspects, or embodiments described above may also further each include or incorporate the variations of any or all other variations, aspects or embodiments of the present technology.

EXAMPLES

Example 1: Compounds

The following compounds were synthesized consistent with the procedures described in PCT International Publication No. WO 2020/117832, the entire contents of which are incorporated herein by reference.

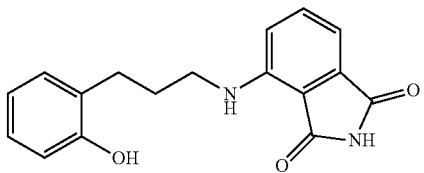 [SMILES: O=C1NC(=O)c2c(NCCCc3ccccc3O)cccc21]

4-((3-(2-Hydroxyphenyl)amino)isoindoline-1,3-dione (KM-5-28). Yellow solid, mp 132-133° C. $^3$H NMR (400 MHz, DMSO-d$_6$): δ 10.93 (br s, 1H), 9.30 (s, 1H), 7.51 (t, J=7.6 Hz, 1H), 7.06 (d, J=7.6 Hz, 1H), 7.02-6.94 (complex, 2H), 6.92 (d, J=7.0 Hz, 1H), 6.78 (d, J=1H), Hz, 1H), 6.71 (t, J=7.4 Hz, 1H), 6.57 (br t, J=5.9 Hz, 1H), 3.27 (q, J=6.5 Hz, 2H), 2.60 (t, J=7.3 Hz, 2H), 1.82 (quintet, J=13 Hz, 2H); $^{13}$C NMR (101 MHz, DMSO-d$_6$): δ 171.9, 170.5, 155.6, 146.3, 136.3, 134.1, 130.2, 128.0, 127.4, 119.4, 116.9, 115.3, 112.7, 110.2, 41.9, 29.3, 27.3.

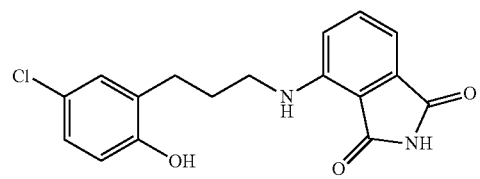 [SMILES: O=C1NC(=O)c2c(NCCCc3cc(Cl)ccc3O)cccc21]

4-((3-(5-Chloro-2-hydroxyphenyl)amino)isoindoline-1,3-dione (KM-5-54). Yellow solid, mp 224-225° C. $^1$H NMR (400 MHz, DMSO-d$_6$): δ 1093 (br s, 1H), 9.64 (s, 1H), 7.52 (dd, J=8.5, 7.2 Hz, 1H), 7.12 (d, J=2.7 Hz, 1H), 7.03 (dd, J=8.5, 2.7 Hz, 1H), 6.96 (d, J=8.5 Hz, 1H), 6.92 (d, J=7.0 Hz, 1H), 6.78 (d, J=8.6 Hz, 1H), 6.58 (br t, J=6.1 Hz, 1H), 3.28 (q, J=6.9 Hz, 2H), 2.59 (t, J=13 Hz, 2H), 1.82 (quintet, J=7.3 Hz, 2H); $^{13}$C NMR (101 MHz, DMSO-d$_6$): δ 171.9, 169.8, 154.6, 146.7, 136.3, 134.1, 130.4, 129.7, 127.0, 122.7, 116.9, 116.8, 111.2, 110.2, 41.9, 29.0, 27.1.

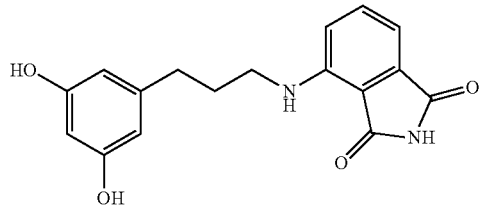 [SMILES: O=C1NC(=O)c2c(NCCCc3cc(O)cc(O)c3)cccc21]

4-((3-(3,5-Diydroxyphenyl)amino)isoindoline-1,3-dione (KM-5-57). Yellow solid, mp 208-210° C. $^1$H NMR (400 MHz, DMSO-d$_6$): δ 10.94 (br s, 1H), 9.05 (s, 2H), 7.52 (dd, J=8.3, 7.3 Hz, 1H), 6.97 (d, J=8.4 Hz, 1H), 6.93 (d, J=7.0 Hz, 1H), 6.51 (br t, J=5.9 Hz, 1H), 6.05 (d, J=2.0 Hz, 2H), 6.02 (t, J=2.0 Hz, 1H), 3.26 (q, J=6.7 Hz, 2H), 2.46 (t, J=7.6 Hz, 2H), 1.80 (quintet, J=7.6 Hz, 2H); $^{13}$C NMR (101 MHz, DMSO-d$_6$): δ 171.4, 169.3, 158.3, 146.2, 143.3, 135.9, 133.6, 116.4, 110.8, 109.8, 106.3, 100.2, 41.3, 32.4, 30.0.

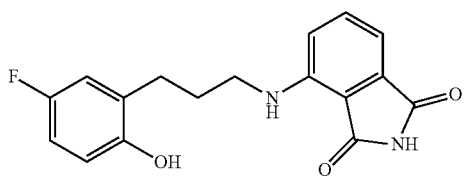 [SMILES: O=C1NC(=O)c2c(NCCCc3cc(F)ccc3O)cccc21]

4-((5-Fluoro-2-hydroxybenzyl)amino)isoindoline-1,3-dione (JAG-5-7). Prepared using Procedure A as described in WO 2020/117832. Orange solid, mp 216-217° C. $^1$H NMR (400 MHz, DMSO-$d_6$): δ 10.97 (s, 1H), 9.75 (s, 1H), 7.50 (t, J=7.7 Hz, 1H), 7.07 (br t, J=6.4 Hz, 1H), 7.02 (dd, J=9.5, 3.2 Hz, 1H), 6.98-6.86 (complex, 3H), 6.82 (dd, J=8.8, 4.7 Hz, 1H), 4.43 (d, J=6.3 Hz, 2H); $^{13}$C NMR (101 MHz, DMSO-$d_6$): δ 171.8, 169.8, 155.9 (d, J=233.9 Hz), 151.8, 146.4, 136.3, 134.1, 126.9 (d, J=6.6 Hz), 117.1, 116.3 (d, J=8.0 Hz), 115.1 (d, J=23.3 Hz), 114.6 (d, J=22.5 Hz), 111.7, 110.6, 41.1.

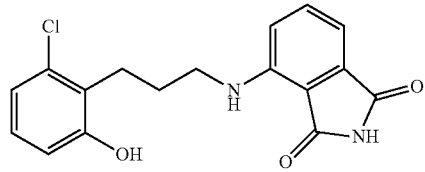 [SMILES: O=C1NC(=O)c2c(NCCCc3c(O)cccc3Cl)cccc21]

4-((6-Chloro-2-hydroxybenzyl)amino)isoindoline-1,3-dione (KM-5-29). Prepared using Procedure A as described in WO 2020/117832. Yellow solid, mp 235-236° C. $^1$H NMR (400 MHz, DMSO-$d_6$): δ 10.97 (br s, 1H), 10.43 (s, 1H), 7.56 (dd, J=8.4, 7.3 Hz, 1H), 7.29 (d, J=8.4 Hz, 1H), 7.15 (t, J=8.1 Hz, 1H), 6.95 (d, J=7.0 Hz, 1H), 6.92 (dd, J=8.1, 0.9 Hz, 1H), 6.86 (dd, J=8.1, 0.9 Hz, 1H), 6.75 (br t, J=6.2 Hz, 1H), 4.56 (d, J=6.2 Hz, 2H); $^{13}$C NMR (101 MHz, DMSO-$d_6$): δ 172.0, 169.7, 157.5, 146.4, 136.4, 134.5, 134.2, 130.2, 122.9, 120.5, 117.1, 114.9, 111.7, 110.8, 38.9.

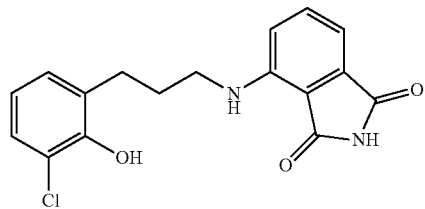 [SMILES: O=C1NC(=O)c2c(NCCCc3cccc(Cl)c3O)cccc21]

4-((3-Chloro-2-hydroxybenzyl)amino)isoindoline-1,3-dione (KM-5-30). Prepared using Procedure A as described in WO 2020/117832. Yellow solid, mp 200-202° C. $^1$H NMR (400 MHz, DMSO-$d_6$): δ 10.97 (br s, 1H), 9.56 (s, 1H), 7.48 (t, J=7.8 Hz, 1H), 7.26 (dd, J=7.9, 1.0 Hz, 1H), 7.19 (d, J=8.6 Hz, 1H), 7.06 (br t, J=6.3 Hz, 1H), 6.93 (d, J=7.7 Hz, 2H), 6.81 (t, J=7.8 Hz, 1H), 4.51 (d, J=6.3 Hz, 2H); $^{13}$C NMR (101 MHz, DMSO-$d_6$): δ 169.1, 169.0, 166.8, 156.9, 144.1, 136.1, 132.8, 125.1, 124.2, 121.9, 121.0, 120.5, 120.2, 110.8 (benzylic carbon coincident with a solvent peak).

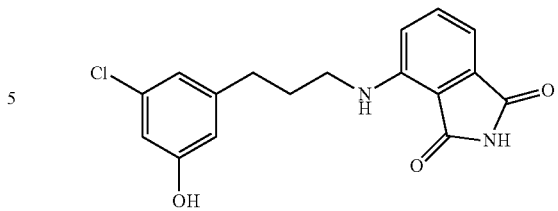

4-((5-Chloro-3-hydroxybenzyl)amino)isoindoline-1,3-dione (KM-5-50). Prepared using Procedure A as described in WO 2020/117832. Orange solid, mp 223-224° C.; $^1$H NMR (400 MHz, DMSO-$d_6$): δ 11.0 (s, 1H), 9.87 (s, 1H), 7.47 (dd, J=8.2, 7.5 Hz, 1H), 7.17 (t, J=6.5 Hz, 1H), 6.94 (d, J=7.0 Hz, 1H), 6.86 (d, J=8.3 Hz, 1H), 6.83 (s, 1H), 6.70 (s, 1H), 6.66 (t, J=2.0 Hz, 1H), 4.46 (d, J=6.5 Hz, 2H); $^{13}$C NMR (101 MHz, DMSO-$d_6$): δ 171.7, 169.8, 159.1, 146.2, 143.4, 136.3, 134.1, 133.9, 117.7, 117.4, 114.3, 113.0, 111.7, 110.8, 45.3.

Example 2: Materials and Methods for In Vitro and In Vivo Bioassays

Chemicals, Bacterial Strains, and Growth Media

Chemicals were purchased from Fisher Scientific (Waltham, MA) unless otherwise stated. *P. aeruginosa* PAO1 was obtained from the University of Washington Genome center.[80] The PAO1 strain expressing enhanced yellow fluorescent protein (EYFP) was prepared as described in Soldano, A.; Yao, H.; Chandler, J. R.; Rivera, M. (2020) Inhibiting Iron Mobilization from Bacterioferritin in *Pseudomonas aeruginosa* Impairs Biofilm Formation Irrespective of Environmental Iron Availability. *ACS Infect. Dis.* 6, 447-458. 10.1021/acsinfecdis.9b00398.[26] Clinical isolates of *P. aeruginosa* were purchased from JMI Laboratories (North Liberty, IA, USA). $IC_{50}$ determinations were carried out in defined media (50 mM $KH_2PO_4$ (Sigma Aldrich, St. Louis, MO) 7.5 mM $(NH_4)_2SO_4$ (Sigma Aldrich, St. Louis, MO), 0.1% (w/v) glucose (Acros Organics, Fair Lawn, NJ, 99+%), 0.5 mM $MgSO_4 \cdot 7H_2O$ (Sigma Aldrich, St. Louis, MO, 99+%), 5% v/v non-essential amino acids (Gibco, Thermo Fisher, Waltham, MA), 2% v/v essential amino acids (Gibco, Thermo Fisher, Waltham, MA), 4 μM $(NH_4)_2Fe(SO_4)_2$, and 0.025% (w/v) hypromellose (HPMC, Sigma Aldrich, St. Louis, MO), pH 7.0. The media was filter-sterilized by passing through a 0.2 μm cellulose acetate membrane syringe filter (VWR, Radnor, PA). Starter cultures of *P. aeruginosa* PAO1 in 5 mL LB media were grown for 13 hours in 50 mL conical tubes at 37° C. and 220 rpm. For biofilm experiments, a EYFP-expressing *P. aeruginosa* strain was routinely grown in *Pseudomonas* Isolation (PI) media (20 g $L^{-1}$ peptone, 0.3 g $L^{-1}$ $MgCl_2 \cdot 6H$ O, 10 g $L^{-1}$ $K_2SO_4$, 25 mg $L^{-1}$ irgasan, and 20 mL $L^{-1}$ glycerol, pH 7.0). Starter cultures were grown from a single colony at 37° C. and shaking at 220 rpm for 14 hours in 5 mL PI media supplemented with 10 μM Fe. Pellicle biofilms were cultured for 48 hours at 30° C. in PI media supplemented with 20 μM Fe. Surface-attached biofilms were cultured in AB minimal media[81] supplemented with trace metals [0.15 μM $(NH_4)_2MoO_4$, 3 μM $CuSO_4$, 2 μM $Co(NO_3)_2$, 9.4 μM $Na_2B_4O_7$, and 7.6 μM $ZnSO_4$], 3 mM glucose and 15 μM Fe. Iron supplementation was carried out by addition of a small volume of filter-sterilized 10 mM $(NH_4)_2Fe(SO_4)_2$ (pH~2.0) solution. The antibiotics ciprofloxacin, colistin and tobramycin were used at concentrations equivalent to 25× and 50× the reported MCI:[82] ciprofloxacin MIC=0.25 μg/mL=0.75 μM; tobramycin MIC=0.5 μg/mL=1.07 μM; colistin MIC=1 μg/mL=0.79 μM. Compound stock solutions (100 mM or 10 mM) in DMSO (Sigma Aldrich, St. Louis, MO) were prepared weekly and stored at 4° C. Solutions used to treat biofilms or planktonic cells include 0.025% (w/v) HPMC, and 1.5% or 2% DMSO (Sigma Aldrich, St. Louis, MO) to prevent aggregation of the analogs in aqueous solution.

Measurement of Dissociation Constant ($K_d$)

Dissociation constants for the interaction between BfrB and 4-aminoisoindoline-1,3-dione derivatives (Table 1 below) were measured in vitro with a fluorescence polarization method based on the intrinsic fluorescence of the isoindoline-1,3-dione moiety, as described previously.[25]

Measurement of Half Maximal Inhibitory Concentration ($IC_{50}$)

$IC_{50}$ values (Table 1 below) were determined as reported previously[25] with small modifications. In brief: precultures of *P. aeruginosa* PAO1 (5 mL) were grown in LB media for 13 hours at 37° C. and 220 rpm in 50 mL conical tubes (VWR International, PA). The cells were centrifuged for 5 min at 4,000 rpm and 4° C., washed two times and then diluted in buffer (100 mM $KH_2PO_4$ and 15 mM $(NH_4)_2SO_4$ to an optical density at 600 nm ($OD_{600}$) of 0.1. A small volume of compound stock solution (10 mM) was transferred to a microcentrifuge tube, initially diluted with DMSO to 20 μL, and then diluted to 1 mL with preculture cell suspension in defined media with $OD_{600}$=0.0001, so the final DMSO concentration is 2%. The resultant cell suspension (200 μL) was transferred to a clear-bottom polystyrene 96-well plate (VWR International, PA) covered with a lid and incubated at 35° C. and 205 cpm for 24 h in a Synergy H1 microplate reader (Biotek Instruments Inc., Winooski, VT). The cell cultures were serially diluted and then plated on PI Agar (PIA; BD Biosciences, San Jose, CA) plates for enumeration of viable cells (CFU/mL). The % growth was calculated from the ratio $CFU/mL_{(treated)}/CFU/mL_{(untreated\ control)}$. To calculate the $IC_{50}$ values, the % growth was plotted as a function of compound concentration, expressed as log[compound] (μM), and fitted to the 4-parameter logistic model describing the sigmoid-shaped response pattern (equation 1),[83] where b is the slope factor, max is the upper asymptote (plateau), and min is the lower asymptote. Values are the average and standard deviation from three independent experiments.

$$\% \text{ growth} = \min + \frac{\max - \min}{1 + 10^{(\log IC_{50} - x) \cdot b}} \quad \text{(Eq 1)}$$

TABLE 1

Structure, Binding Affinity, and $IC_{50}$ of 4-Aminoisoindoline-1,3-dione Derivatives

| Analog | Structure | $K_d$ (μM) | $IC_{50}$ (μM) | Procedure |
|---|---|---|---|---|
| 8 | 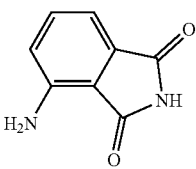 [SMILES: Nc1cccc2c1C(=O)NC2=O] | 300 ± 50 | Not active | Example 2 from WO2020117832 |
| 11 | 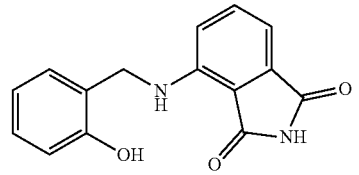 [SMILES: O=C1NC(=O)c2c(NCc3ccccc3O)cccc21] | 11 ± 1 | 258 ± 23 | Example 2 from WO2020117832 |
| KM-5-29 | 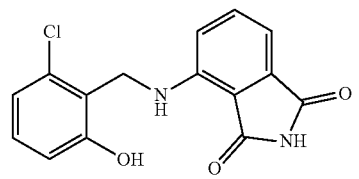 [SMILES: O=C1NC(=O)c2c(NCc3c(O)cccc3Cl)cccc21] | 6 ± 0.5 | * | Example 2 |
| JAG-5-7 | 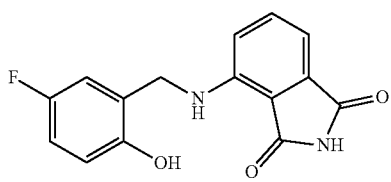 [SMILES: O=C1NC(=O)c2c(NCc3cc(F)ccc3O)cccc21] | 7 ± 2 | 128 ± 26 | Example 2 |

TABLE 1-continued

Structure, Binding Affinity, and IC$_{50}$ of 4-Aminoisoindoline-1,3-dione Derivatives

| Analog | Structure | K$_d$ (μM) | IC$_{50}$ (μM) | Procedure |
|---|---|---|---|---|
| KM-5-25 | 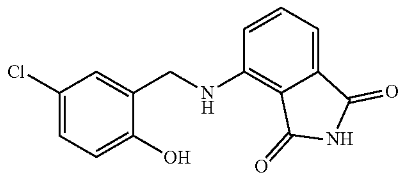 [SMILES: O=C1NC(=O)c2c(NCc3cc(Cl)ccc3O)cccc21] | 4 ± 0.6 | 69 ± 7 | Example 2 |
| KM-5-30 | 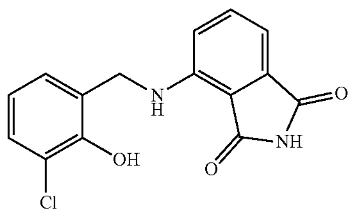 [SMILES: O=C1NC(=O)c2c(NCc3cccc(Cl)c3O)cccc21] | 6 ± 1 | 156 ± 30 | Example 2 |
| 12 (aka BN-XIV-53) | 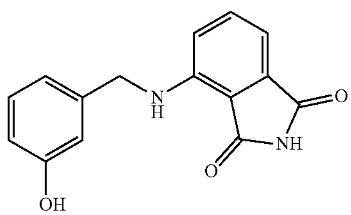 [SMILES: O=C1NC(=O)c2c(NCc3cccc(O)c3)cccc21] | 21 ± 3 | Not active at 120 μM | Example 2 |
| KM-5-50 | 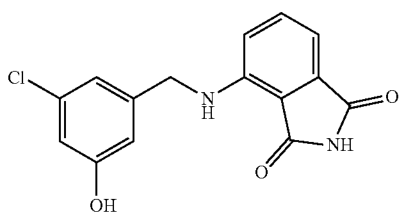 [SMILES: O=C1NC(=O)c2c(NCc3cc(O)cc(Cl)c3)cccc21] | 11 ± 2 | 82 ± 16 | Example 2 |
| KM-5-28 | 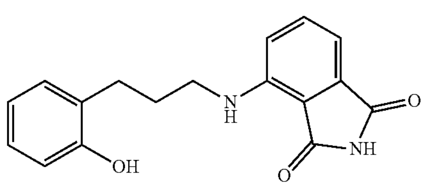 [SMILES: O=C1NC(=O)c2c(NCCCc3ccccc3O)cccc21] | 1.4 ± 0.2 | 96 ± 1 | Example 2 |
| JAG-5-6 (aka JAG-005-006) | 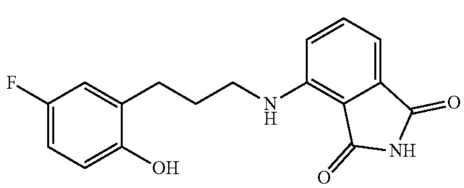 [SMILES: O=C1NC(=O)c2c(NCCCc3cc(F)ccc3O)cccc21] | 0.43 ± 0.07 | 54 ± 9 | Example 2 |
| KM-5-54 | 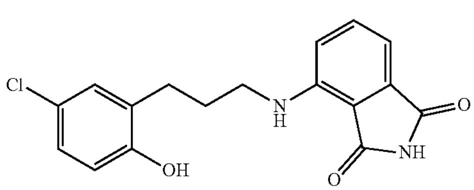 [SMILES: O=C1NC(=O)c2c(NCCCc3cc(Cl)ccc3O)cccc21] | 0.22 ± 0.04 | * | Example 2 |

TABLE 1-continued

Structure, Binding Affinity, and IC$_{50}$ of 4-Aminoisoindoline-1,3-dione Derivatives

| Analog | Structure | K$_d$ (µM) | IC$_{50}$ (µM) | Procedure |
|---|---|---|---|---|
| 16 | 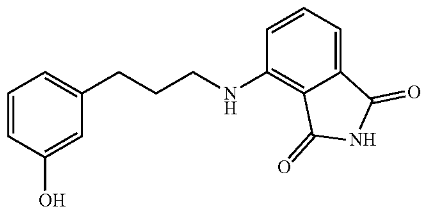 [SMILES: O=C1NC(=O)c2c(NCCCc3cccc(O)c3)cccc21] | 1.50 ± 0.25 | 121 ± 4 | Example 2 from WO2020117832 |
| KM-5-57 | 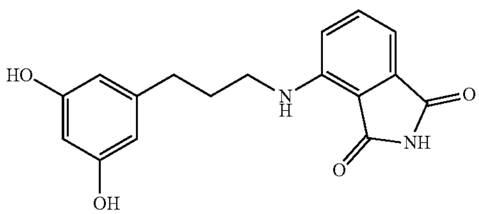 [SMILES: O=C1NC(=O)c2c(NCCCc3cc(O)cc(O)c3)cccc21] | 2.5 ± 0.4 | Not active at 200 µM | Example 2 |
| KM-5-66 | 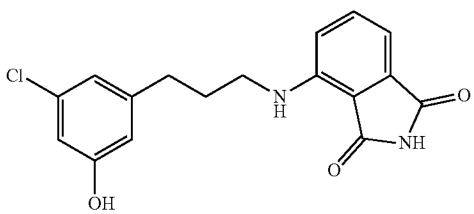 [SMILES: O=C1NC(=O)c2c(NCCCc3cc(O)cc(Cl)c3)cccc21] | 0.35 ± 0.05 | 42 ± 6 | Example 2 |

*Not determined because of low solubility (<30 µM) in PBS buffer.

Prior to testing the effect that the 4-substituted isoindoline-1,3-dione derivatives might exert on *P. aeruginosa* cells, the strength of their interaction with BfrB was evaluated in vitro with a fluorescence polarization assay developed based on the intrinsic fluorescence of the isoindoline-1,3-dione moiety. Because initial fluorescence spectroscopic measurements revealed that the heme groups in BfrB interfere with the signal of the fluorescent ligand, apo-BfrB was utilized for these measurements, capitalizing on earlier findings that the Bfd-binding sites in apo-BfrB are nearly identical to those in BfrB, and that the K$_d$ for the interaction between apo-BfrB and Bfd is very similar to that measured for the interaction between BfrB and Bfd. Hence, the K$_d$ values were measured by titrating apo-BfrB into a fixed concentration of the appropriate fluorescent 4-aminoisoindoline-1,3-dione ligand while analyzing fluorescence polarization and intensity near the emission $\lambda_{max}$.

Analysis of Secreted Pyoverdine in Planktonic Cultures

These experiments were conducted in 96-well plates as described above for the determination of IC$_{50}$, except that the cells were cultured in M63 media (2 g/L (NH$_4$)$_2$SO$_4$, 13.6 g/L KH$_2$PO$_4$ (Sigma-Adlrich, St. Louis, MO), 2 g/L glucose, 4 g/L citric acid, 5 g/L technical grade casamino acids (BD Biosciences, San Jose, CA), 0.24 g/L MgSO$_4$ (Alfa Aesar, Haverhill, MA), and 0.05% (w/v) HPMC, pH 7.0 adjusted with KOH). Cultures of *P. aeruginosa* PAO1 treated with KM-5-25 (70 µM) or KM-5-66 (50 µM) were grown for 27 h prior to diluting the contents of each well in PBS (pH 7.4) and plating the cells on PIA plates for enumeration of CFU/mL. The 500-fold diluted solution was clarified by centrifugation and the pyoverdine in the cell-free supernatant was analyzed by acquiring fluorescence emission spectra (430-550 nm) with excitation at 400 nm (10 nm slit width) and emission at $\lambda_{max}$=460 nm (10 nm slit width) using a Perkin Elmer LS50B spectrophotometer.

Flow Cell Biofilm Assays

Surface-attached biofilms of *P. aeruginosa* PAO1 cells expressing EYFP were grown on flow cells with an 800 µm channel depth (µ-slide I$^{0.8}$ Luer, Ibidi) using an automated perfusion system (Ibidi, Munich, Germany), as described in Soldano, A.; Yao, H.; Chandler, J. R.; Rivera, M. (2020) Inhibiting Iron Mobilization from Bacterioferritin in *Pseudomonas aeruginosa* Impairs Biofilm Formation Irrespective of Environmental Iron Availability. *ACS Infect. Dis.* 6, 447-458. 10.1021/acsinfecdis.9b00398.[26] Briefly, the flow cell was inoculated with 200 µL of an overnight culture diluted to OD$_{600}$=0.5, followed by 1 h incubation at 30° C. to allow bacterial cell attachment. The ρ-slide was connected to the Ibidi Pump System and the biofilms were cultured for 3 days at 30° C. while flowing AB minimal media containing 15 µM Fe. The experimental shear stress was 0.14-dyn/cm$^2$ (shear rate=14 s$^{-1}$, pressure=7.1 mbar, flow rate=0.4 mL/min) and the switch time was set to 540 s. The biofilms were treated for 24 hours by flowing AB minimal media supplemented with 15 µM Fe, 0.025% HPMC, 1.5% DMSO and commercial antibiotics or 4-aminoisoindoline-1,3-dione derivatives in the concentrations indicated in the corresponding figure captions. During biofilm growth and challenge with antibacterial, the culture medium in the reservoirs was removed every 12 hours and replaced with fresh pre-warmed medium. Prior to imaging with the aid of CLSM the biofilms were stained with 4 mL of 2.5 nM Sytox Red (Invitrogen, Carlsbad, CA), a cell impermeable fluorescent nucleic acid dye that stains dead cells and extracellular DNA,[84] for 20 min (switch time=200 sec) and then washed with AB media for 20 min to remove excess fluorescent dye. The biofilms were imaged with the aid of a Leica TCS SP8 confocal microscope (Leica Microsystems, Germany) using a HC PL apo CS2 63×/1.4 oil objective. For detecting the EYFP fluorescence the laser line was set at 506 nm and the emission range to 520-610 nm. Sytox Red fluorescence was detected with excitation at 631 nm and emission range 637-779 nm. Image stacks were acquired with a z-step size of 0.3 μm at randomly chosen positions. The Leica Application Suite X (LAS-X) software was used for image stack processing.[54] Quantitative analysis of biofilm biomass was performed using the COMSTAT computer program[54] and the Otsu method of automatic thresholding.[85]

Pellicle Biofilm Assays

Pellicle biofilms of EYFP-expressing *P. aeruginosa* PAO1 or clinical isolates were grown in PI media supplemented with 20 μM Fe. Starter cultures were diluted to $OD_{600}$=0.001 in 4 mL media, placed in 35×10 mm petri dishes and incubated statically at 30° C. for 48 hours. The pellicles were transferred onto circular (1.5 cm diameter) glass coverslips by gently allowing the surface of a coverslip to contact a pellicle. The pellicle-adhered coverslip was washed in PBS and then deposited on top of 1.5 mL of AB challenge media contained in a well of a 12-well microplate, with the pellicle exposed to the media. Challenge media consists of AB minimal media supplemented with 15 μM Fe, 0.025% HPMC, 1.5% DMSO and commercial antibiotic or 4-aminoisoindoline-1,3-dione derivative, used in the concentrations specified in the figure captions. The 4-aminoisoindoline-1,3-dione derivatives were prepared as 10 mM stock solutions in DMSO and then diluted in culture media to the appropriate concentrations. The coverslip-adhered pellicles were exposed to challenge media at 30° C. for 24 hours, changing the challenge media every 12 hours by transferring the pellicle-adhered coverslip to a new plate containing pre-warmed challenge media.

Prior to imaging with the aid of CLSM, pellicles formed by EYFP-expressing PAO1 cells were washed with PBS and then stained by placing the coverslip-adhered pellicles in 1 mL of PBS containing 2.5 nM Sytox Red (20 min). Excess fluorescent dye was washed with PBS, the coverslip was mounted on a glass slide using 5 μL of SlowFade (Invitrogen, Carlsbad, CA) and the edges sealed with fingernail polish. CLSM image stacks (z-step size of 0.3 μm) were acquired with the aid of a Leica TCS SP8 microscope, as described above. Quantitative analysis was performed by determination of pellicle biomass using COMSTAT[54] and the Otsu method of automatic thresholding.[85]

Determination of Viable Cells in Pellicle Biofilms

Pellicle biofilms were grown as described above. Planktonic and loosely attached cells were washed (3 times) by immersing the coverslip-adhered pellicles (biofilm facing up) into a well of a 12-well plate containing 3 mL of PBS, and incubating (5 min) with gentle rocking. To remove the pellicle from the coverslip, break the extracellular matrix and release cells from the biofilm, the coverslip-adhered pellicle was placed in a 50 mL conical tube containing a 2 mL suspension of zirconia beads (0.1 mm diameter, BioSpec Products), 10 mL PBS, 0.2 μg/mL alginate lyase and 0.2 μg/mL DNAse. The resultant mixture was incubated at room temperature for 3 min, followed by vigorous vortexing for 4 min. After sedimentation of the zirconia beads, a 100 μL aliquot was used for serial dilution and plating on PIA plates for subsequent enumeration of viable cells (CFU/mL).

Imaging of Iron Stored in BfrB and Analysis of Total Intracellular Iron in Biofilm-Embedded Cells Pellicle biofilms were grown for 48 hours as described above. The pellicles were transferred onto square (2 cm×2 cm) glass coverslips by gently contacting the pellicle with the coverslip. The pellicle-adhered coverslip was washed in PBS and then placed in a 50 mL conical tube containing 2 mL suspension of zirconia beads, 15 mL PBS, 0.2 μg/mL alginate lyase and 0.2 μg/mL DNAse; the resultant mixture was incubated (3 min) at room temperature, and then vortexed vigorously for 4 min. After the zirconia beads had sedimented, a 100 μL aliquot was sampled from the cell suspension for plating and enumeration of viable cells and a 14 mL sample was used to harvest the cells by centrifugation (20 min, 400 rpm). The cell pellet was resuspended in 1 mL of PBS, transferred to a 1.5 mL microcentrifuge tube, centrifuged for 10 min at 12,500 rpm at 4° C. and the cell pellet frozen at −80° C. The frozen cells were subjected to three freeze-thaw cycles and then lysed by addition of 200 μL of lysis buffer (50 mM Tris-HCl buffer (pH 8.0) containing 10% (v/v) glycerol, 20 mg/mL lysozyme, 0.2 mg/mL DNAse, 0.1 M NaCl, 1 mM $MgSO_4$ and 1% (v/v) Triton-X100) and incubated at ambient temperature (30 min) and at 37° C. (30 min). Imaging of iron in BfrB was carried out as previously reported:[23] lysate suspensions were clarified by centrifugation (10 min at 12,500 rpm), mixed with 10 μL of loading dye (5.9 mL deionized water, 0.5 mL glycerol, 0.4 mL β-mercaptoethanol, 0.4 mL 1% (w/v) bromophenol blue, and 0.5 mL 1 M Tris-HCl (pH 6.8), and loaded onto 1.5 mm-thick native PAGE gels (4% stacking gel, 8% resolving gel). Electrophoresis was carried out at 60 V and 4° C. for 9 hours, and the gels were stained in the dark by immersion (10 min) in a solution containing 0.049 g Ferene S, 250 μL thioglycolic acid, 2.4 mL acetic acid and 100 mL deionized water. Levels of total intracellular iron were determined as reported previously:[23, 86] the cell pellets were treated with 500 μL of freshly prepared digestion reagent (0.6 N HCl, 2.25% (w/v) $KMnO_4$ in water), thoroughly mixed by vortexing, and then incubated at 65° C. for 3.5 hours. The resultant solutions were cooled to ambient temperature, treated with 100 μL of iron detection reagent (6.5 mM Ferene S, 15.4 mM neocuproine, 2 M ascorbic acid, and 5 M ammonium acetate), incubated for 30 min at ambient temperature and centrifuged for 5 min at 12,500 rpm. The iron concentration was measured from the absorbance of the $Fe^{2+}$-Ferene S complex ($\varepsilon_{593}$=34.5 $mM^{-1}$ $cm^{-1}$),[87] normalized by the viable cell counts and reported as Fe atoms per cell.

Statistical Analysis

Statistical significance between the means and standard deviation of values obtained in experiments comparing results from untreated vs. treated with antibiotic or analog conditions was determined using one-way ANOVA followed by Tukey's multiple post hoc test, with the aid of SigmaPlot (Systat Software, Inc., CA).

Example 3: 4-Aminoisoindoline-1,3-dione Derivatives Elicit a Bacteriostatic Effect in Planktonic *P. aeruginosa* Cultures The relative strength of the association between the new analogs and BfrB was evaluated measuring the dissociation constant $K_d$ (Table 1). The results show that installing a halogen atom in the phenyl ring improves the binding affinity of the derivatives relative to the previously reported analogs 11 and 16. The $K_d$ values of halogen containing compounds with a —($CH_2$)— linker are on average ~2-fold lower when compared to the $K_d$ exhibited by 11, and the $K_d$ values of halogen-bearing analogs with a —($CH_2$)$_3$— linker are on average ~5-fold lower than the $K_d$ measured for analog 16. The relative efficacy of the analogs to inhibit *P. aeruginosa* planktonic growth was evaluated by measuring the half maximal inhibitory concentration ($IC_{50}$). Inspection of the data in Table 1 shows that all the halogenated compounds are more active than analogs 11 and 16. The activity of KM-5-29 and KM-5-54 could not be evaluated because the relatively low aqueous solubility of these compounds prevented measurement of their $IC_{50}$ values.

Although the compounds synthesized so far do not include all possible substitution isomers, some insights of the governing structure activity relationships have begun to emerge (Table 1): (i) Among the compounds with a —(CH$_2$)— linker, the data reveal that when the hydroxyl group is at position 2 relative to the linker (KM-5-29, JAG-5-7, KM-5-25 and KM-5-30) a bulkier Cl atom at position 5 (KM-5-25) imparts ~2-fold higher binding affinity for BfrB than a smaller F atom at the same position (JAG-5-7). In line with the nearly 2-fold lower $K_d$, the $IC_{50}$ of KM-5-25 is ~2-fold lower than that of JAG-5-7. In comparison, a Cl atom at position 3 (KM-5-30) imparts a $K_d$ similar that of KM-5-25, but an $IC_{50}$~2.5-fold larger, suggesting that KM-5-30 is less efficient at penetrating or accumulating in *P. aeruginosa* cells. Installing a Cl atom at position 6 (KM-5-29) renders the compound poorly soluble in aqueous solution. It is also interesting to compare the two analogs with a hydroxyl group at position 3. The presence of a Cl atom at position 5, KM-5-50, lowers the $K_d$ by a factor of 2 relative to BN-XIV-53 and improves the activity vs. planktonic cells significantly, (ii) Examining the compound series with a —(CH$_2$)$_3$— linker shows that when the hydroxyl group is at position 3, a Cl atom at position 5 (KM-5-66) decreases the $K_d$~4-fold and the $IC_{50}$~3-fold relative to compound 16. In comparison, the presence of a second hydroxyl group at position 5 (KM-5-57) increases the $K_d$~1.7-fold relative to 16 and renders the compound inactive. Given that the $K_d$ measured for KM-5-57 is similar or lower than $K_d$ values measured for other active compounds in Table 1, the immeasurable activity of KM-5-57 suggests that it cannot penetrate or accumulate in *P. aeruginosa* cells, (in) Comparison of compounds where the hydroxyl group is at position 2 (KM-5-28, JAG-5-6 and KM-5-54) also shows that a halogen at position 5 improves binding affinity. A bulkier Cl atom at position 5 increases the binding affinity of KM-5-54 2-fold relative to the compound with a F at the same position (JAG-5-6). Comparing the $IC_{50}$ values corresponding to KM-5-28 and JAG-5-6 reveals that the ~3-fold lowered caused by installing a F atom at position 5 is accompanied by ~2-fold decrease in the $IC_{50}$. Attempts to determine whether the lower $K_d$ obtained when a Cl atom at position 5 would bring an additional decrease in the $IC_{50}$ were stymied by the poor water solubility of KM-5-54.

The structure-activity relationships (SAR) information available thus far indicates that a halogen in the aryl ring of the 4-aminoisoindoline-1,3-dione derivatives invariably improves binding affinity for BfrB. In compounds with a —(CH$_2$)— linker, when the hydroxyl group is at position 2, a Cl atom at position 5 imparts favorable properties, a Cl atom at position 3 renders the compound poorly active vs. *P. aeruginosa*, despite a relatively favorable $K_d$, and a Cl atom at position 6 imparts poor aqueous solubility. The preparation of compounds with a —(CH$_2$)$_3$— linker is more elaborate and accessibility to suitable starting materials at reasonable prices is also more limited. The information available thus far indicates that although a Cl at position 5 is favorable whether the hydroxyl group is at position 2 or 3, poor aqueous solubility impairs the potential biological activity when the hydroxyl is at position 2 (KM-5-54), despite having the most favorable $K_d$ of all compounds in Table 1. Attempts to increase aqueous solubility by installing a hydroxyl group at position 5 succeeded in increasing solubility but rendered a compound (KM-5-57) with lower affinity for BfrB and inactive against *P. aeruginosa* cells. As new compounds become available, similar evaluation of binding affinity and activity against bacterial cells will continue to shed light on the structural requirements that simultaneously enhance target affinity in vitro and activity against *P. aeruginosa* cells. For the purposes of the studies described below, we chose to work with compounds KM-5-25, the most active of the analogs containing a —(CH$_2$)— linker, and KM-5-66, the most active of the analogs harboring a —(CH$_2$)$_3$— linker.

Figure 11:
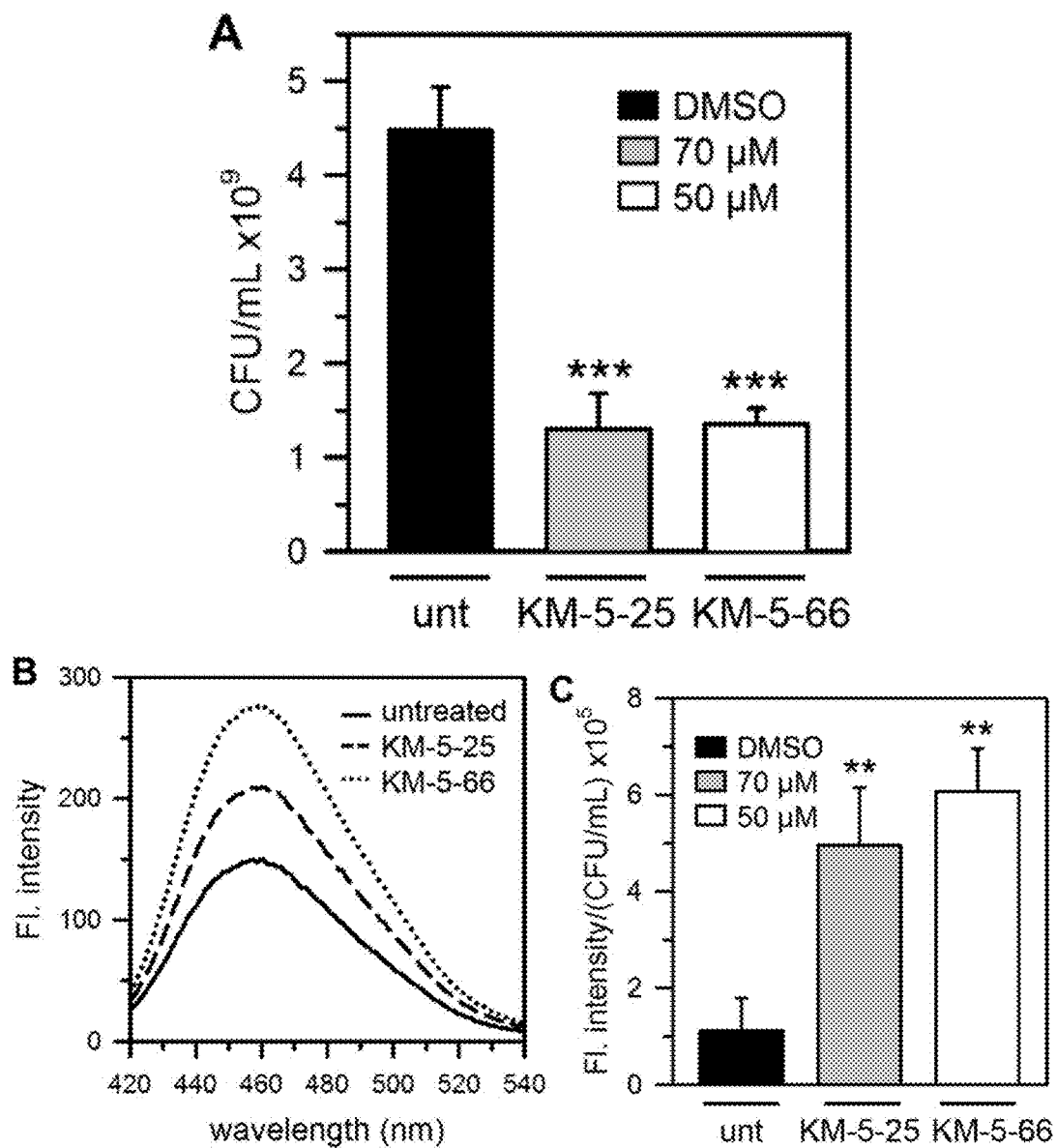
FIG. 11 shows that P. aeruginosa cells treated 4-aminoisoindoline-1,3-dione derivatives overproduce pyoverdine. (A) shows that P. aeruginosa cultures treated with KM-5-25 (70 µM) or KM-5-66 (50 µM) for 27 h have ~35% of the viable cells in the untreated control. (B) shows fluorescence spectra from cell-free supernatant corresponding to untreated cultures (solid line), treated with KM-5-25 (dashed line), or treated with KM-5-66 (dotted line). (C) shows fluorescence intensity normalized to the number of viable cells (CFU/mL), demonstrating that cells treated with KM-5-25 or KM-5-66 secrete significantly more pyoverdine than cells in the untreated control. Averages and standard deviations for 3 biological replicates are shown, p<0.01 denoted by  and p<0.001 by * relative to untreated.

Example 4: Planktonic *P. aeruginosa* Cells Treated with 4-Aminoisoindoline-1,3-Dione Derivatives Overproduce Pyoverdine Previous studies directed at evaluating the repercussions of blocking the BfrB-Bfd complex in *P. aeruginosa* cells relied on deleting the bfd gene (Δbfd). These investigations showed that blockade of the BfrB-Bfd complex in planktonic Δbfd cells causes an irreversible accumulation of iron in BfrB and iron deficiency in the cytosol. The resultant phenotype is hyperproduction of pyoverdine relative to the wild type cells.[23] Pyoverdine is a siderophore produced by *P. aeruginosa* when the cells experience iron limitation.[39] A similar pyoverdine overproduction phenotype was observed when wild type *P. aeruginosa* cells were treated with small molecule inhibitors of the BfrB-Bfd complex (11 and 16).[25] Therefore, to determine that compounds KM-5-25 and KM-5-66 inhibit iron mobilization from BfrB in the *P. aeruginosa* cytosol, whether cells treated with these compounds express the characteristic pyoverdine hyperproduction phenotype was investigated. To this end, planktonic cells were cultured in the presence of KM-5-25 (70 µM) or KM-5-66 (50 µM) for 27 h in M63 media and the content of the secreted pyoverdine in the cell-free spent media was analyzed by measuring the fluorescence intensity at 460 nm. Normalizing the intensity of pyoverdine fluorescence to CFU/mL shows that as expected, cells treated with KM-5-25 or KM-5-66 secrete~ 5-fold more pyoverdine than the untreated control (FIGS. 11(A-C)), an overproduction level similar to that observed with the Δbfd mutant.[23] These observations indicate that both analogs bind BfrB in the *P. aeruginosa* cytosol, block the BfrB-Bfd interaction and inhibit iron mobilization from BfrB, resulting in cytosolic iron limitation that is manifested in a pyoverdine hyperproduction phenotype. The cytosolic iron limitation caused by treating planktonic cultures with KM-5-25 or KM-5-66 exerts a bacteriostatic effect on the cells, as indicated by the $IC_{50}$ values in Table 1. In stark contrast, when the same compounds are used to treat *P. aeruginosa* biofilms, a bactericidal effect is observed. The results from these experiments are further described and discussed in the following examples.

Example 5: 4-Aminoisoindoline-1,3-Dione Derivatives Kill *P. aeruginosa* Cells in Mature Biofilms The susceptibility of mature biofilms to treatment with analogs of 4-aminoisoindoline 1,3-dione was tested using two platforms, biofilms cultured at the solid-liquid interface (flow cell biofilms) and biofilms cultured at the air-liquid interface (pellicles). Biofilms of *P. aeruginosa* cells expressing an enhanced yellow fluorescent protein (EYFP) were cultured in flow cells using AB minimal media supplemented with 15 µM Fe. 3-Day old biofilms were treated for 24 h with commercial antibiotics or with 4-aminoisoindoline-1,3-dione analogs by flowing AB media containing analog or commercial antibiotic, 0.025% hypromellose (HPMC), 1.5% DMSO and 15 µM Fe. In most experiments, the concentration of commercial antibiotics used was 25× or 50× the MIC, and the concentration of 4-aminoisoindoline-1,3-dione analogs was between 0.36× and 1.2× the $IC_{50}$. The treated biofilms were counterstained with the cell impermeable fluorescent nucleic acid dye Sytox Red and then imaged with the aid of confocal laser scanning microscopy (CLSM). FIG. 1(A) depicts a representative image of the untreated control, illustrating yellow-fluorescent viable cells and red-stained dead cells and extracellular DNA. FIGS. 1(B-C) show representative images depicting 4-day old biofilms tolerant to 24 h treatment with ciprofloxacin or tobramycin, respectively, and FIG. 1(D) shows 4-day old biofilms susceptible to 24 hours treatment with colistin. In agreement to previously reported observations,[48, 53] treatment with ciprofloxacin preferentially treats cells at the biofilm surface, leaving the interior of the biofilm almost unaffected (FIG. 1(B)). In contrast, treatment with colistin preferentially treats bacteria in the biofilm interior, leaving the biofilm surface less affected (FIG. 1(D)). COMSTAT software was used to attempt a quantitative comparison of the biofilm biomass by estimating the biovolume, which is calculated as the overall volume/substratum area ($µm^3/µm^2$).[54] Comparing the biofilm biomass as the ratio of (untreated biomass)/(treated biomass) expressed as % survival (FIG. 1(E)) shows that ~20% of biomass remains viable (yellow fluorescent) after treatment with colistin at 25× the MIC. In comparison, ~60% and 70% of biomass remains viable after treatment with 25× the MIC ciprofloxacin or tobramycin, respectively.

Figure 2:
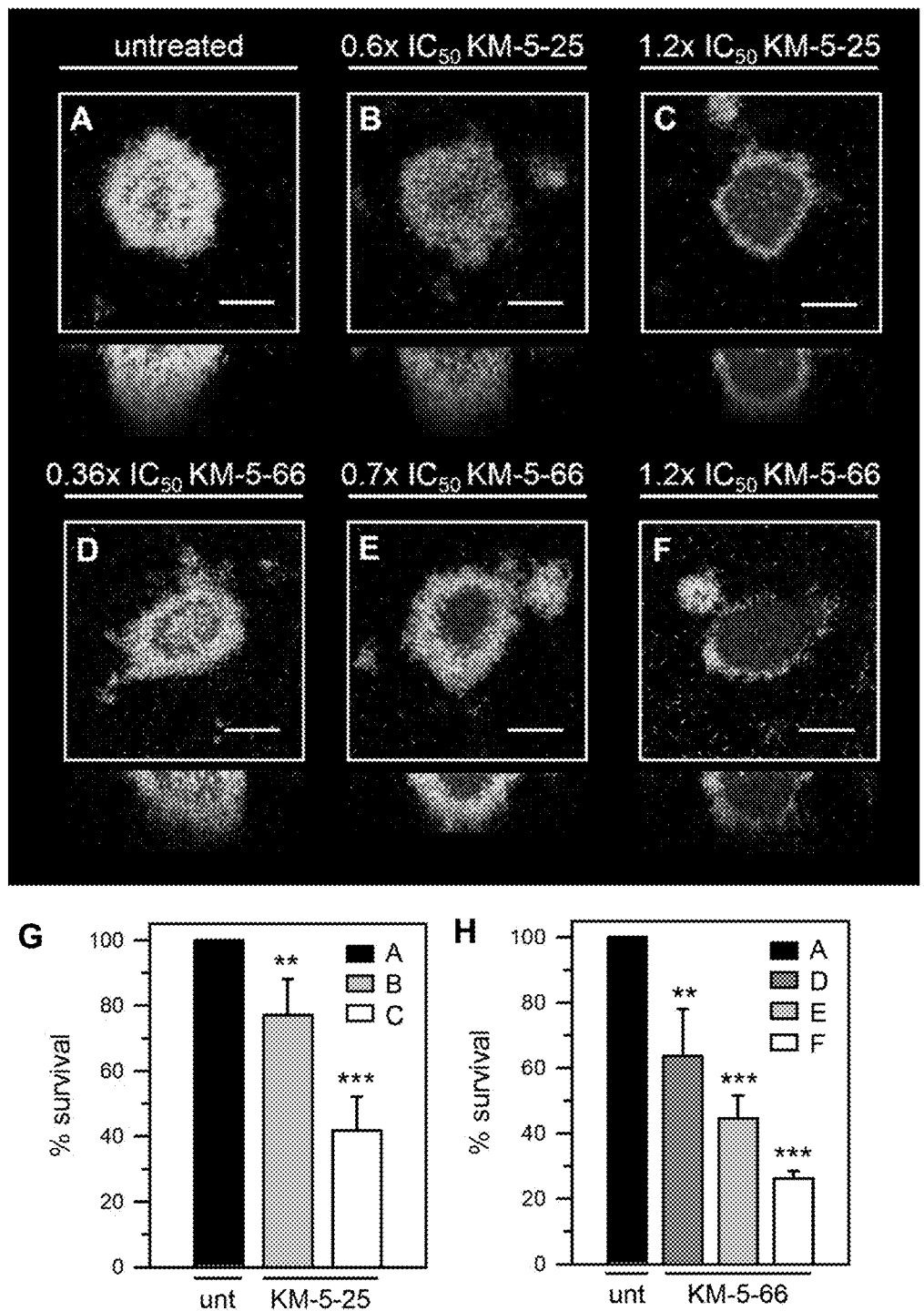
FIG. 2 shows that *P. aeruginosa* cells embedded in mature biofilms grown in flow cells are susceptible to 4-aminoisoindoline-1,3-dione analogs. EYFP-expressing *P. aeruginosa* PAO1 biofilms were cultured for three days by flowing AB media supplemented with 15 µM Fe and then treated for 24 h with 4-aminoisoindoline-1,3-dione analog. Biofilms were counterstained with Sytox Red and imaged with the aid of CLSM. Top-down views (x-y plane) are depicted with side views (x-z plane) at the bottom. Viable cell mass is in yellow and dead cells and extracellular DNA in red. (A) shows the untreated (DMSO) control. (B) shows treatment at 0.6× the $IC_{50}$ of KM-5-25 (40 µM). (C) shows treatment at 1.2× the $IC_{50}$ of KM-5-25 (80 µM). (D) shows treatment at 0.36× the $IC_{50}$ of KM-5-66 (15 µM). (E) shows treatment at 0.7× the $IC_{50}$ of KM-5-66 (30 µM). (F) shows treatment at 1.2× the $IC_{50}$ of KM-5-66 (50 µM). (G) shows the % survival obtained from viable biomass calculated with the aid of COMSTAT software for cells treated with KM-5-25. (H) shows the % survival obtained from viable biomass calculated with the aid of COMSTAT software for cells treated with KM-5-66. The scale of the bars represents 20 µm. $p<0.01$ denoted by  and $p<0.001$ by * relative to untreated.

With the establishment that the biofilms are susceptible to colistin and significantly tolerant to ciprofloxacin and tobramycin, similarly cultured 3-day old biofilms were treated with KM-5-25 and KM-5-66 for 24 hours. Compounds KM-5-25 and KM-5-66 are soluble in aqueous media to ~110 µM and ~80 µM, respectively. To ensure that the compounds remain soluble during the 24 h treatment period, KM-5-25 was used at concentrations 40 µM and 80 µM, equivalent to 0.6× and 1.2× the $IC_{50}$, and KM-5-66 was used at concentrations 15 µM, 30 µM and 50 µM, equivalent to 0.36×, 0.7× and 1.2× the $IC_{50}$ Table 1 insert back on p 36). Representative CLSM images obtained after treating 3-day old biofilms with each of the analogs for 24 hours show that both compounds treat biofilm cells in a concentration dependent manner (FIGS. 2(A-F)). Treatment with 50 µM KM-5-66 elicits a similar level of treating as treatment with 80 µM KM-5-25. The higher efficacy exhibited by KM-5-66 agrees with its higher binding affinity for BfrB and lower $IC_{50}$. Inspection of the images obtained upon treatment with the higher concentrations of KM-5-25 or KM-5-66 clearly shows that the inhibitors of the BfrB-Bfd complex treat the cells in the interior of the biofilm, leaving most of the viable cells located at the biofilm surface (FIGS. 2(C, F-H)). This pattern of treating is reminiscent of previously reported observations showing that treatment of biofilms with $Ga^{3+}$ preferentially treats cells in the inner portion of the biofilm.[55] The same authors concluded that cells in the biofilm interior are more sensitive to $Ga^{3+}$ because this population experiences a more pronounced iron starvation. Therefore, without being bound by theory, it is speculated that in biofilms treated with KM-5-25 or KM-5-66 the internal biofilm population is more susceptible to iron limitation caused by the nearly irreversible accumulation of iron in BfrB. It is important to underscore that although the mechanisms whereby iron starvation contribute to cell death in the biofilm interior are not yet understood, the fact remains that perturbation of iron homeostasis, either by systemic replacement of $Fe^{3+}$ with $Ga^{3+}$, or by selective inhibition of the BfrB-Bfd complex, leads to bacterial cell death.

Figure 3:
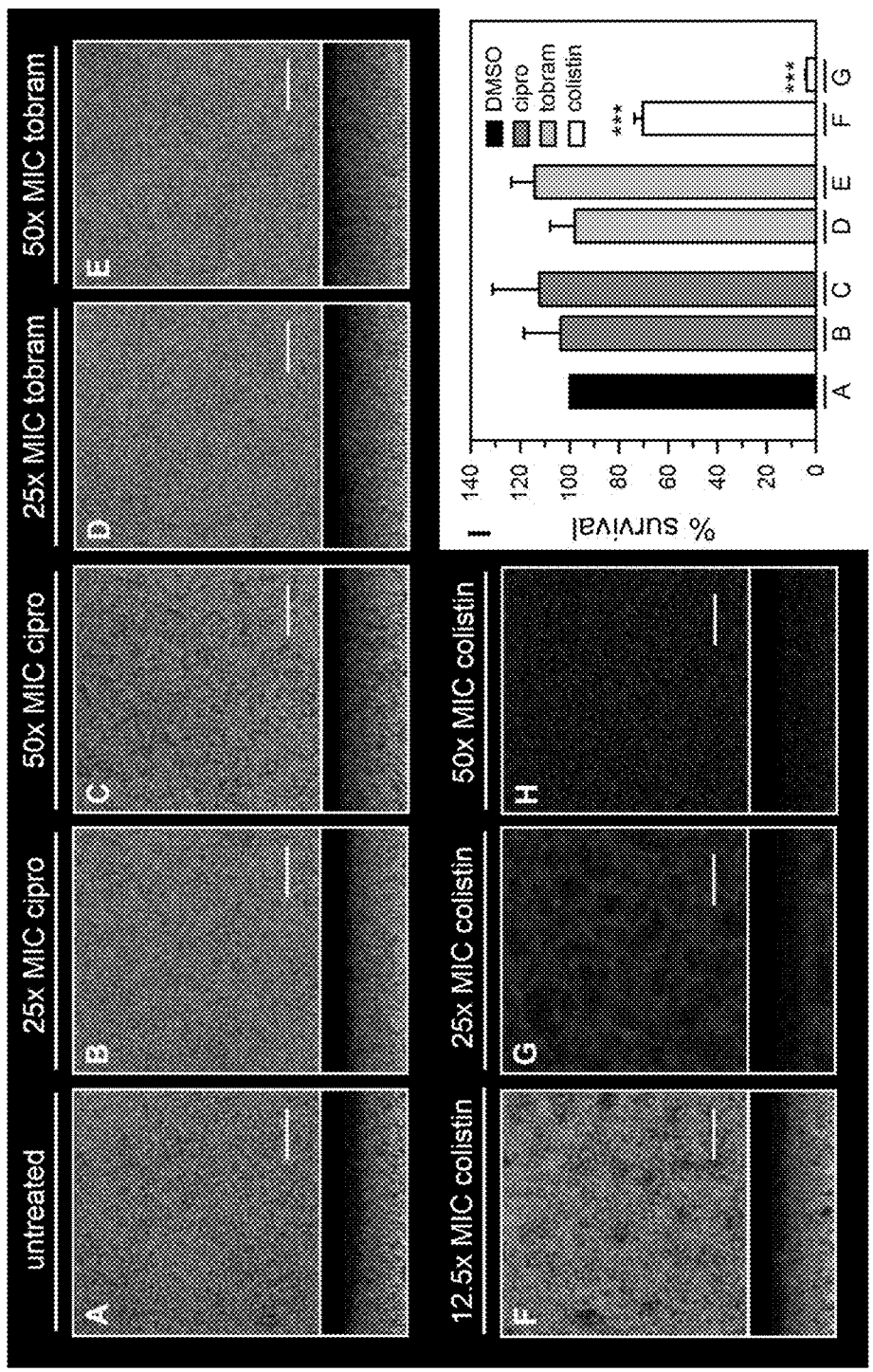
FIG. 3 shows that pellicle biofilms are tolerant to ciprofloxacin and tobramycin, and susceptible to colistin. Pellicles of *P. aeruginosa* PAO1 expressing EYFP were cultured in PI media supplemented with 20 µM Fe for 48 h, and then treated with antibiotics for 24 h. Pellicles were counterstained with Sytox Red and imaged with the aid of CLSM. Images depict top-down views (squares) and side views (rectangles) where viable cells are shown in yellow and dead cells and extracellular DNA in red. (A) shows the untreated (DMSO) control. (B) shows treatment at 25× the MIC of ciprofloxacin (19 µM). (C) shows treatment at 50×MIC ciprofloxacin (38 µM). (D) shows treatment at 25× the MIC of tobramycin (27 µM). (E) shows treatment at 50× the MIC of tobramycin (54 µM). (F) shows treatment at 12.5× the MIC of colistin (10 µM). (G) shows treatment at 25× the MIC of colistin (20 µM). (H) shows treatment at 50× the MIC of colistin (40 µM), (I) shows % survival obtained from viable biomass calculated with the aid of COMSTAT software. The scale of the bars represents 20 µm. $p<0.001$ denoted by *** relative to untreated.
Figure 4:
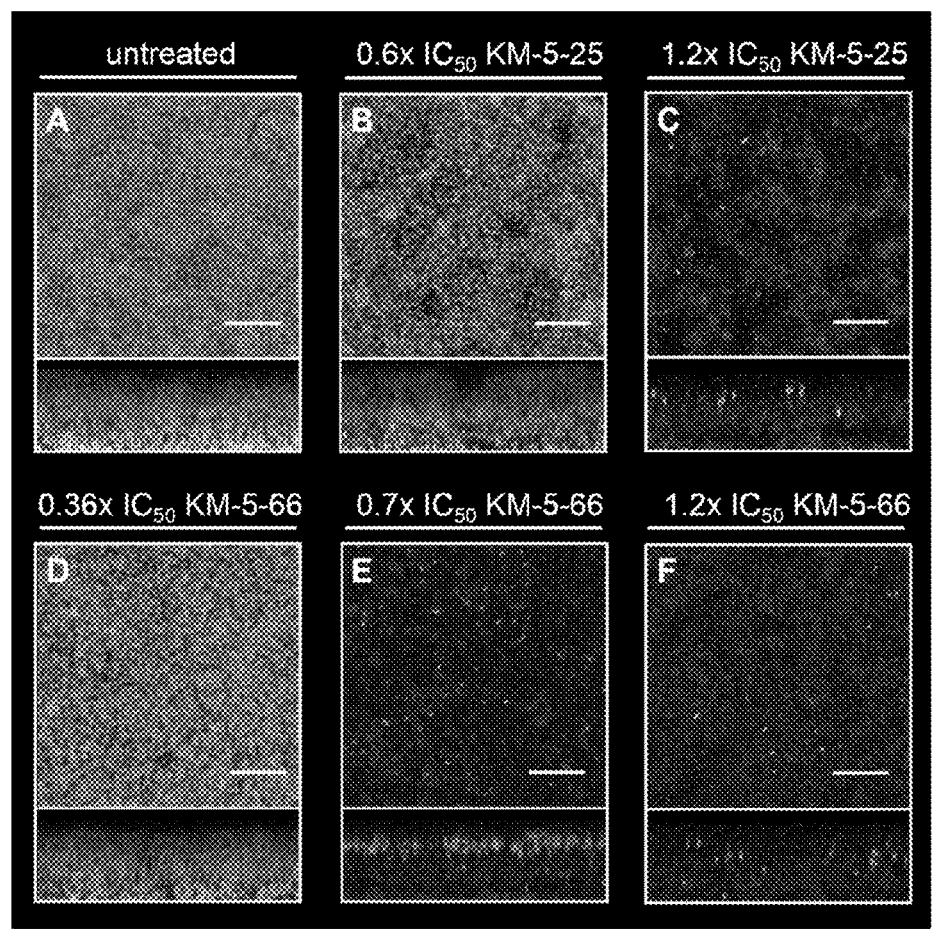
FIG. 4 shows that 4-aminoisoindoline-1,3-dione analogs kill *P. aeruginosa* cells embedded in pellicle biofilms. Pellicles of *P. aeruginosa* PAO1 cells expressing EYFP were cultured for 48 h in PI media supplemented with 20 µM Fe, and then treated with KM-5-25 or KM-5-66 for 24 h. Pellicles were counterstained with Sytox Red and imaged with the aid of CLSM. Images depict top-down views (squares) and side views (rectangles) where viable cells are shown in yellow and dead cells and extracellular DNA in red. (A) shows the untreated (DMSO) control. (B) shows treatment at 0.6× the $IC_{50}$ of KM-5-25 (40 µM). (C) shows treatment at 1.2× the $IC_{50}$ of KM-5-25 (80 µM). (D) shows treatment at 0.36× the $IC_{50}$ of KM-5-66 (15 µM). (E) shows treatment at 0.7× the $IC_{50}$ of KM-5-66 (30 µM). (F) shows treatment at 1.2× the $IC_{50}$ of KM-5-66 (50 µM). (G) shows % survival obtained from viable biomass calculated with the aid of COMSTAT software for pellicles treated with KM-5-25. (H) shows % survival obtained from viable biomass calculated with the aid of COMSTAT software for pellicles treated with KM-5-66. The scale of the bars represents 20 µm. p<0.01 denoted by  and p<0.001 by * relative to untreated.
Figure 4:
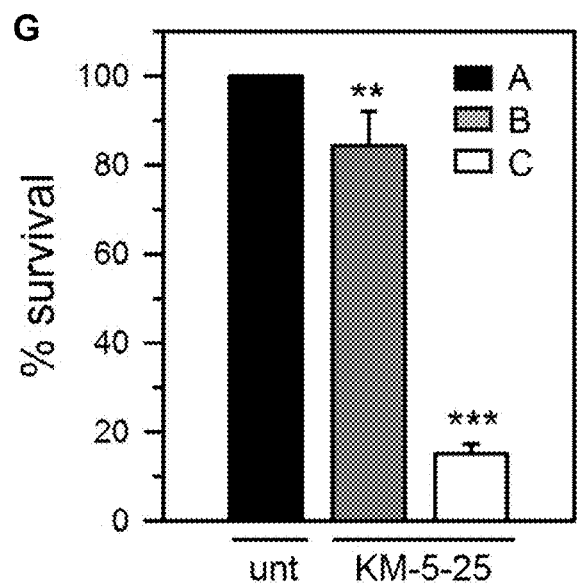
Figure 4:
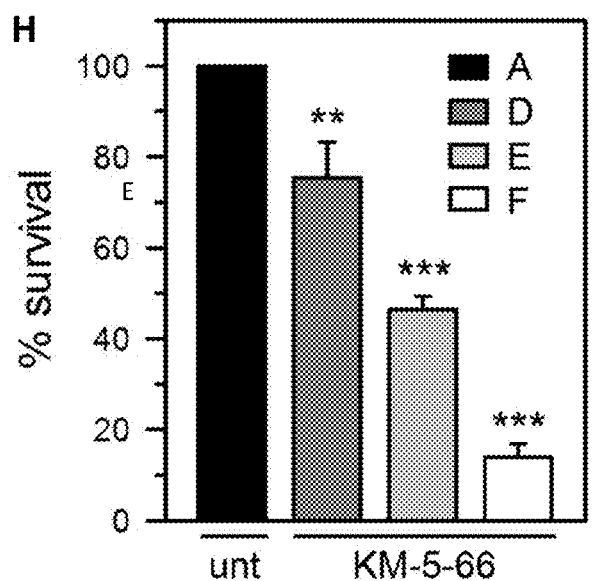

To expand the observations made with flow cell biofilms into a second biofilm model, the susceptibility of biofilms grown at the air-liquid interface (pellicles) was also studied.[56-57] Pellicle biofilms (henceforth pellicles) are an attractive alternative platform to study biofilms because pellicles are amenable to imaging by CLSM and to harvesting, which can be desirable for additional biofilm analysis.[26] To determine the susceptibility of pellicles to antibiotics or inhibitors of the BfrB-Bfd complex, 2-day old pellicles of EYFP-expressing *P. aeruginosa* cells were cultured in PI media supplemented with 20 µM Fe. The pellicles were transferred onto glass coverslips by allowing the surface of the coverslip to contact a pellicle. The coverslip-adhered pellicles were subsequently exposed to treatment solution (AB media supplemented with 15 µM Fe, 0.025% HPMC, 1.5% DMSO, and antibiotic or analog) for 24 h prior to staining with Sytox Red and imaging with the aid of CLSM. The pellicle biofilms are tolerant to ciprofloxacin and tobramycin at concentrations 25× and 50× the MIC (FIG. 3(B-E)), as is evident by the yellow fluorescence and near complete absence of red-stained dead cells. In contrast, the pellicle biofilms are susceptible to colistin at concentrations above 10× the MIC (FIG. 3(F-H)). Analysis of the images with COMSTAT, which allowed a more quantitative comparison of cell survival upon treatment with each of the antibiotics (FIG. 3(I)), confirms tolerance to ciprofloxacin and tobramycin, but sensitivity to colistin. Note that when the concentration of colistin is 50× the MIC the fluorescence signal from viable cells expressing EYFP is undetectable. When pellicle biofilms are challenged with compound KM-5-25 or KM-5-66 bacterial cell death occurs in a concentration dependent manner (FIGS. 14A-14H). These results agree with the idea that the 4-aminoisoindoline-1,3-derivatives penetrate the bacterial cell and bind to their target in the *P. aeruginosa* cytosol. Inspection of the images and analysis with COMSTAT (FIG. 4(G, H)) shows that compound KM-5-66 is more efficacious than KM-5-25, observations that are consistent with the lower $K_d$ and $IC_{50}$ values measured for KM-5-66. It is also important to note that when compounds KM-5-25 and KM-5-66 are used at a concentration of 80 µM and 50 µM, respectively (FIG. 4(G, H)), which correspond approximately to 1.2× the $IC_{50}$, nearly 85% of the cells in the pellicle are treated. This efficacy is similar that observed with colistin when used at 20 µM, equivalent to 25× the MIC (FIG. 3(I)).

Figure 5:
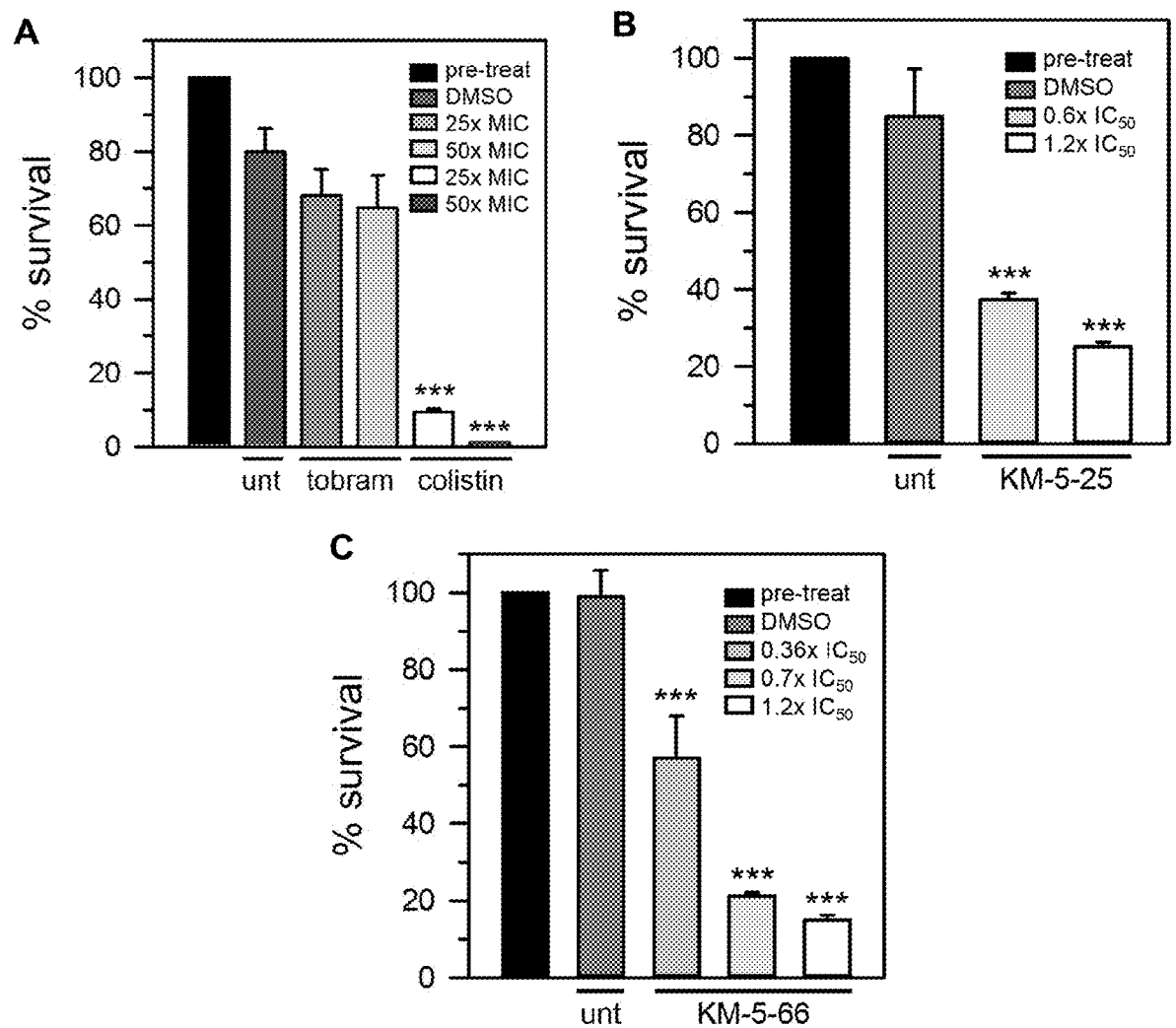
FIG. 5 shows the assessment of cell survival in pellicle biofilms by dispersing and counting viable cells. EYFP-expressing P. aeruginosa PAO1 cells embedded in two-day old pellicles treated for 24 h with antibiotic or 4-aminoisoindoline-1,3-dione derivatives were dispersed for enumeration of viable culturable cells (CFU/mL). % Survival is expressed as the ratio CFU/mL$_{(after\ treatment)}$/CFU/mL$_{(pre-treatment)}$. (A) shows pellicles treated for 24 h with tobramycin (27 µM or 54 µM) or colistin (20 µM or 40 µM). (B) shows pellicles treated for 24 h with concentrations equivalent to 25× and 50× the corresponding MIC with compound KM-5-25 (40 µM and 80 µM), which are concentrations equivalent to 0.6× and 1.2× the IC$_{50}$. (C) shows pellicles treated for 24 h with compound KM-5-66 (15 µM, 30 µM and 50 µM), at concentrations equivalent to 0.36×, 0.7× and 1.2× the IC$_{50}$. p<0.001 denoted by *** relative to untreated.

To assess the efficacy of antibiotics and compounds with an approach complementary to imaging with CLSM, dispersing biofilm cells for subsequent enumeration of viable cells (CFU/mL) was resorted to. To this end, pellicle biofilms were cultured for 48 hours in PI media containing 20 µM Fe, and exposed to AB media containing 15 µM Fe and antibiotic or compound for 24 hours. The biofilms were then harvested, and the cells dispersed into sterile PBS by vortexing in the presence of zirconia beads, prior to plating the cell suspensions for subsequent enumeration of CFU/mL. The results from these experiments are summarized in the plots of FIG. 5(A-C) which show the % cell survival of pellicle-embedded cells after challenges with antibiotic or compound, calculated from the fraction CFU/mL$_{(after\ treatment)}$/CFU/mL$_{(pre-treatment)}$. When colistin is used to treat the pellicles at concentrations equivalent to 25× and 50× the MIC, the treated biofilms exhibit ~10% and ~1% cell survival, respectively, relative to the pre-treated biofilm (FIG. 5(A)), corroborating the sensitivity of the pellicles to colistin. In contrast, challenging the pellicles with tobramycin (25× and 50× the MIC) results in ~70% survival relative to the pre-treated biofilm, and nearly identical cell survival relative to the untreated (DMSO control) pellicles (FIG. 5(A)). These observations, which are in good agreement with those made with the aid of CLSM (FIG. 3(D-H)) corroborate that the pellicles are tolerant to tobramycin and sensitive to colistin. Interestingly, attempts to enumerate cells after challenging the pellicles with ciprofloxacin (25× or 50× the MIC) resulted in extremely low CFU/mL, findings which at first glance appear to be in conflict with the tolerance of the biofilms to ciprofloxacin observed in the CLSM images (FIG. 3(B-C)). To reconcile these seemingly discrepant observations, it is important to consider that several stressors, including ciprofloxacin, can induce a dormant state in bacterial cells known as the viable but not culturable (VBNC) state. A characteristic of cells in the VBNC state is their inability to develop into colonies on routine culture media, even though the cells remain viable for long periods of time.[58-59] Evidence that bacterial cells can enter the VBNC has been obtained by several distinct methods,[59] one of which is the utilization of bacteria engineered to constitutively express bioluminescent proteins, and using the bioluminescence as a reporter of metabolic activity. Studies conducted with P. aeruginosa showed that following treatment with ciprofloxacin the bioluminescence emitted by P. aeruginosa cells decreased significantly less than the viable cell counts (CFU/mL). The perceived reduction in viable cell counts, which did not correlate with the relatively high metabolic activity reported by the small decrease in bioluminescence, indicated that challenges with ciprofloxacin induce P. aeruginosa cells to enter a VBNC state.[60-61] The observations suggest a similar situation. Imaging the pellicles with CLSM following the 24 hours challenge with ciprofloxacin (FIG. 3(B-C)) shows that most of the cells are metabolically active (yellow fluorescent), but dispersion of the cells from the pellicles for enumeration of CFU/mL shows a large reduction in culturable cells relative to the untreated control. These observations strongly suggest that treating the pellicles with ciprofloxacin induces the cells to enter the VBNC state, thus rendering them tolerant to the antibiotic. These findings, which highlight the complexities associated with biofilm embedded cells, also underscore the importance of resorting to more than one platform to study the efficacy of antibiofilm agents.

Figure 6:
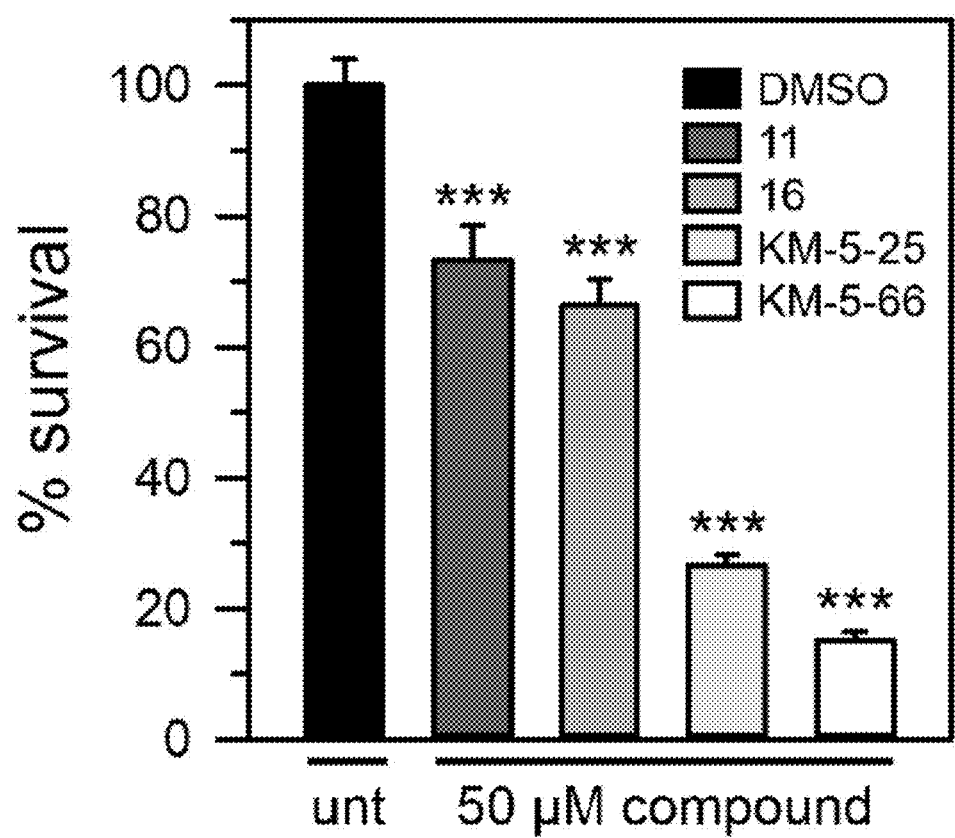
FIG. 6 provides a comparison of the bacteriocidal activity of compounds 11, 16, KM-5-25, and KM-5-66 via assessment of cell survival in pellicle biofilms by dispersing and counting viable cells as performed in the experiments providing FIG. 5, except EYFP-expressing P. aeruginosa PAO1 cells embedded in two-day old pellicles treated for 24 h with 50 µM of one of compound 11, compound 16, compound KM-5-25, or KM-5-66. p<0.001 denoted by *** relative to untreated.

Enumeration of CFU/mL was also carried out after challenging pellicles with 4-aminoisoindoline-1,3-dione derivatives. Treating the pellicles with KM-5-25 at concentrations equivalent to 0.6× and 1.2× the IC$_{50}$ results in ~38% and ~25% survival relative to cells in the pre-treated biofilm (FIG. 5(B)), while treating with KM-5-66 at concentrations equivalent to 0.3×, 0.6× or 1.2× the IC$_{50}$ results in approximately 57%, 21% and 15% survival relative to cells in the pellicles prior to treatment (FIG. 5(C)). These observations, which are in good agreement with the efficacy of the compounds evaluated by COMSTAT analysis of the CLSM images, corroborate the bactericidal activity of the compounds against P. aeruginosa biofilms, and provide additional evidence indicating that KM-5-66 used at 50 µM (1.2× the IC$_{50}$) exhibits nearly the same efficacy as colistin used at 20 µM (25× the MIC). The strategy of dispersing and counting viable cells was also used to compare the relative efficacy of analogs 11, 16, KM-5-25 and KM-5-66. To this end, pellicles formed by P. aeruginosa PAO1 cells were treated (24 h) with each of 11, 16, KM-5-25 and KM-5-66 at a concentration of 50 µM. The results (FIG. 6) show that the compound activity (KM-5-66>KM-5-25>16>11) track with the K$_d$ and IC$_{50}$ values (Table 1).

Figure 7:
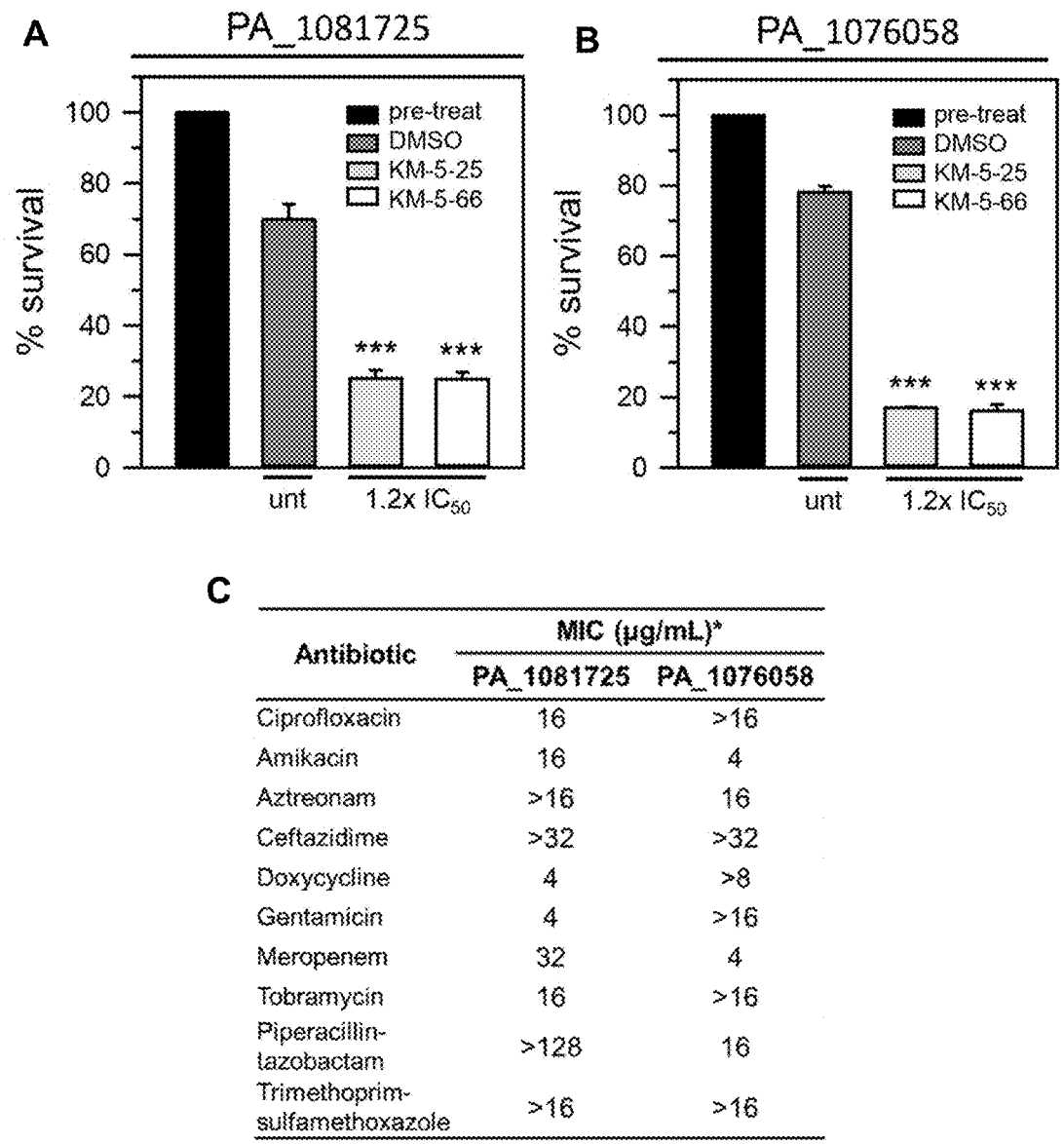
FIG. 7 shows that 4-aminoisoindoline-1,3-dione analogs are active against two different P. aeruginosa strains. Two-day old pellicle biofilms formed by P. aeruginosa clinical isolates (PA_1081725 and PA_1076058) were challenged for 24 h with 4-aminoisoindoline-1,3-dione derivatives prior to dispersing the cells for enumeration of viable culturable cells (CFU/mL). % survival is expressed as the ratio of CFU/mL$_{(after\ treatment)}$/CFU/mL$_{(pre-treatment)}$. (A) shows pellicles of PA_1081725 treated with concentrations equivalent to 1.2× the IC$_{50}$ of KM-5-25 (80 µM), or KM-5-66 (50 µM). (B) shows pellicles of PA_1076058 treated with concentrations equivalent to 1.2× the IC$_{50}$ of KM-5-25 (80 µM), or KM-5-66 (50 µM). (C) shows antibiotic susceptibility of clinical isolates PA_1081725 and PA_1076058. p<0.001 denoted by *** relative to untreated.

The results from experiments aimed at determining the efficacy of the 4-aminoisoindoline-1,3-dione derivatives presented so far have been conducted with the reference strain P. aeruginosa PAO1. To investigate whether the compounds are also active against other strains of P. aeruginosa, pellicles of several clinical isolates from JMI Laboratories were cultured. Isolates PA_1081725 and PA_1076058 were chosen for additional testing because these strains exhibit relatively high MIC values for several antibiotics (FIG. 7(C)) and form robust pellicles under the same culture conditions used to grow pellicle biofilms of P. aeruginosa PAO1. Challenging the pellicles formed by PA_1081725 and PA_1076058 with analogs KM-5-25 or KM-5-66 at concentrations equivalent to 1.2× the IC$_{50}$ elicits approximately 80% reduction of viable cells (FIG. 7(A-B)), indicating that the activity of the 4-aminoisoindoline-1,3-dione analogs is not unique to biofilms formed by the P. aeruginosa PAO1 strain. To gain a broader understanding of the potential activity spectrum of the BfrB-Bfd inhibitors against P. aeruginosa strains, BLASTp[62] was used to find homologs of BfrB and Bfd sequences in the >4,400 P. aeruginosa genomes in the Pseudomonas Genome Database.[63] The results reveal two important facts: (i) The bfrB and bfd genes are adjacent to one another in all the P. aeruginosa strains, (ii) There is an extremely high level of conservation among the bfd and bfrB sequences. These findings evidence that the compounds of the present technology are broadly active against P. aeruginosa.

Figure 8:
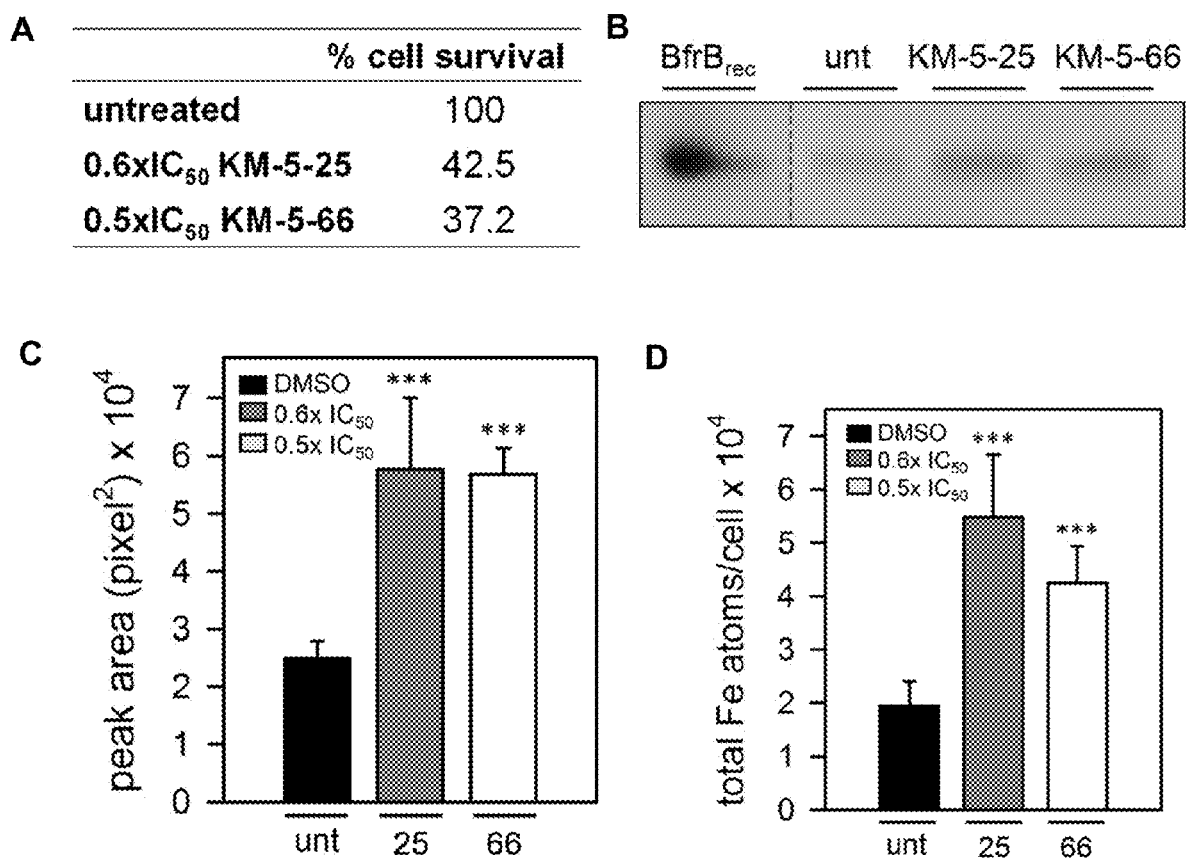
FIG. 8 shows that 4-aminoisoindoline-1,3-dione analogs penetrate the P. aeruginosa cell, bind BfrB and inhibit mobilization of BfrB-stored iron. (A) shows that treating pellicles with 0.6× the IC$_{50}$ of KM-5-25 (40 µM) or 0.5× the IC$_{50}$ of KM-5-66 (20 µM) for 24 h reduces the number of viable cells to <50%. (B) shows that the iron stored in BfrB in the viable cells was visualized with the aid of native PAGE gels stained with Ferene S, which stains the iron in the interior cavity of BfrB. Recombinant BfrB (BfrB$_{rec}$) was used as a standard for the electrophoretic mobility of BfrB. The lane corresponding to untreated control was loaded with 0.5× the volume of the lanes loaded with lysates from treated pellicles to account for the ~2-fold larger number of viable cells in the untreated pellicles. Lanes loaded with treated pellicle lysates show greater accumulation of iron in BfrB relative to untreated cells. (C) shows that peak areas obtained from densitometry analysis (Image J) of the bands in the native PAGE gel of FIG. 8(B) indicate that there is ~3-fold more iron stored in BfrB in the treated cells relative to the untreated control. (D) shows that analysis of total intracellular iron levels normalized to CFU/mL indicates ~2.5-fold higher iron levels in the pellicle-embedded cells treated with the 4-aminoisoindoline-1,3-dione analogs relative to untreated control. (B) shows results from a representative experiment from 3 biological replicates. (A), (C) and (D) show the average of results from 3 biological replicates, p<0.001 is denoted by *** relative to untreated.

Example 6: 4-Aminoisoindoline-1,3-Dione Derivatives Inhibit Iron Mobilization from BfrB in P. aeruginosa Cells To demonstrate that the bactericidal activity is likely a result of the compounds engaging BfrB in the P. aeruginosa cytosol, inhibiting the BfrB-Bfd complex and blocking iron mobilization from the bacterioferritin in the P. aeruginosa cytosol, experiments aimed at visualizing the iron stored in BfrB were carried out. These experiments capitalize on a strategy reported previously demonstrating that the ∆ bfd mutant of P. aeruginosa irreversibly accumulates iron in BfrB[23] and showing that analog 16 inhibits iron mobilization from BfrB in planktonic cells.[25] To visualize BfrB-stored iron in biofilm-embedded cells, 2-day old pellicles of P. aeruginosa PAO1 cells were treated for 24 h with analog KM-5-25 (40 µM) or KM-5-66 (20 µM), concentrations predicted to treat approximately 50% of the cells in the biofilm. The treated pellicles were dispersed in sterile PBS and the cell suspension was harvested by centrifugation after a small aliquot had been sampled to enumerate viable cells. To visualize iron stored in BfrB the harvested cells were lysed, the lysate solution supernatant was clarified by centrifugation and then loaded onto native PAGE gels for separation and visualized by subsequent staining with Ferene S, which reacts with iron to develop a blue color. Since the viable cell count dispersed from the pellicle biofilms treated with KM-5-25 or KM-5-66 was 42% and 37% of the cells in the untreated pellicle (FIG. 8(A)), the clarified lysate supernatants from the untreated control were diluted approximately 2-fold prior to loading the native gels. Results obtained with a representative gel are shown in FIG.

8(B), where it can be observed that lanes loaded with lysate solutions from pellicles treated with analogs KM-5-25 or KM-5-66 exhibit significantly higher Ferene S stain intensity than the lane loaded with lysate solution from the untreated pellicle. To enable quantitative comparison, the relative intensities of the Ferene S-stained bands were measured with the aid of Image J. Comparison of the resultant peak areas (FIG. 8(C)) shows that BfrB from the cells treated with KM-5-25 or KM-5-66 has ~3-fold more iron relative to BfrB from cells in the untreated pellicles. These findings provide strong evidence indicating that compounds KM-5-25 and KM-5-66 bind BfrB in the *P. aeruginosa* cytosol, inhibit the formation of the BfrB-Bfd complex required to mobilize iron from BfrB, and lead to nearly irreversible iron accumulation in BfrB. Consistent with the nearly irreversible accumulation of iron in BfrB in cells treated with KM-5-25 or KM-5-66, quantification of the total intracellular iron and normalizing the values to viable cell counts demonstrates that *P. aeruginosa* cells dispersed from pellicles treated with KM-5-25 or KM-5-66 harbor ~2.5-fold more intracellular iron than cells obtained from untreated biofilms (FIG. 8(D)). Taken together, these observations support the idea that 4-aminoisoindoline-1,3-dione derivatives dysregulate iron homeostasis by inhibiting the BfrB-Bfd complex, causing the accumulation of unusable iron in the bacterial cell.

Figure 9:
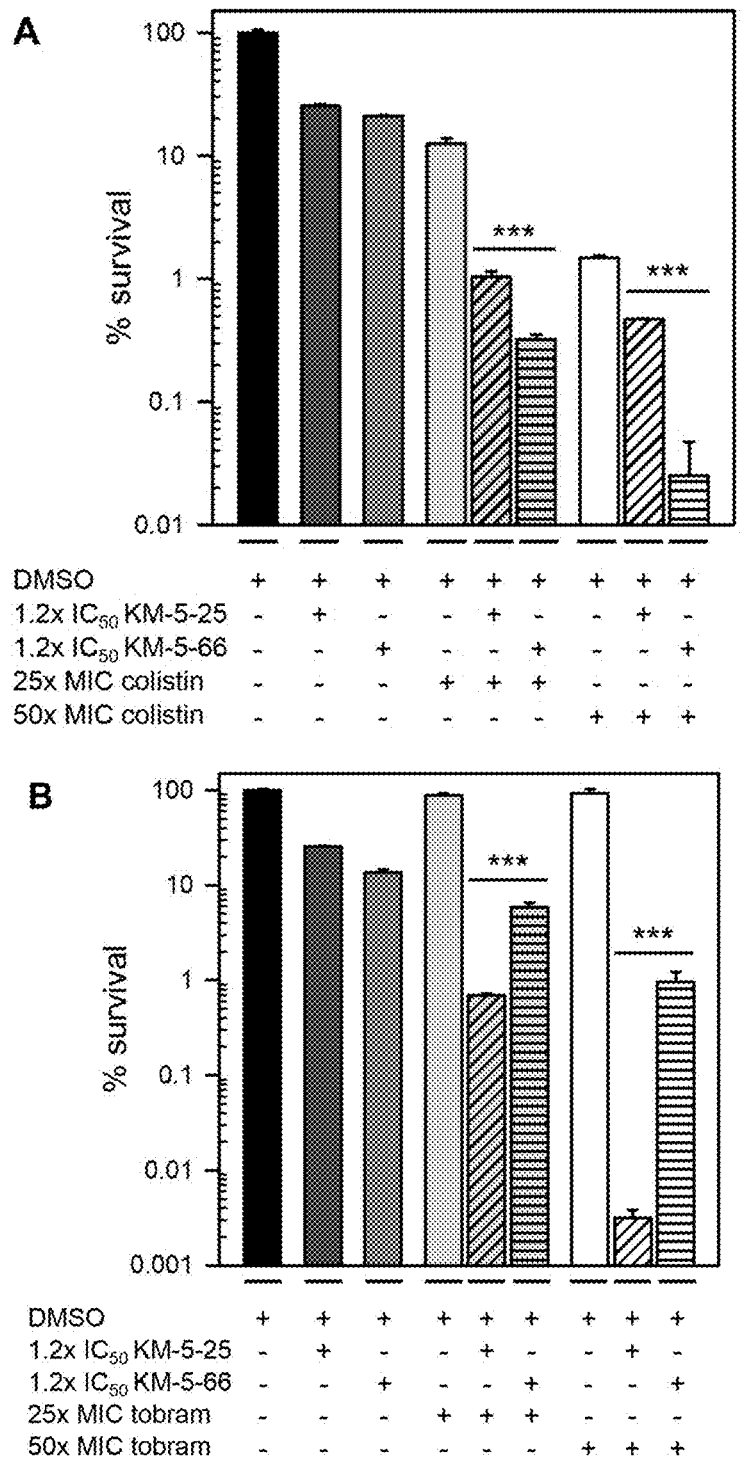
FIG. 9 shows that 4-aminoisoindoline-1,3-dione derivatives enhance the efficacy of colistin and tobramycin against P. aeruginosa biofilms. (A) shows two-day old pellicles of EYFP-expressing P. aeruginosa PAO1 treated for 24 h with colistin alone 25× the MIC (20 µM), or 50× the MIC (40 µM), KM-5-25 (80 µM) or KM-5-66 (50 µM) alone, equivalent to 1.2× the IC$_{50}$, or a combination of colistin and KM-5-25 or KM-5-66. (B) shows two-day old pellicles of EYFP-expressing P. aeruginosa PAO1 treated for 24 h with tobramycin alone 25× the MIC (27 µM) or 50× the MIC (40 µM), KM-5-25 or KM-5-66 alone at a concentration equivalent to 1.2× the IC$_{50}$, or a combination of tobramycin and KM-5-25 or KM-5-66. The % survival is expressed as the ratio CFU/mL$_{(after\ treatment)}$/CFU/mL$_{(pre-treatment)}$. p<0.001 is denoted by *** in the combination treatment relative to treatment with antibiotic alone.
Figure 10:
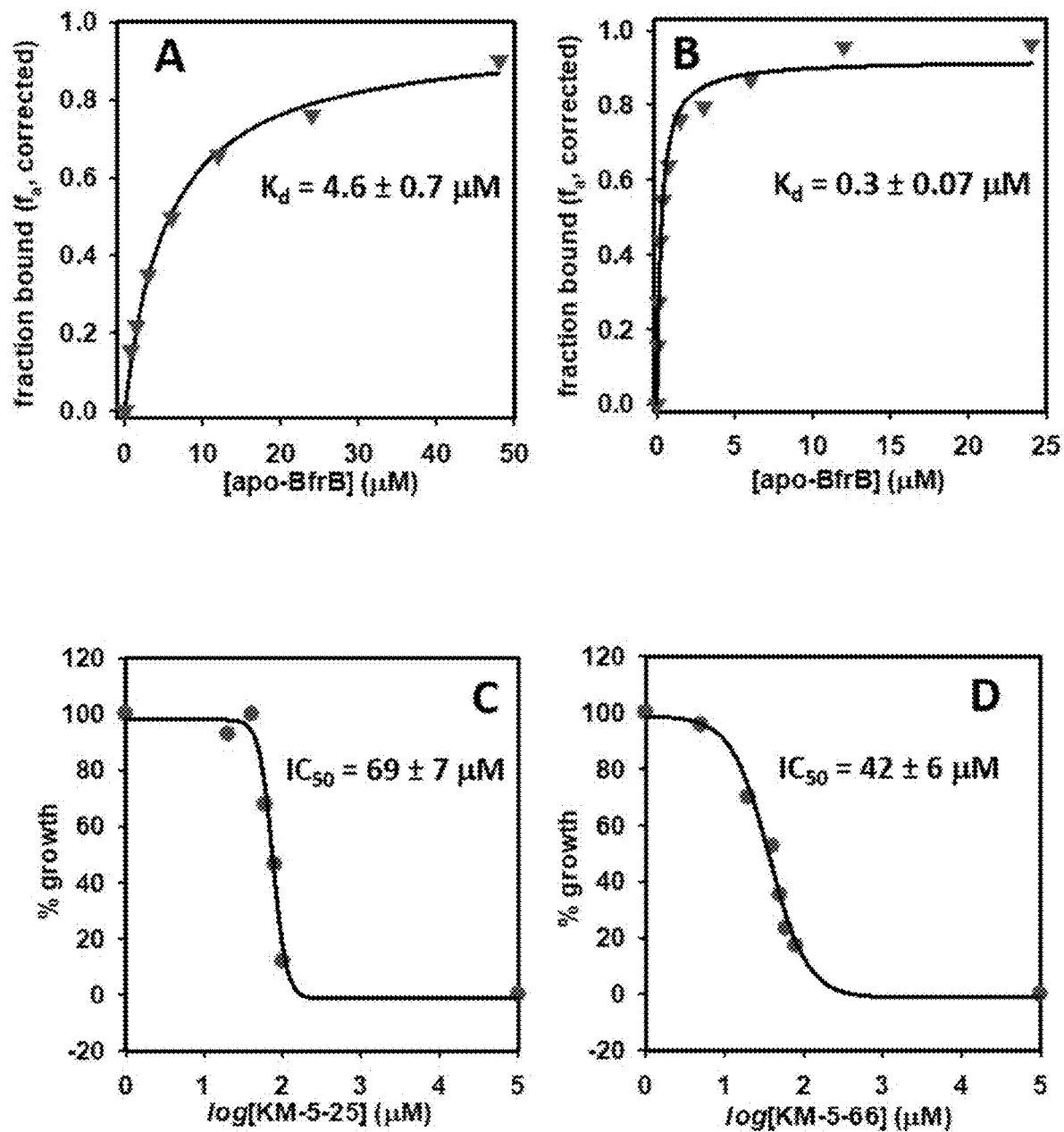
FIG. 10 shows quantification of the affinity (K$_d$) of 4-aminoisoindoline-1,3-dione derivatives. (A) shows quantification of the affinity (K$_d$) of KM-5-25 evaluated by fluorescence polarization. (B) shows quantification of the affinity (K$_d$) of KM-5-66 evaluated by fluorescence polarization. Values were obtained in 100 mM potassium phosphate buffer (pH 7.6) containing 1 mM TCEP and 0.5% DMSO. The initial concentrations of KM-5-25 and KM-5-66 were 5 µM. The K$_d$ values are the average and standard deviation from three independent measurements. (C) shows quantification of half maximal inhibitory concentration (IC$_{50}$) for KM-5-25 as described in Example 2. (D) shows quantification of half maximal inhibitory concentration (IC$_{50}$) for KM-5-66 as described in Example 2. The IC$_{50}$ values are the average and the standard derivations from three independent experiments.

Example 7: 4-Aminoisoindoline-1,3-Dione Derivatives Enhance the Efficacy of Colistin and Tobramycin Against Biofilm-Embedded Cells As demonstrated above and in previous reports,[64-65] mature biofilms formed by *P. aeruginosa* cells are susceptible to colistin and tolerant to tobramycin. Since these biofilms are also susceptible to the 4-aminoisoindoline-1,3-dione inhibitors of the BfrB-Bfd complex, whether these compounds would enhance the efficacy of colistin and tobramycin were investigated. 2-Day old pellicle biofilms of EYFP-expressing *P. aeruginosa* PAO1 were cultured and treated for 24 h with colistin alone, compound alone (KM-5-25 or KM-5-66), or a combination of colistin and compound. In the combination treatment experiments, the concentration of compound was kept constant (1.2× the $IC_{50}$), while colistin was used at two different concentrations, equivalent to 25× and 50× the MIC (FIG. 9(A)). Treatment with each of the compounds or with colistin alone caused a reduction of viable cells similar to that shown in FIG. 5(A). Challenging the pellicles with a combination of colistin and a compound of present technology, however, causes a significant additional reduction in the number of viable cells. As shown in FIG. 9(A), the combination treatment with KM-5-66 results in ~0.3% survival when colistin is present at 25× the MIC, and ~0.02% survival when colistin is used at 50× the MIC, which correspond to approximately 1.7 log and 1.9 log reduction of viable cells relative to treatment with colistin alone. In comparison, the combination treatment with KM-5-25 results in ~1% survival when colistin is used at 25× the MIC and ~0.5% survival when colistin is present at 50× the MIC, which correspond to nearly 1 log and 0.7 log reduction of viable cells, respectively, compared to colistin alone. Furthermore, the question of whether the 4-aminoisoindoline-1,3-dione derivatives of the present technology can also enhance the bactericidal activity of tobramycin was examined. As shown in FIG. 9(B), the combination treatment with KM-5-25 results in ~0.5% survival when tobramycin is used at 25× the MIC and ~0.003% survival when tobramycin is present at 50× the MIC, which correspond to approximately 2.5 log and 4.7 log reduction of viable cells when compared to treatment with tobramycin alone. The combination treatment with KM-5-66 results in 5% survival when tobramycin is present at 25× the MIC and 1% survival when tobramycin is used at 50× the MIC, which correspond to approximately 1.5 log and 2 log reduction in viable cells relative to treatment with tobramycin alone. It is interesting to note that compound KM-5-66 is more effective at enhancing the efficacy of colistin (FIG. 9(A)), whereas compound KM-5-25 is more effective at enhancing the efficacy of tobramycin (FIG. 9(B)). Additional studies are clearly required to understand the underlying reasons.

Figure 12:
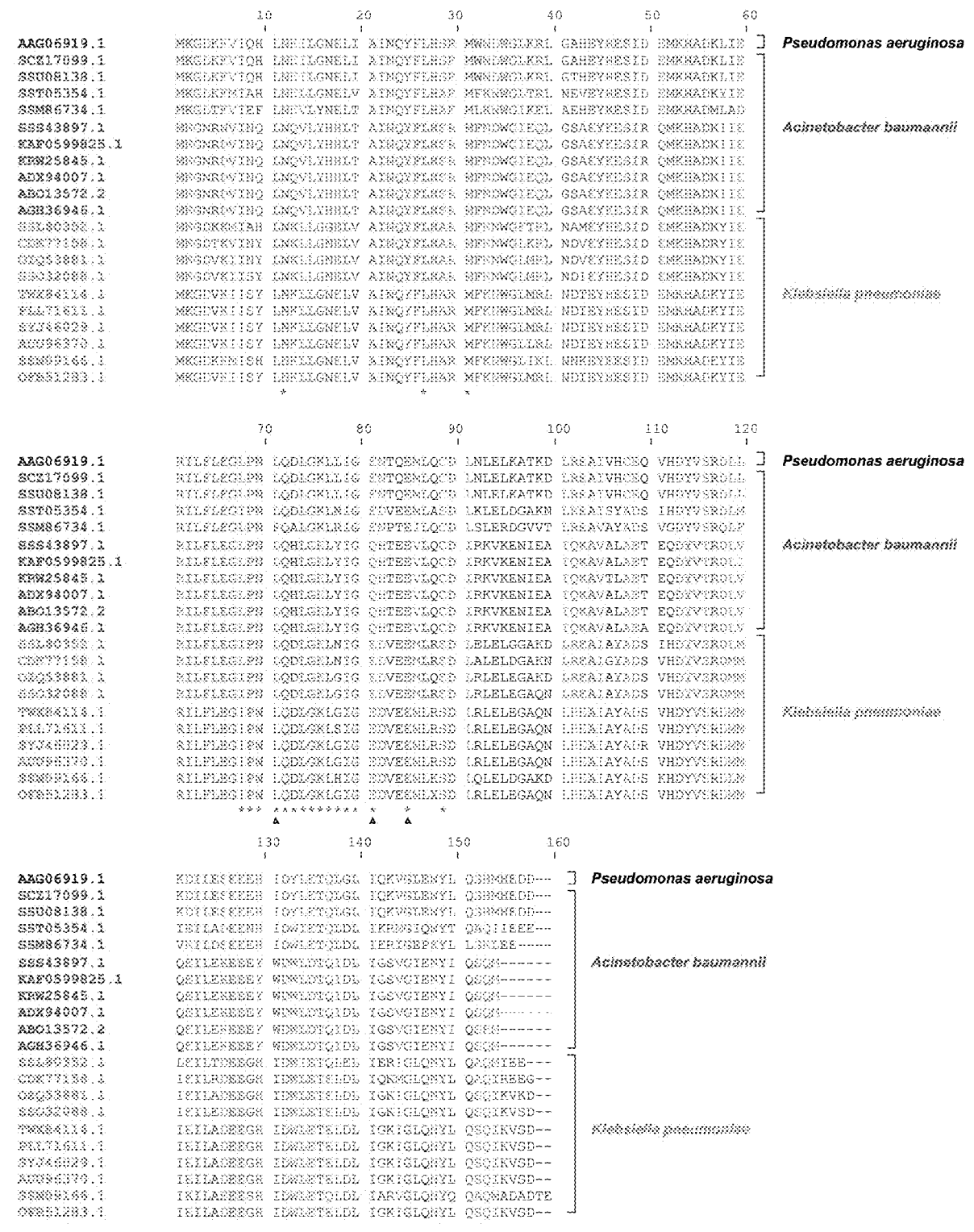

The observations above, which indicate that the iron limitation induced by inhibitors of the BfrB-Bfd complex can increase the efficacy of colistin and tobramycin against biofilms, are in good agreement with previous studies showing that the Fe chelator HBDE is an effective colistin adjunct against *P. aeruginosa*,[66] and the iron chelators deferoxamine and deferasirox increase the efficacy of tobramycin against *P. aeruginosa* biofilms.[67] When taken together, the observations made in the presence of HBDE, deferoxamine, deferasirox or 4-aminoisoindoline-1,3-dione derivatives, strengthen the idea that inducing intracellular iron limitation is probably a viable strategy to enhance the efficacy of colistin or tobramycin against biofilms. Since colistin is often used as one of the very few therapeutic options available to combat multidrug resistant Gram-negative organisms such as *Acinetobacter baumannii*, *Pseudomonas aeruginosa* and *Klebsiella pneumoniae*,[68-69] it is encouraging that small molecule inhibitors of the BfrB-Bfd complex are capable of increasing the effectiveness of colistin against *P. aeruginosa*. In this context, it is noteworthy that the bfr and bfd genes in *A. baumannii* and *K. pneumoniae* strains are contiguous, as is the case in the >4,000 *P. aeruginosa* genomes currently available in the *Pseudomonas* Genome Data Base, because it indicates that the function of the Bfr-Bfd complex in *P. aeruginosa* is conserved in *A. baumannii* and *K. pneumoniae*. Moreover, amino acid sequence alignment with the aid of Clustal Omega[70] reveals very high conservation in the amino acid sequences of Bfr and Bfd proteins from *P. aeruginosa*, *A. baumannii* and *K. pneumoniae* (FIG. 12 and FIG. 13). Importantly, the amino acids identified as hot spot residues in the BfrB-Bfd complex of *P. aeruginosa*[33] are highly conserved in the Bfr and Bfd sequences of *A. baumannii* and *K. pneumoniae*, so that compounds of the present technology, designed to inhibit the BfrB-Bfd interaction in *P. aeruginosa*, will act similarly in *A. baumannii* and if. *pneumoniae*.

Example 8: Compounds of the Present Technology Inhibit Bacterial Biofilm Formation in an In Vivo Murine Model of Wound Infection Effects of vehicle, a positive control, or a compound of the present technology on biofilm formation of a luminescent bacteria strain, *P. aeruginosa* strain PA01, will be tested in an in vivo murine model of wound infection.

First, female CD1 mice at 8 to 12 weeks of age will be anesthetized via i.p. administration of ketamine and xylazine. A full thickness biopsy wound will be generated using a 5-mm biopsy punch (Integra Lifesciences, Plainsboro Township, NJ) on depilated and chlorhexidine-scrubbed dorsal surfaces. A silicon ring (Invitrogen, Carlsbad, CA) 0.5 mm thick with an outer diameter of 10 mm and a hole with a 5-mm diameter will be placed over the wound and held to the skin with a surgical adhesive. The silicon ring will be covered with a Tegaderm transparent film dressing (3M, Saint Paul, MN), and further adhered using 4-0 braided silk interrupted sutures (Ethicon Inc., Somerville, NJ). Mice will be given 0.05 mg/kg buprenorphine immediately following surgery as well as daily for the next 2 days to alleviate pain from the procedure. Wound beds will be infected by penetrating the Tegaderm with an insulin syringe and injecting $1 \times 10^4$ CFUs of bioluminescent *P. aeruginosa* (PA01) suspended in 10 µL of sterile PBS directly onto the wound bed. Four hours after infection, mice will be topically treated with vehicle, a positive control, or a compound of the present technology in a 20 µL volume injecting directly into the wound bed. Treatment will be every 8 h for the first 5 days of infection. Mice will be imaged daily for 2 weeks using the in vivo imaging system (IVIS)-XMRS (PerkinElmer, Waltham, MA), and bioluminescence generated from the bacteria will be quantified in values of radiance (photons/sec/centimeter$^2$/steradian).

The Tegaderm wound dressings will be removed after 3 days of infection and examined by electron microscopy for bacteria and bacterial biofilms. Briefly, a sample of the Tegaderm will be adhered to a hydroxyapatite disk (5 mm), and fixed in glutaraldehyde (2.5%, Electron Microscopy Sciences, Hatfield, PA) overnight at 4° C. Thereafter, the disk will be washed 3× in distilled H$_2$O, and then dehydrated in 5 min sequential washes of EtOH (25, 50, 75, 90, and 100%). Samples will be then critical point dried (AUTOSAMDRIR-814, Tousimis, Rockville, MD, United States), coated in carbon, and imaged using SEM (Hitachi S-4800 FEG CRYO-SEM). Representative images of each sample (n=10) at both 2K× and 10K× will be taken at an operational voltage of 3 Kv.

Tegaderm dressings from *P. aeruginosa*-infected animals will show evidence of individual *Pseudomonas*-like rods, and complex bacterial-containing three-dimensional (3D) matrices representing organized bacterial biofilms. The group treated with the compounds of the present technology, the Tegaderm dressings will show a similar or lower amount of organized biofilms compared to the positive control group, demonstrating that the compounds of the present technology possess similar or superior biofilm inhibitory activity in comparison to the positive control.

Accordingly, the compounds of the present technology are useful in inhibiting biofilm formation.

Example 9: Compounds of the Present Technology Remediate Bacterial Biofilms in an In Vivo Murine Model Effects of vehicle, a positive control, or a compound of the present technology on biofilm formation of a luminescent bacteria strain, *P. aeruginosa* strain PA01, will be tested in an in vivo murine model of wound infection.

First, female CD1 mice at 8 to 12 weeks of age will be anesthetized via i.p. administration of ketamine and xylazine. A full thickness biopsy wound will be generated using a 5-mm biopsy punch (Integra Lifesciences, Plainsboro Township, NJ) on depilated and chlorhexidine-scrubbed dorsal surfaces. A silicon ring (Invitrogen, Carlsbad, CA) 0.5 mm thick with an outer diameter of 10 mm and a hole with a 5-mm diameter will be placed over the wound and held to the skin with a surgical adhesive. The silicon ring will be covered with a Tegaderm transparent film dressing (3M, Saint Paul, MN), and further adhered using 4-0 braided silk interrupted sutures (Ethicon Inc., Somerville, NJ). Mice will be given 0.05 mg/kg buprenorphine immediately following surgery as well as daily for the next 2 days to alleviate pain from the procedure. Wound beds will be infected by penetrating the Tegaderm with an insulin syringe and injecting $1 \times 10^4$ CFUs of bioluminescent *P. aeruginosa* (PA01) suspended in 10 µL sterile PBS directly onto the wound bed. At 24 hours or 48 hours after infection (thus allowing for establishment of a biofilm), mice will be topically treated with vehicle, a positive control, or a compound of the present technology in a 20 µL volume injecting directly into the wound bed. Treatment will be every 8 h for 5 days. Mice will be imaged daily for 2 weeks using the in vivo imaging system (IVIS)-XMRS (PerkinElmer, Waltham, MA), and bioluminescence generated from the bacteria will be quantified in values of radiance (photons/sec/centimeter$^2$/steradian).

The Tegaderm wound dressings will be removed after 3 days of infection and examined by electron microscopy for bacteria and bacterial biofilms. Briefly, a sample of the Tegaderm will be adhered to a hydroxyapatite disk (5 mm), and fixed in glutaraldehyde (2.5%, Electron Microscopy Sciences, Hatfield, PA) overnight at 4° C. Thereafter, the disk will be washed 3× in distilled H$_2$O, and then dehydrated in 5 min sequential washes of EtOH (25, 50, 75, 90, and 100%). Samples will be then critical point dried (AUTOSAMDRIR-814, Tousimis, Rockville, MD, United States), coated in carbon, and imaged using SEM (Hitachi S-4800 FEG CRYO-SEM). Representative images of each sample (n=10) at both 2K× and 10K× will be taken at an operational voltage of 3 Kv.

Tegaderm dressings from *P. aeruginosa*-infected animals will show evidence of individual *Pseudomonas*-like rods, and complex bacterial-containing three-dimensional (3D) matrices representing organized bacterial biofilms. The group treated with the compounds of the present technology, the Tegaderm dressings will show a similar or lower amount of organized biofilms compared to the positive control group, demonstrating that the compounds of the present technology possess similar or superior activity in remediating biofilms in comparison to the positive control.

Accordingly, the compounds of the present technology are useful in remediating biofilms.

REFERENCES

1. Tacconelli, E.; Carrara, E.; Savoldi, A.; Harbarth, S.; Mendelson, M.; Monnet, D. L.; Pulcini, C.; Kahlmeter, G.; Kluytmans, J.; Carmeli, Y.; Ouellette, M.; Outterson, K.; Patel, J.; Cavaleri, M.; Cox, E. M.; Houchens, C. R.; Grayson, M. L.; Hansen, P.; Singh, N.; Theuretzbacher, U.; Magrini, N.; Group, W. H. O. P. P. L. W. (2018) Discovery, research, and development of new antibiotics: the WHO priority list of antibiotic-resistant bacteria and tuberculosis. *Lancet Infect. Dis.* 18, 318-327. 10.1016/S1473-3099(17)30753-3
2. Davies, D. (2003) Understanding biofilm resistance to antibacterial agents. *Nat. Rev. Drug Discov.* 2, 114-122. 10.1038/nrd1008
3. Lawrence, J. R.; Korber, D. R.; Hoyle, B. D.; Costerton, J. W.; Caldwell, D. E. (1991) Optical sectioning of microbial biofilms. *J. Bacteriol.* 173, 6558-6567. 10.1128/jb.173.20.6558-6567.1991
4. Sutherland, I. (2001) Biofilm exopolysaccharides: a strong and sticky framework. *Microbiology* 147, 3-9. 10.1099/00221287-147-1-3
5. Lam, J.; Chan, R.; Lam, K.; Costerton, J. W. (1980) Production of Mucoid Microcolonies by *Pseudomonas aeruginosa* Within Infected Lungs in Cystic Fibrosis. *Infect. Immun.* 28, 546-556. PMCID PMC550970

6. Costerton, J. W.; Stewart, P. S.; Greenberg, E. P. (1999) Bacterial Biofilms: A Common Cause of Persistent Infection. *Science* 284, 1318-1322. 10.1126/science.284.5418.1318
7. Parsek, M. R.; Singh, P. K. (2003) Bacterial biofilms: an emerging link to disease pathogenesis. *Ann. Rev. Microbiol.* 57, 677-701. 10.1146/annurev.micro.57.030502.090720
8. Konstan, M. W.; Morgan, W. J.; Butler, S. M.; Pasta, D. J.; Craib, M. L.; Silva, S. J.; Stokes, D. C.; Wohl, M. E.; Wagener, J. S.; Regelmann, W. E.; Johnson, C. A.; MBCHB for the Scientific Advisory Group and the Investigators and Coordinators of the Epidemiologic Study of Cystic Fibrosis (2007) Risk factors for rate of decline in forced expiratory volume in one second in children and adolescents with cystic fibrosis. *J. Pediatr.* 151, 134-139, 139 e1. 10.1016/j.jpeds.2007.03.006
9. Crull, M. R.; Ramos, K. J.; Caldwell, E.; Mayer-Hamblett, N.; Aitken, M. L.; Goss, C. H. (2016) Change in *Pseudomonas aeruginosa* prevalence in cystic fibrosis adults over time. *BMC Pulm Med.* 16, 176-page. 10.1186/s12890-016-0333-y
10. Romling, U.; Balsalobre, C. (2012) Biofilm infections, their resilience to therapy and innovative treatment strategies. *J. Intern. Med.* 272, 541-561. 10.1111/joim.12004
11. Burrows, L. L. (2018) The Therapeutic Pipeline for *Pseudomonas aeruginosa* Infections. *ACS Infect. Dis.* 4, 1041-1047. 10.1021/acsinfecdis.8b00112
12. Boucher, H. W.; Talbot, G. H.; Bradley, J. S.; Edwards, J. E.; Gilbert, D.; Rice, L. B.; Scheld, M.; Spellberg, B.; Bartlett, J. (2009) Bad Bugs, No Drugs: No ESKAPE! An Update from the Infectious Diseases Society of America. *Clin. Infect. Dis.* 48, 1-11. 10.1086/595011
13. James, G. A.; Swogger, E.; Wolcott, R.; Pulcini, E.; Secor, P.; Sestrich, J.; Costerton, J. W.; Stewart, P. S. (2008) Biofilms in chronic wounds. *Wound Repair Regen.* 16, 37-44. 10.1111/j.1524-475X.2007.00321.x
14. Kadam, S.; Shai, S.; Shahane, A.; Kaushik, K. S. (2019) Recent Advances in Non-Conventional Antimicrobial Approaches for Chronic Wound Biofilms: Have We Found the 'Chink in the Armor'? Biomedicines 7, page or article number. 10.3390/biomedicines7020035
15. Crabbe, A.; Jensen, P. O.; Bjamsholt, T.; Coenye, T. (2019) Antimicrobial Tolerance and Metabolic Adaptations in Microbial Biofilms. *Trends Microbiol* 27, 850-863. 10.1016/j.tim.2019.05.003
16. Ceri, H.; Olson, M. E.; Stremick, C.; Read, R. R.; Morck, D.; Buret, A. (1999) The Calgary Biofilm Device: new technology for rapid determination of antibiotic susceptibilities of bacterial biofilms. *J. Clin. Microbiol.* 37, 1771-1776. 10.1128/JCM.37.6.1771-1776.1999
17. Stewart, P. S.; Costerton, J. W. (2001) Antibiotic resistance of bacteria in biofilms. *Lancet* 358, 135-138. 10.1016/s0140-6736(01)05321-1
18. Anwar, H.; Costerton, J. W. (1990) Enhanced activity of combination of tobramycin and piperacillin for eradication of sessile biofilm cells of *Pseudomonas aeruginosa*. *Antimicrob. Agents Chemother.* 34, 1666-1671. 10.1128/aac.34.9.1666
19. Chellat, M. F.; Raguz, L.; Riedl, R. (2016) Targeting Antibiotic Resistance. *Angew. Chem. Int. Ed. Engl.* 55, 6600-6026. 10.1002/anie.201506818
20. Lakemeyer, M.; Zhao, W.; Mandl, F. A.; Hammann, P.; Sieber, S. A. (2018) Thinking Outside the Box-Novel Antibacterials To Tackle the Resistance Crisis. *Angew. Chem. Int. Ed. Engl.* 57, 14440-14475. 10.1002/anie.201804971
21. Verderosa, A. D.; Totsika, M.; Fairfull-Smith, K. E. (2019) Bacterial Biofilm Eradication Agents: A Current Review. *Front. Chem.* 7, 824-xxx. 10.3389/fchem.2019.00824
22. Bullen, J. J.; Rogers, H. J.; Spalding, P. B.; Ward, C. G. (2005) Iron and Infection: The Heart of the Matter. *FEMS Immunol. Med. Microbiol.* 43, 325-330. 10.1016/j.femsim.2004.11.010
23. Eshelman, K.; Yao, H.; Punchi Hewage, A. N. D.; Deay, J. J.; Chandler, J. R.; Rivera, M. (2017) Inhibiting the BfrB:Bfd Interaction in *Pseudomonas aeruginosa* Causes Irreversible Iron Accumulation in Bacterioferritin and Iron Deficiency in the Bacterial Cell. *Metallomics* 9, 646-659. DOI: 10.1039/C7MT00042A
24. Keyer, K.; Imlay, J. A. (1996) Superoxide Accelerates DNA-Damage by Elevating Free-Iron Levels. *Proc. Natl. Acad. Sci. USA* 93, 13635-13649. DOI: doi.org/10.1073/pnas.93.24.13635
25. Punchi Hewage, A. N. D.; Yao, H.; Nammalwar, B.; Gnanasekaran, K. K.; Lovell, S.; Bunce, R. A.; Eshelman, K.; Phaniraj, S. M.; Lee, M. M.; Peterson, B. R.; Battaile, K. P.; Reitz, A. B.; Rivera, M. (2019) Small Molecule Inhibitors of the BfrB-Bfd Interaction Decrease *Pseudomonas aeruginosa* Fitness and Potentiate Fluoroquinolone Activity. *J. Am. Chem. Soc.* 141, 8171-8184. 10.1021/jacs.9b00394
26. Soldano, A.; Yao, H.; Chandler, J. R.; Rivera, M. (2020) Inhibiting Iron Mobilization from Bacterioferritin in *Pseudomonas aeruginosa* Impairs Biofilm Formation Irrespective of Environmental Iron Availability. *ACS Infect. Dis.* 6, 447-458. 10.1021/acsinfecdis.9b00398
27. Yao, H.; Jepkorir, G.; Lovell, S.; Nama, P. V.; Weeratunga, S. K.; Battaille, K. P.; Rivera, M. (2011) Two Disctinct Ferritin-Like Molecules in *P. aeruginosa*: The Product of the bfrA Gene is a Bacterial Ferritin (FtnA) not a bacterioferritin (Bfr). *Biochemistry* 50, 5236-5248. 10.1021/bi2004119
28. Rivera, M. (2017) Bacterioferritin: Structure, Dynamics and Protein-Protein Interactions at Play in Iron Storage and Mobilization. *Acc. Chem. Res.* 50, 331-340. 10.1021/acs.accounts.6b00514
29. Weeratunga, S.; Lovell, S.; Yao, H.; Battaile, K. P.; Fischer, C. J.; Gee, C. E.; Rivera, M. (2010) Structural Studies of Bacterioferritin B (BfrB) from *Pseudomonas aeruginosa* Suggest a Gating Mechanism for Iron Uptake via the Ferroxidase Center. *Biochemistry* 49, 1160-1175. 10.1021/bi9015204
30. Yao, H.; Wang, Y.; Lovell, S.; Kumar, R.; Ruvinsky, A. M.; Battaile, K. P.; Vakser, I. A.; Rivera, M. (2012) The Structure of the BfrB-Bfd Complex Reveals Protein-Protein Interactions Enabling Iron Release from Bacterioferritin. *J. Am. Chem. Soc.* 134, 13470-13481. 10.1021/ja305180n
31. Weeratunga, S.; Gee, C. E.; Lovell, S.; Zeng, Y.; Woodin, C. L.; Rivera, M. (2009) Binding of *Pseudomonas aeruginosa* Apobacterioferritin-Associated Ferredoxin to Bacterioferritin B Promotes Heme Mediation of Electron Delivery and Mobilization of Core Mineral Iron. *Biochemistry* 48, 7420-7431. 10.1021/bi900561a
32. Wijerathne, H.; Yao, H.; Wang, Y.; Lovell, S.; Battaile, K. P.; Rivera, M. (2018) Bfd, a New Class of [2Fe-2S] Protein That Functions in Bacterial Iron Homeostasis, Requires a Structural Anion Binding Site. *Biochemistry* 57, 5533-5543. 10.1021/acs.biochem.8b00823
33. Wang, Y.; Yao, H.; Cheng, Y.; Lovell, S.; Battaile, K. P.; Middaugh, C. R.; Rivera, M. (2015) Characterization of the Bacterioferritin/Bacterioferritin Associated Ferredoxin Protein-Protein Interactions in Solution and Determination of Binding Energy Hot Spots. *Biochemistry* 54, 6162-6175. 10.1021/acs.biochem.5b00937

34. Banin, E.; Vasil, M. L.; Greenberg, E. P. (2005) Iron and *Pseuodomonas aeruginosa* biofilm formation. *Proc. Natl. Acad. Sci. U.S.A.* 102, 11076-11081. 10.1073/pnas.0504266102

35. Kang, D.; Kirienko, N. V. (2018) Interdependence between iron acquisition and biofilm formation in *Pseudomonas aeruginosa. J. Microbiol.* 56, 449-457. 10.1007/s12275-018-8114-3

36. Singh, P. K.; Parsek, M. R.; Greenberg, E. P.; Welsh, M. J. (2002) A Component of Innate Immunity Prevents Bacterial Biofilm Development. *Nature* 417, 552-555. 10.1038/417552a 37. Post, S. J.; Shapiro, J. A.; Wuest, W. M. (2019) Connecting iron acquisition and biofilm formation in the ESKAPE pathogens as a strategy for combatting antibiotic resistance. *Medchemcomm* 10, 505-512. 10.1039/c9md00032a 38. Gnanasekaran, K. K.; Rivera, M.; Bunce, R. A. (2018) 4,7-Diaminoisoindoline-1,3-dione. *Org. Prep. Proced. Int.* 50, 372-374. 10.1080/00304948.2018.1462072

39. Harmsen, M.; Yang, L.; Pamp, S. J.; Tolker-Nielsen, T. (2010) An update on *Pseudomonas aeruginosa* biofilm formation, tolerance, and dispersal. *FFMS Immunol. Med. Microbiol.* 59, 253-268. 10.1111/j. 1574-695X.2010.00690.X 40. Brauner, A.; Fridman, O.; Gefen, O.; Balaban, N. Q. (2016) Distinguishing between resistance, tolerance and persistence to antibiotic treatment. *Nat. Rev. Microbiol.* 14, 320-330. 10.1038/nrmicro.2016.34

41. Anwar, H.; Strap, J. L.; Chen, K.; Costerton, J. W. (1992) Dynamic interactions of biofilms of mucoid *Pseudomonas aeruginosa* with tobramycin and piperacillin. *Antimicrob. Agents Chemother.* 36, 1208-1214. 10.1128/aac.36.6.1208

42. Anderl, J. N.; Zahller, J.; Roe, F.; Stewart, P. S. (2003) Role of nutrient limitation and stationary-phase existence in *Klebsiella pneumoniae* biofilm resistance to ampicillin and ciprofloxacin. *Antimicrob. Agents Chemother.* 47, 1251-1256. 10.1128/aac.47.4.1251-1256.2003

43. Walters, M. C., 3rd; Roe, F.; Bugnicourt, A.; Franklin, M. J.; Stewart, P. S. (2003) Contributions of antibiotic penetration, oxygen limitation, and low metabolic activity to tolerance of *Pseudomonas aeruginosa* biofilms to ciprofloxacin and tobramycin. Antimicrob. *Agents Chemother.* 47, 317-323. 10.1128/aac.47.1.317-323.2003

44. Xu, K. D.; Stewart, P. S.; Xia, F.; Huang, C. T.; McFeters, G. A. (1998) Spatial physiological heterogeneity in *Pseudomonas aeruginosa* biofilm is determined by oxygen availability. *Appl. Environ. Microbiol.* 64, 4035-4039. 10.1128/AEM.64.10.4035-4039.1998

45. Werner, E.; Roe, F.; Bugnicourt, A.; Franklin, M. J.; Heydorn, A.; Molin, S.; Pitts, B.; Stewart, P. S. (2004) Stratified growth in *Pseudomonas aeruginosa* biofilms. *Appl. Environ. Microbiol.* 70, 6188-6196. 10.1128/AEM.70.10.6188-6196.2004

46. Hentzer, M.; Wu, H.; Andersen, J. B.; Riedel, K.; Rasmussen, T. B.; Bagge, N.; Kumar, N.; Schembri, M. A.; Song, Z.; Kristoffersen, P.; Minefield, M.; Costerton, J. W.; Molin, S.; Eberl, L.; Steinberg, P.; Kjelleberg, S.; Hoiby, N.; Givskov, M. (2003) Attenuation of *Pseudomonas aeruginosa* virulence by quorum sensing inhibitors. *EMBO J.* 22, 3803-3815. 10.1093/emboj/cdg366

47. Banin, E.; Brady, K. M.; Greenberg, E. P. (2006) Chelator-induced dispersal and killing of *Pseudomonas aeruginosa* cells in a biofilm. *Appl. Environ. Microbiol.* 72, 2064-2069. 10.1128/AEM.72.3.2064-2069.2006

48. Pamp, S. J.; Gjermansen, M.; Johansen, H. K.; Tolker-Nielsen, T. (2008) Tolerance to the antimicrobial peptide colistin in *Pseudomonas aeruginosa* biofilms is linked to metabolically active cells, and depends on the pmr and mexAB-oprM genes. *Mol. Microbiol.* 68, 223-240. 10.1111/j 0.1365-2958.2008.06152.x 49. Vrany, J. D.; Stewart, P. S.; Suci, P. A. (1997) Comparison of recalcitrance to ciprofloxacin and levofloxacin exhibited by *Pseudomonas aeruginosa* biofilms displaying rapid-transport characteristics. *Antimicrob. Agents Chemother.* 41, 1352-1358. 10.1128/AAC.41.6.1352

50. Nation, R. L.; Li, J. (2009) Colistin in the 21st century. *Curr. Opin. Infect. Dis.* 22, 535-543. 10.1097/QCO.0b013e328332e672

51. Li, J.; Nation, R. L.; Turnidge, J. D.; Milne, R. W.; Coulthard, K.; Rayner, C. R.; Paterson, D. L. (2006) Colistin: the re-emerging antibiotic for multi drug-resistant Gram-negative bacterial infections. *Lancet Infect. Dis.* 6, 589-601. 10.1016/S1473-3099(06)70580-1

52. Ezadi, F.; Ardebili, A.; Mirnejad, R. (2019) Antimicrobial Susceptibility Testing for Polymyxins: Challenges, Issues, and Recommendations. *J. Clin. Microbiol.* 57, pages or article number. 10.1128/JCM.01390-18

53. Hoiby, N.; Bjarnsholt, T.; Givskov, M.; Molin, S.; Ciofu, O. (2010) Antibiotic resistance of bacterial biofilms. *Int. J. Antimicrob. Agents* 35, 322-332. 10.1016/j.ijantimicag.2009.12.011

54. Heydorn, A.; Nielsen, A. T.; Hentzer, M.; Sternberg, C.; Givskov, M.; Ersboll, B. K.; Molin, S. (2000) Quantification of biofilm structures by the novel computer program COMSTAT. *Microbiology* 146 (Pt 10), 2395-2407. 10.1099/00221287-146-10-2395

55. Goss, C. H.; Kaneko, Y.; Khuu, L.; Anderson, G. D.; Ravishankar, S.; Aitken, M. L.; Lechtzin, N.; Zhou, G.; Czyz, D. M.; McLean, K.; Olakanmi, O.; Shuman, H. A.; Teresi, M.; Wilhelm, E.; Caldwell, E.; Salipante, S. J.; Hornick, D. B.; Siehnel, R. J.; Becker, L.; Britigan, B. E.; Singh, P. K. (2018) Gallium disrupts bacterial iron metabolism and has therapeutic effects in mice and humans with lung infections. *Sci. Transl. Med* pages or article number. 10, 10.1126/scitranslmed.aat7520

56. Yamamoto, K.; Arai, H.; Ishii, M.; Igarashi, Y. (2011) Trade-off between oxygen and iron acquisition in bacterial cells at the air-liquid interface. *FEMS Microbiol. Ecol.* 77, 83-94. 10.1111/j.1574-6941.2011.01087.x 57. Friedman, L.; Kolter, R. (2004) Genes involved in matrix formation in *Pseudomonas aeruginosa* PA14 biofilms. *Mol. Microbiol.* 51, 675-690. 10.1046/j.1365-2958.2003.03877.x 58. Oliver, J. D. (2010) Recent findings on the viable but nonculturable state in pathogenic bacteria. *FEMS Microbiol. Rev* 34, 415-425. 10.1111/j.1574-6976.2009.00200.x 59. Ayrapetyan, M.; Williams, T. C.; Oliver, J. D. (2015) Bridging the gap between viable but non-culturable and antibiotic persistent bacteria. *Trends Microbiol.* 23, 7-13. 10.1016/j.tim.2014.09.004

60. Marques, C. N.; Salisbury, V. C.; Greenman, J.; Bowker, K. E.; Nelson, S. M. (2005) Discrepancy between viable counts and light output as viability measurements, following ciprofloxacin challenge of self-bioluminescent *Pseudomonas aeruginosa* biofilms. *J. Antimicrob. Chemother.* 56, 665-671. 10.1093/jac/dki285

61. Marques, C. N. H.; Nelson, S. M. (2019) Pharmacodynamics of ciprofloxacin against *Pseudomonas aeruginosa*

61. planktonic and biofilm-derived cells. *Lett. Appl. Microbiol.* 68, 350-359. 10.1111/1 am.13126
62. Johnson, M.; Zaretskaya, I.; Raytselis, Y.; Merezhuk, Y.; McGinnis, S.; Madden, T. L. (2008) NCBIBLAST: abetter web interface. *Nucleic Acids Res.* 36, W5-9. 10.1093/nar/gkn201
63. Winsor, G. L.; Griffiths, E. J.; Lo, R.; Dhillon, B. K.; Shay, J. A.; Brinkman, F. S. (2016) Enhanced annotations and features for comparing thousands of *Pseudomonas* genomes in the *Pseudomonas* genome database. *Nucleic Acids Res.* 44, D646-653. 10.1093/nar/gkv1227
64. Haagensen, J. A.; Klausen, M.; Ernst, R. K.; Miller, S. I.; Folkesson, A.; Tolker-Nielsen, T.; Molin, S. (2007) Differentiation and distribution of colistin- and sodium dodecyl sulfate-tolerant cells in *Pseudomonas aeruginosa* biofilms. *J. Bacteriol.* 189, 28-37. 10.1128/JB.00720-06
65. Kolpen, M.; Appeldorff, C. F.; Brandt, S.; Mousavi, N.; Kragh, K. N.; Aydogan, S.; Uppal, H. A.; Bjamsholt, T.; Ciofu, O.; Hoiby, N.; Jensen, P. O. (2016) Increased bactericidal activity of colistin on *Pseudomonas aeruginosa* biofilms in anaerobic conditions. Pathog. Dis. 74, ftv086. 10.1093/femspd/ftv086
66. Mettrick, K.; Hassan, K.; Lamont, I.; Reid, D. (2020) The Iron-chelator, N,N'-bis (2-hydroxybenzyl) Ethylenediamine-N,N'-Diacetic acid is an Effective Colistin Adjunct against Clinical Strains of Biofilm-Dwelling *Pseudomonas aeruginosa*. *Antibiotics (Basel)* 9, pages or article number. 10.3390/antibiotics9040144
67. Moreau-Marquis, S.; O'Toole, G. A.; Stanton, B. A. (2009) Tobramycin and FDA-approved iron chelators eliminate *Pseudomonas aeruginosa* biofilms on cystic fibrosis cells. *Am. J. Respir. Cell Mol Biol* 41, 305-13. 10.1165/rcmb.2008-0299OC
68. Lora-Tamayo, J.; Murillo, O.; J., A. (2019) Clinical Use of Colisting in Biofilm-Associated Infections. In *Polymyxin Antibiotics; From Laboratory Bench to Bedside. Advances in Experimental Medicine and Biology*, Li, J.; Nation, R. L.; Kaye, K., Eds. Springer, Cham: 2019; Vol. 1145, pp 181-195.
69. Li, J. (2019) Reviving Polymyxins: Achievements, Lessons and the Road Ahead. In *Polymyxin Antibiotics; From Laboratory Bench to Bedside. Advances in Experimental Medicine and Biology*, Li, J.; Nation, R.; Kaye, K., Eds. Springer, Cham: 2019; Vol. 1145, pp 1-page.
70. Madeira, F.; Park, Y. M.; Lee, J.; Buso, N.; Gur, T.; Madhusoodanan, N.; Basutkar, P.; Tivey, A. R. N.; Potter, S. C.; Finn, R. D.; Lopez, R. (2019) The EMBL-EBI search and sequence analysis tools APIs in 2019. *Nucleic Acids Res.* 47, W636-W641. 10.1093/nar/gkz268
71. Ji, C.; Miller, P. A.; Miller, M. J. (2012) Iron transport-mediated drug delivery: practical syntheses and in vitro antibacterial studies of tris-catecholate siderophore-aminopenicillin conjugates reveals selectively potent antipseudomonal activity. *J. Am. Chem. Soc.* 134, 9898-9901. 10.1021/ja303446w
72. Liu, R.; Miller, P. A.; Vakulenko, S. B.; Stewart, N. K.; Boggess, W. C.; Miller, M. J. (2018) A Synthetic Dual Drug Sideromycin Induces Gram-Negative Bacteria To Commit Suicide with a Gram-Positive Antibiotic. *J. Med. Chem.* 61, 3845-3854. 10.1021/acs.jmedchem.8b00218
73. O'May, C. Y.; Sanderson, K.; Roddam, L. F.; Kirov, S. M.; Reid, D. W. (2009) Iron-binding compounds impair *Pseudomonas aeruginosa* biofilm formation, especially under anaerobic conditions. *J. Med. Microbiol.* 58, 765-773. DOL 10.1099/jmm.0.004416-0
74. Windus, D. W.; Stokes, T. J.; Julian, B. A.; Fenves, A. Z. (1987) Fatal *Rhizopus* Infections in Hemodialysis Patients Receiving Deferoxamine. *Ann. Intern. Med.* 107, 678-680. 10.7326/0003-4819-107-5-678
75. Visca, P.; Bonchi, C.; Minandri, F.; Frangipani, E.; Imperi, F. (2013) The dual personality of iron chelators: growth inhibitors or promoters? *Antimicrob. Agents Chemother.* 57, 2432-2433. 10.1128/AAC.02529-12
76. Heinzl, G. A.; Huang, W.; Yu, W.; Giardina, B. J.; Zhou, Y.; MacKerell, A. D., Jr.; Wilks, A.; Xue, F. (2016) Iminoguanidines as Allosteric Inhibitors of the Iron-Regulated Heme Oxygenase (HemO) of *Pseudomonas aeruginosa*. *J. Med. Chem.* 59, 6929-6942. 10.1021/acs.jmedchem.6b00757
77. Centola, G.; Deredge, D. J.; Horn, K.; Ai, Y.; Dent, A. T.; Xue, F.; Wilks, A. (2020) Gallium(III)-Salophen as a Dual Inhibitor of *Pseudomonas aeruginosa* Heme Sensing and Iron Acquisition. *ACS Infect. Dis.* 6, 2073-2085. 10.1021/acsinfecdis.0c00138
78. Kaneko, Y.; Thoendel, M.; Olakanmi, O.; Britigan, B. E.; Singh, P. K. (2007) The Transition Metal Gallium Disrupts *Pseudomonas aeruginosa* Iron Metabolism and has Antimicrobial and Antibiofilm Activity. *J. Clin. Invest.* 117, 877-887. 10.1172/JCI30783
79. Minandri, F.; Bonchi, C.; Frangipani, E.; Imperi, F.; Visca, P. (2014) Promises and failures of gallium as an antibacterial agent. *Future Microbiol.* 9, 379-397. 10.2217/fmb.14.3
80. Stover, C. K.; Pham, X. Q.; Erwin, A. L.; Mizoguchi, S. D.; Warrener, P.; Hickey, M. J.; Brinkman, F. S. L.; Hufnagle, W. O.; Kowalik, D. J.; Lagrou, M.; Garber, R. L.; Goltry, L.; Tolentino, E.; Westbrock-Wadman, S.; Yuan, Y.; Brody, L. L.; Coulter, S. N.; Folger, K. R.; Kas, A.; Larbig, K.; Lim, R.; Simith, K.; Spencer, D.; Wong, G. K. S.; Wu, Z.; Paulsen, I. T.; Reizer, J.; Saler, M. H.; Hancock, R. E. W.; Lory, S.; Olson, M. V. (2000) Complete Genome Sequence of *Pseudomonas aeruginosa* PA01, an Opportunistic Pathogen. *Nature* 406, 959-964. 10.1038/35023079
81. Clark, J.; Maaloe, O. (1967) DNA Replication and the Division Cycle in *Escherichia coli*. *J. Mol. Biol.* 23, 99-112. 10.1016/S0022-2836(67)80070-6
82. Andrews, J. M. (2001) Determination of Minimum Inhibitory Concentrations. *J. Antimicrob. Chemother.* 48 Suppl. 1, 5-16. 10.1093/jac/48.suppl_1.5
83. Sebaugh, J. L. (2011) Guidelines for accurate EC50/IC50 estimation. *Pharm. Stat.* 10, 128-134. 10.1002/pst.426
84. Tawakoli, P. N.; Al-Ahmad, A.; Hoth-Hannig, W.; Hannig, M.; Hannig, C. (2013) Comparison of different live/dead stainings for detection and quantification of adherent microorganisms in the initial oral biofilm. *Clin. Oral Investig.* 17, 841-850. 10.1007/s00784-012-0792-3
85. Otsu, N. (1979) A Threshold Selection Method for Gray-Level Histograms. *IEEE Transactions on Systems, Map and Cybernetics* 9, 62-66.
86. Weinberg, E. D. (2009) Iron Availability and Infection. *Biochim. et Biophys. Acta* 1790, 600-605. 10.1016/j.bbagen.2008.07.002
87. Hennessy, D. J.; Reid, G. R.; Smith, F. E.; Thompson, S. L. (1984) Ferene—a new spectrophotometric reagent for iron. *Can. J. Chem.* 62, 721-724. 10.1139/v84-121
88. Ciccone, L.; Vera, L.; Tepshi, L.; Rosalia, L.; Rossello, A.; Stura, E. A. (2015) Multicomponent mixtures for cryoprotection and ligand solubilization. *Biotechnol. Rep. (Amst)* 7, 120-127. 10.1016/j.btre.2015.05.008
89. Kabsch, W. (1988) Automatic Indexing of Rotation Diffraction Patterns. *J. Appl. Cryst.* 21, 67-72. 10.1107/S002188988700937

90. Vonrhein, C.; Flensburg, C.; Keller, P.; Sharff, A.; Smart, O.; Paciorek, W.; Womack, T.; Bricogne, G. (2011) Data Processing and Analysis with the AutoPROC Toolbox. *Acta Cryst. D Biol Cryst.* D67, 293-302. 10.1107/S0907444911007773

91. Evans, P. R. (2011) An Introduction to Data Reduction: Space-Group Determination, scaling and intentisy statistics. *Acta Cryst.* D67, 282-292. 10.1107/S090744491003982X 92. McCoy, A. J.; Grosse-Kunstleve, R. W.; Adams, P. D.; Winn, M. D.; Storoni, L. C.; Read, R. J. (2007) Phaser crystallographic software. *J. Appl. Cryst.* 40, 658-674. 10.1107/S0021889807021206

93. Adams, P. D.; Afonine, P. V.; Brunkozci, G.; Chen, V. B.; Davis, I. W.; Echols, N.; Headd, J. J.; Hung, L.-W.; Kapral, G. J.; Grosse-Kunstleve, R. W.; McCoy, A. J.; Moriarty, N. W.; Oeffner, R.; Read, R. J.; Richardson, D. C.; Richardson, J. S.; Terwilliger, T. C.; Zwart, P. H. (2010) PHENIX: A Comprehensive Python-Based System for Macromolecular Structure Solution. *Acta Cryst.* D66, 213-221. 10.1107/S0907444909052925

94. Emsley, P.; Lohkamp, B.; Scott, W. G.; Cowan, K. (2010) Features and Development of Coot. *Acta Cryst.* D66, 486-501. 10.1107/S0907444910007493

95. Chen, V. B.; Arendall, W. B. r.; Headd, J. J.; Keedy, D. A.; Immormino, R. M.; Kapral, G. J.; Murray, L. W.; Richardson, J. S.; Richardson, D. C. (2010) MolProbity: All-Atom Structure Validation for Macromolecular Crystallography. *Acta Cryst. D* 66, 12-21. 10.1107/S0907444909042073

96. CDC. Antibiotic Resistance Threats in the United States 2013. www.cdc.gov/drugresistance/threat-report-2013/.

97. Blaskovich, M. A.; Butler, M. S.; Cooper, M. A., Polishing the tarnished silver bullet: the quest for new antibiotics. *Essays Biochem.* 2017, 61 (1), 103-114.

98. Laxminarayan, R.; Duse, A.; Wattal, C.; Zaidi, A. K.; Wertheim, H. F.; Sumpradit, N.; Vlieghe, E.; Hara, G. L.; Gould, I. M.; Goossens, H.; Greko, C.; So, A. D.; Bigdeli, M.; Tomson, G.; Woodhouse, W.; Ombaka, E.; Peralta, A. Q.; Qamar, F. N.; Mir, F.; Kariuki, S.; Bhutta, Z. A.; Coates, A.; Bergstrom, R.; Wright, G. D.; Brown, E. D.; Cars, O., Antibiotic resistance—the need for global solutions. *Lancet Infect. Dis.* 2013, 13 (12), 1057-1098.

99. Ballouche, M.; Cornelis, P.; Baysse, C., Iron Metabolism: A Promising Target for Antibacterial strategies. *Recent Patents on Anti-Infective Drug Discovery* 2009, 4, 190-205.

100. Foley, T. L.; Simeonov, A., Targeting iron assimilation to develop new antibacterials. *Expert Opin. Drug Discov.* 2012, 7 (9), 831-847.

101. Cornelis, P.; Wei, Q.; Andrews, S. C.; Vinckx, T., Iron homeostasis and management of oxidative stress response in bacteria. *Metallomics* 2011, 3 (6), 540-9.

102. Hood, M. I.; Skaar, E. P., Nutritional immunity: transition metals at the pathogen-host interface. *Nat. Rev. Microbiol.* 2012, 10 (8), 525-537.

103. Benson, D. R.; Rivera, M., Heme Uptake and Metabolism in Bacteria. *Met. Ions Life Sci.* 2013, 12, 279-332.

104. Rivera, M., Bacterioferritin: Structure Function and Protein-Protein Interactions. In *Handbook of Porphyrin Science*, Kadish, K. K.; Smith, K. M.; Guilard, R., Eds. 2014; Vol. 30, pp 136-179.

105. Andrews, S.; Norton, I.; Salunkhe, A. S.; Goodluck, H.; Aly, W. S.; Mourad-Agha, H.; Cornelis, P., Control of iron metabolism in bacteria. *Met. Ions Life Sci.* 2013, 12, 203-239.

106. Ruvinsky, A. M.; Vakser, I. A.; Rivera, M., Local packing modulates diversity of iron pathways and cooperative behavior in eukaryotic and prokaryotic ferritins. *J. Chem. Phys.* 2014, 140 (11), 115104.

107. Rui, H.; Rivera, M.; Im, W., Protein dynamics and ion traffic in bacterioferritin. *Biochemistry* 2012, 51 (49), 9900-9910.

108. Yao, H.; Rui, H.; Kumar, R.; Eshelman, K.; Lovell, S.; Battaile, K. P.; Im, W.; Rivera, M., Concerted motions networking pores and distant ferroxidase centers enable bacterioferritin function and iron traffic. *Biochemistry* 2015, 54 (8), 1611-1627.

109. Ma, J.-F.; Ochsner, U. A.; Klotz, M. G.; Nanayakkara, V. K.; Howell, M. L.; Johnson, Z.; Posey, J. E.; Vasil, M. L.; Monaco, J. J.; Hassett, D. J., Bacterioferritin A Modulates Catalase A (KatA) Activity and Resistance to Hydrogen Peroxide in *Pseudomonas aeruginosa*. *J. Bacteriol.* 1999, 757, 3730-3742.

110. Wang, Y.; Yao, H.; Cheng, Y.; Lovell, S.; Battaile, K. P.; Middaugh, C. R.; Rivera, M., Characterization of the Bacterioferritin/Bacterioferritin Associated Ferredoxin Protein-Protein Interactions in Solution and Determination of Binding Energy Hot Spots. *Biochemistry* 2015, 54, 6162-6175.

111. Spring, D. R., Chemical genetics to chemical genomics: small molecules offer big insights. *Chem. Soc. Rev* 2005, 34 (6), 472-482.

112. O'Connor, C. J.; Laraia, L.; Spring, D. R., Chemical genetics. *Chem. Soc. Rev.* 2011, 40 (8), 4332-4345.

113. Koenig, S. M.; Truwit, J. D. Ventilator-Associated Pneumonia: Diagnosis, Treatment, and Prevention. *Clin. Microbio. Rev.,* 2006, 19, 637-657.

114. Koulenti, D.; Lisboa, T.; Brun-Buisson, C.; Krueger, W.; Macor, A.; Sole-Violan, J.; Diaz, E.; Topeli, A.; DeWaele, A.; Carneiro, A.; Martin-Loeches, I.; Armaganidis, A.; Rello, J. Spectrum of practice in the diagnosis of nosocomial pneumonia in patients requiring mechanical ventilation in European intensive care units. *Crit. Care Med.,* 2009, 37, 2360-2368.

115. "Hunting the Nightmare Bacteria." *Frontline*. PBS. Season 2, episode 13. Television.

116. GlobalData, Healthcare-Associated Gram-Negative market to be worth $3.6 billion by 2026, Press Release, Sep. 20, 2017; <https://www.globaldata.com/healthcare-associated-gram-negative-market-to-be-worth-3-6-billion-by-2026/>.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following claims.

The invention claimed is:

1. A method of inhibiting biofilm formation, treating bacteria within a biofilm, or remediating a biofilm in or on a subject, the method comprising administering to the subject an effective amount of a compound according to Formula I

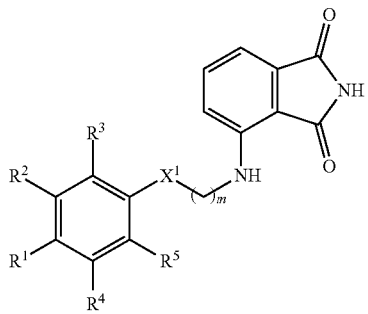

or a pharmaceutically acceptable salt and/or a solvate thereof, wherein
$R^1$ is $C_1$-$C_6$ alkoxy, H, OH, or halo;
$R^2$ and $R^3$ are each independently $C_1$-$C_6$ alkoxy, H, or OH;
$R^4$ and $R^5$ are each independently H or halo;
$X^1$ is $CH_2$ or O; and
m is 0, 1, 2, 3, 4, or 5;
provided that:
  at least one of $R^1$, $R^2$, and $R^3$ is OH or $C_1$-$C_6$ alkoxy;
  when $X^1$ is O, m is not 0; and
  when $R^2$ is OH, $R^1$, $R^3$, $R^4$, and $R^5$ are each independently H, and $X^1$ is $CH_2$, then m is not 0; and
  wherein the subject is suffering from or at risk of suffering from a bacterial infection.

2. The method of claim 1, wherein the method comprises administering to the subject a pharmaceutical composition, wherein the pharmaceutical composition comprises a compound of Formula I and a pharmaceutically acceptable carrier.

3. The method of claim 2, wherein the pharmaceutical composition is formulated for topical administration.

4. The method of claim 1, the method further comprising administering an effective amount of fluoroquinolone antibiotic to the subject, administering an effective amount of aminoglycoside antibiotic to the subject, and/or administering an effective amount of polymyxin antibiotic to the subject.

5. The method of claim 1, wherein the bacterial infection comprises a Gram-negative bacterial infection.

6. The method of claim 1, wherein the bacterial infection comprises a *Pseudomonas aeruginosa* infection, an *Acinetobacter baumannii* infection, a *Klebsiella pneumonia* infection, a *Yersinia pestis* infection, a *Shigella dysenteriae* infection, an *Enterobacter* sp. infection, an *Acinetobacter* sp. infection, a *Salmonella typhimurium* infection, a *Serratia* sp. infection, or a combination of any two or more thereof.

7. The method of claim 1, wherein
$R^1$, $R^2$, and $R^3$ are each independently H or OH;
$R^4$ and $R^5$ are each independently H or halo;
$X^1$ is $CH_2$ or O; and
m is 0, 1, 2, 3, 4, or 5;
provided that at least one of $R^1$, $R^2$, and $R^3$ is OH.

8. The method of claim 7, wherein $X^1$ is $CH_2$.

9. The method of claim 1, wherein the compound is of Formula IA

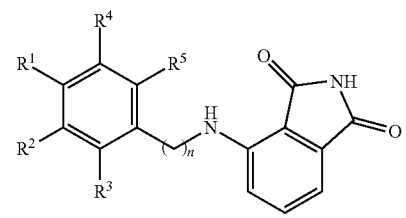

or a pharmaceutically acceptable salt and/or a solvate thereof, wherein n is 1, 2, or 3;
provided that $R^2$ is not OH when n is 1 and $R^1$, $R^3$, $R^4$, and $R^5$ are each independently H.

10. The method of claim 9, wherein one of $R^1$ and $R^3$ is OH, one of $R^1$ and $R^3$ is H, and $R^2$ is H.

11. The method of claim 10, wherein $R^4$ and $R^5$ are each independently H, bromine, chlorine, or fluorine.

12. The method of claim 11, wherein $R^4$ and $R^5$ are each independently H or chlorine.

13. The method of claim 1, wherein the compound is selected from the group consisting of:

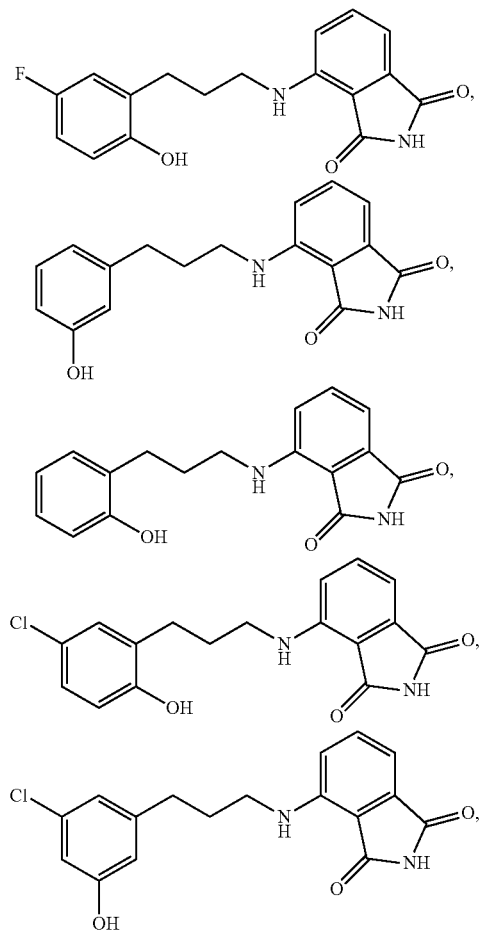

-continued

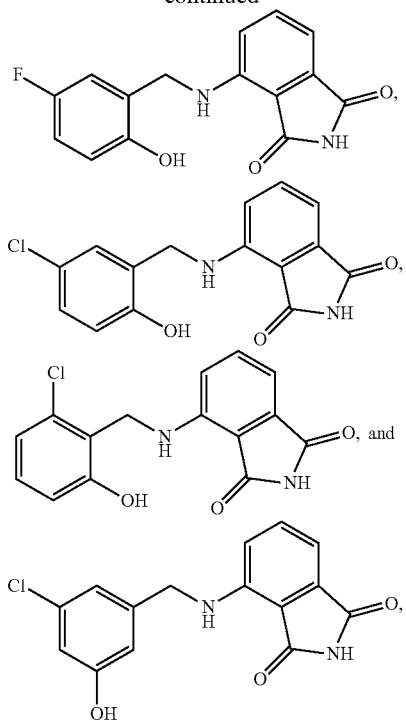

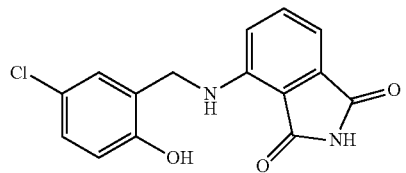 [SMILES: O=C1NC(=O)c2c(NCc3cc(Cl)ccc3O)cccc21]

or a pharmaceutically acceptable salt and/or solvate thereof.

14. The method of claim 13, wherein the compound is

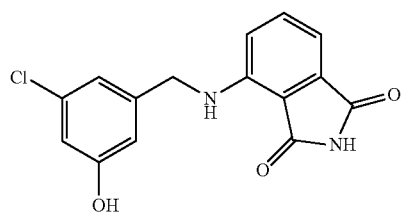 [SMILES: O=C1NC(=O)c2c(NCc3cc(O)cc(Cl)c3)cccc21]

or a pharmaceutically acceptable salt and/or solvate thereof.

15. The method of claim 13, wherein the compound is

16. The method of claim 1, wherein the method inhibits biofilm formation in or on the subject.

17. The method of claim 1, wherein the method treats bacteria within a biofilm in or on the subject.

18. The method of claim 1, wherein the method remediates a biofilm in or on the subject.

19. The method of claim 1, wherein the subject is a human or a surface.

20. The method of claim 1, wherein the compound is selected from the group consisting of:

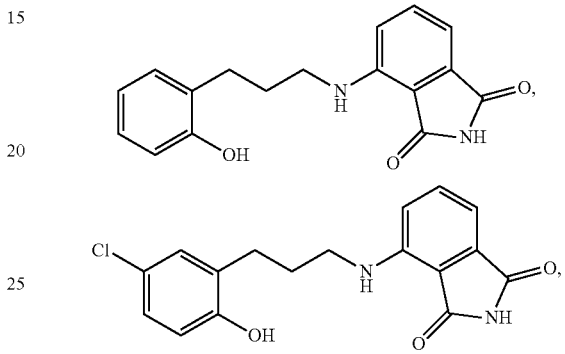

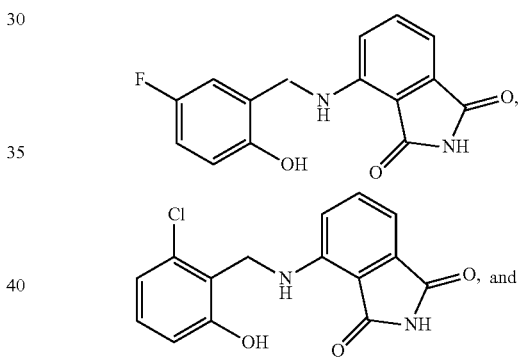

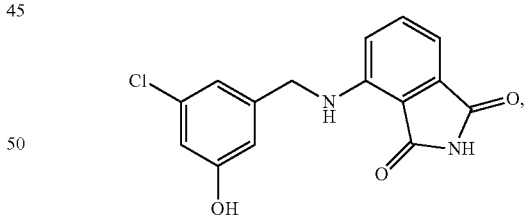

or a pharmaceutically acceptable salt thereof.

* * * * *

SEQUENCE LISTING

```
<160> NUMBER OF SEQ ID NOS: 33

<210> SEQ ID NO 1
<211> LENGTH: 158
<212> TYPE: PRT
<213> ORGANISM: Pseudomonas aeruginosa

<400> SEQUENCE: 1

Met Lys Gly Asp Lys Lys Val Ile Gln His Leu Asn Lys Ile Leu Gly
1               5                   10                  15

Asn Glu Leu Ile Ala Ile Asn Gln Tyr Phe Leu His Ser Arg Met Trp
            20                  25                  30

Asn Asp Trp Gly Leu Lys Arg Leu Gly Ala His Glu Tyr His Glu Ser
        35                  40                  45

Ile Asp Glu Met Lys His Ala Asp Lys Leu Ile Glu Arg Ile Leu Phe
    50                  55                  60

Leu Glu Gly Leu Pro Asn Leu Gln Asp Leu Gly Lys Leu Leu Ile Gly
65                  70                  75                  80

Glu Asn Thr Gln Glu Met Leu Gln Cys Asp Leu Asn Leu Glu Leu Lys
                85                  90                  95

Ala Thr Lys Asp Leu Arg Glu Ala Ile Val His Cys Glu Gln Val His
            100                 105                 110

Asp Tyr Val Ser Arg Asp Leu Leu Lys Asp Ile Leu Glu Ser Glu Glu
        115                 120                 125

Glu His Ile Asp Tyr Leu Glu Thr Gln Leu Gly Leu Ile Gln Lys Val
    130                 135                 140
```

Gly Leu Glu Asn Tyr Leu Gln Ser His Met His Glu Asp Asp
145                 150                 155

<210> SEQ ID NO 2
<211> LENGTH: 158
<212> TYPE: PRT
<213> ORGANISM: Acinetobacter baumannii

<400> SEQUENCE: 2

Met Lys Gly Asp Lys Val Ile Gln His Leu Asn Lys Ile Leu Gly
1               5                   10                  15

Asn Glu Leu Ile Ala Ile Asn Gln Tyr Phe Leu His Ser Arg Met Trp
            20                  25                  30

Asn Asp Trp Gly Leu Lys Arg Leu Gly Thr His Glu Tyr His Glu Ser
        35                  40                  45

Ile Asp Glu Met Lys His Ala Asp Lys Leu Ile Glu Arg Ile Leu Phe
    50                  55                  60

Leu Glu Gly Leu Pro Asn Leu Gln Asp Leu Gly Lys Leu Leu Ile Gly
65                  70                  75                  80

Glu Asn Thr Gln Glu Met Leu Gln Cys Asp Leu Asn Leu Glu Leu Lys
                85                  90                  95

Ala Thr Lys Asp Leu Arg Glu Ala Ile Val His Cys Glu Gln Val His
                100                 105                 110

Asp Tyr Val Ser Arg Asp Leu Leu Lys Asp Ile Leu Glu Ser Glu Glu
            115                 120                 125

Glu His Ile Asp Tyr Leu Glu Thr Gln Leu Gly Leu Ile Gln Lys Val
        130                 135                 140

Gly Leu Glu Asn Tyr Leu Gln Ser His Met His Glu Asp Asp
145                 150                 155

<210> SEQ ID NO 3
<211> LENGTH: 158
<212> TYPE: PRT
<213> ORGANISM: Acinetobacter baumannii

<400> SEQUENCE: 3

Met Lys Gly Asp Lys Met Ile Ala His Leu Asn Lys Leu Leu Gly
1               5                   10                  15

Asn Glu Leu Val Ala Ile Asn Gln Tyr Phe Leu His Ala Arg Met Phe
            20                  25                  30

Lys Asn Trp Gly Leu Thr Arg Leu Asn Glu Val Glu Tyr His Glu Ser
        35                  40                  45

Ile Asp Glu Met Lys His Ala Asp Lys Tyr Ile Glu Arg Ile Leu Phe
    50                  55                  60

Leu Glu Gly Ile Pro Asn Leu Gln Asp Leu Gly Lys Leu Asn Ile Gly
65                  70                  75                  80

Glu Asp Val Glu Glu Met Leu Ala Ser Asp Leu Lys Leu Glu Leu Asp
                85                  90                  95

Gly Ala Lys Asn Leu Lys Glu Ala Ile Ser Tyr Ala Asp Ser Ile His
                100                 105                 110

Asp Tyr Val Ser Arg Asp Leu Met Ile Glu Ile Leu Ala Asp Glu Glu
            115                 120                 125

Asn His Ile Asp Trp Ile Glu Thr Gln Leu Asp Leu Ile Lys Arg Met
        130                 135                 140

Gly Ile Gln Asn Tyr Thr Gln Ala Gln Ile Ile Glu Glu Glu
145                 150                 155

<210> SEQ ID NO 4
<211> LENGTH: 156
<212> TYPE: PRT
<213> ORGANISM: Acinetobacter baumannii

<400> SEQUENCE: 4

```
Met Lys Gly Asp Thr Lys Val Ile Glu Phe Leu Asn Lys Val Leu Tyr
1               5                   10                  15

Asn Glu Leu Thr Ala Ile Asn Gln Tyr Phe Leu His Ala Lys Met Leu
            20                  25                  30

Lys Asn Trp Gly Ile Lys Glu Leu Ala Glu His Glu Tyr Lys Glu Ser
        35                  40                  45

Ile Asp Glu Met Lys His Ala Asp Met Leu Ala Asp Arg Ile Leu Phe
50                  55                  60

Leu Glu Gly Leu Pro Asn Phe Gln Ala Leu Gly Lys Leu Arg Ile Gly
65                  70                  75                  80

Glu Asn Pro Thr Glu Ile Leu Gln Cys Asp Leu Ser Leu Glu Arg Asp
                85                  90                  95

Gly Val Val Thr Leu Arg Glu Ala Val Ala Tyr Ala Asp Ser Val Gly
            100                 105                 110

Asp Tyr Val Ser Arg Gln Leu Phe Val Lys Ile Leu Asp Ser Glu Glu
        115                 120                 125

Glu His Ile Asp Trp Leu Glu Thr Gln Leu Asp Leu Ile Glu Arg Ile
130                 135                 140

Gly Glu Pro Lys Tyr Leu Leu Ser Lys Leu Glu Glu
145                 150                 155
```

<210> SEQ ID NO 5
<211> LENGTH: 154
<212> TYPE: PRT
<213> ORGANISM: Acinetobacter baumannii

<400> SEQUENCE: 5

```
Met Lys Gly Asn Arg Asn Val Ile Asn Gln Leu Asn Gln Val Leu Tyr
1               5                   10                  15

His His Leu Thr Ala Ile Asn Gln Tyr Phe Leu His Ser Arg Met Phe
            20                  25                  30

Asn Asp Trp Gly Ile Glu Gln Leu Gly Ser Ala Glu Tyr Lys Glu Ser
        35                  40                  45

Ile Arg Gln Met Lys His Ala Asp Lys Ile Ile Glu Arg Ile Leu Phe
50                  55                  60

Leu Glu Gly Leu Pro Asn Leu Gln His Leu Gly Lys Leu Tyr Ile Gly
65                  70                  75                  80

Gln His Thr Glu Glu Val Leu Gln Cys Asp Ile Arg Lys Val Lys Glu
                85                  90                  95

Asn Ile Glu Ala Ile Gln Lys Ala Val Ala Leu Ala Glu Thr Glu Gln
            100                 105                 110

Asp Tyr Val Thr Arg Asp Leu Val Gln Glu Ile Leu Glu Lys Glu Glu
        115                 120                 125

Glu Tyr Trp Asp Trp Leu Asp Thr Gln Ile Asp Leu Ile Gly Ser Val
130                 135                 140

Gly Ile Glu Asn Tyr Ile Gln Ser Gln Met
145                 150
```

<210> SEQ ID NO 6

```
<211> LENGTH: 154
<212> TYPE: PRT
<213> ORGANISM: Acinetobacter baumannii

<400> SEQUENCE: 6

Met Lys Gly Asn Arg Asp Val Ile Asn Gln Leu Asn Gln Val Leu Tyr
1               5                   10                  15

His His Leu Thr Ala Ile Asn Gln Tyr Phe Leu His Ser Arg Met Phe
            20                  25                  30

Asn Asp Trp Gly Ile Glu Gln Leu Gly Ser Ala Glu Tyr Lys Glu Ser
        35                  40                  45

Ile Arg Gln Met Lys His Ala Asp Lys Ile Ile Glu Arg Ile Leu Phe
50                  55                  60

Leu Glu Gly Leu Pro Asn Leu Gln His Leu Gly Lys Leu Tyr Ile Gly
65                  70                  75                  80

Gln His Thr Glu Glu Val Leu Gln Cys Asp Ile Arg Lys Val Lys Glu
                85                  90                  95

Asn Ile Glu Ala Ile Gln Lys Ala Val Ala Leu Ala Glu Thr Glu Gln
            100                 105                 110

Asp Tyr Val Thr Arg Asp Leu Ile Gln Glu Ile Leu Glu Lys Glu Glu
        115                 120                 125

Glu Tyr Trp Asp Trp Leu Asp Thr Gln Ile Asp Leu Ile Gly Ser Val
130                 135                 140

Gly Ile Glu Asn Tyr Ile Gln Ser Gln Met
145                 150

<210> SEQ ID NO 7
<211> LENGTH: 154
<212> TYPE: PRT
<213> ORGANISM: Acinetobacter baumannii

<400> SEQUENCE: 7

Met Lys Gly Asn Arg Asp Val Ile Asn Gln Leu Asn Gln Val Leu Tyr
1               5                   10                  15

His His Leu Thr Ala Ile Asn Gln Tyr Phe Leu His Ser Arg Met Phe
            20                  25                  30

Asn Asp Trp Gly Ile Glu Gln Leu Gly Ser Ala Glu Tyr Lys Glu Ser
        35                  40                  45

Ile Arg Gln Met Lys His Ala Asp Lys Ile Ile Glu Arg Ile Leu Phe
50                  55                  60

Leu Glu Gly Leu Pro Asn Leu Gln His Leu Gly Lys Leu Tyr Ile Gly
65                  70                  75                  80

Gln His Thr Glu Glu Val Leu Gln Cys Asp Ile Arg Lys Val Lys Glu
                85                  90                  95

Asn Ile Glu Ala Ile Gln Lys Ala Val Thr Leu Ala Glu Thr Glu Gln
            100                 105                 110

Asp Tyr Val Thr Arg Asp Leu Val Gln Glu Ile Leu Glu Lys Glu Glu
        115                 120                 125

Glu Tyr Trp Asp Trp Leu Asp Thr Gln Ile Asp Leu Ile Gly Ser Val
130                 135                 140

Gly Ile Glu Asn Tyr Ile Gln Ser Gln Met
145                 150

<210> SEQ ID NO 8
<211> LENGTH: 154
<212> TYPE: PRT
<213> ORGANISM: Acinetobacter baumannii
```

<400> SEQUENCE: 8

```
Met Lys Gly Asn Arg Asp Val Ile Asn Gln Leu Asn Gln Val Leu Tyr
1               5                   10                  15

His His Leu Thr Ala Ile Asn Gln Tyr Phe Leu His Ser Arg Met Phe
            20                  25                  30

Asn Asp Trp Gly Ile Glu Gln Leu Gly Ser Ala Glu Tyr Lys Glu Ser
        35                  40                  45

Ile Arg Gln Met Lys His Ala Asp Lys Ile Ile Glu Arg Ile Leu Phe
    50                  55                  60

Leu Glu Gly Leu Pro Asn Leu Gln His Leu Gly Lys Leu Tyr Ile Gly
65                  70                  75                  80

Gln His Thr Glu Glu Val Leu Gln Cys Asp Ile Arg Lys Val Lys Glu
                85                  90                  95

Asn Ile Glu Ala Ile Gln Lys Ala Val Ala Leu Ala Glu Thr Glu Gln
            100                 105                 110

Asp Tyr Val Thr Arg Asp Leu Val Gln Glu Ile Leu Glu Lys Glu Glu
        115                 120                 125

Glu Tyr Trp Asp Trp Leu Asp Thr Gln Ile Asp Leu Ile Gly Ser Val
    130                 135                 140

Gly Ile Glu Asn Tyr Ile Gln Ser Gln Met
145                 150
```

<210> SEQ ID NO 9
<211> LENGTH: 154
<212> TYPE: PRT
<213> ORGANISM: Acinetobacter baumannii

<400> SEQUENCE: 9

```
Met Lys Gly Asn Arg Asp Val Ile Asn Gln Leu Asn Gln Val Leu Tyr
1               5                   10                  15

His His Leu Thr Ala Ile Asn Gln Tyr Phe Leu His Ser Arg Met Phe
            20                  25                  30

Asn Asp Trp Gly Ile Glu Gln Leu Gly Ser Ala Glu Tyr Lys Glu Ser
        35                  40                  45

Ile Arg Gln Met Lys His Ala Asp Lys Ile Ile Glu Arg Ile Leu Phe
    50                  55                  60

Leu Glu Gly Leu Pro Asn Leu Gln His Leu Gly Lys Leu Tyr Ile Gly
65                  70                  75                  80

Gln His Thr Glu Glu Val Leu Gln Cys Asp Ile Arg Lys Val Lys Glu
                85                  90                  95

Asn Ile Glu Ala Ile Gln Lys Ala Val Ala Leu Ala Glu Thr Glu Gln
            100                 105                 110

Asp Tyr Val Thr Arg Asp Leu Val Gln Glu Ile Leu Glu Lys Glu Glu
        115                 120                 125

Glu Tyr Trp Asp Trp Leu Asp Thr Gln Ile Asp Leu Ile Gly Ser Val
    130                 135                 140

Gly Ile Glu Asn Tyr Ile Gln Ser Arg Met
145                 150
```

<210> SEQ ID NO 10
<211> LENGTH: 154
<212> TYPE: PRT
<213> ORGANISM: Acinetobacter baumannii

<400> SEQUENCE: 10

Met Lys Gly Asn Arg Asp Val Ile Asn Gln Leu Asn Gln Val Leu Tyr
1               5                   10                  15

His His Leu Thr Ala Ile Asn Gln Tyr Phe Leu His Ser Arg Met Phe
            20                  25                  30

Asn Asp Trp Gly Ile Glu Gln Leu Gly Ser Ala Glu Tyr Lys Glu Ser
            35                  40                  45

Ile Arg Gln Met Lys His Ala Asp Lys Ile Ile Glu Arg Ile Leu Phe
    50                  55                  60

Leu Glu Gly Leu Pro Asn Leu Gln His Leu Gly Lys Leu Tyr Ile Gly
65                  70                  75                  80

Gln His Thr Glu Glu Val Leu Gln Cys Asp Ile Arg Lys Val Lys Glu
                85                  90                  95

Asn Ile Glu Ala Ile Gln Lys Ala Val Ala Leu Ala Glu Ala Glu Gln
                100                 105                 110

Asp Tyr Val Thr Arg Asp Leu Val Gln Glu Ile Leu Glu Lys Glu Glu
            115                 120                 125

Glu Tyr Trp Asp Trp Leu Asp Thr Gln Ile Asp Leu Ile Gly Ser Val
            130                 135                 140

Gly Ile Glu Asn Tyr Ile Gln Ser Gln Met
145                 150

<210> SEQ ID NO 11
<211> LENGTH: 157
<212> TYPE: PRT
<213> ORGANISM: Klebsiella pneumoniae

<400> SEQUENCE: 11

Met Lys Gly Asp Lys Lys Met Ile Ala His Leu Asn Lys Leu Leu Gly
1               5                   10                  15

Gly Glu Leu Val Ala Ile Asn Gln Tyr Phe Leu His Ala Arg Met Phe
            20                  25                  30

Lys Asn Trp Gly Phe Thr Arg Leu Asn Ala Met Glu Tyr His Glu Ser
            35                  40                  45

Ile Asp Glu Met Lys His Ala Asp Lys Tyr Ile Glu Arg Ile Leu Phe
    50                  55                  60

Leu Glu Gly Ile Pro Asn Leu Gln Asp Leu Gly Lys Leu Asn Ile Gly
65                  70                  75                  80

Glu Asp Val Glu Glu Met Leu Arg Ser Asp Leu Glu Leu Glu Leu Gly
                85                  90                  95

Gly Ala Lys Asp Leu Arg Glu Ala Ile Ala Tyr Ala Asp Ser Ile His
                100                 105                 110

Asp Tyr Val Ser Arg Asp Leu Met Leu Glu Ile Leu Thr Asp Glu Glu
            115                 120                 125

Gly His Ile Asp Trp Ile Glu Thr Gln Leu Glu Leu Ile Glu Arg Ile
            130                 135                 140

Gly Leu Gln Asn Tyr Leu Gln Ala Gln Met Ile Glu Glu
145                 150                 155

<210> SEQ ID NO 12
<211> LENGTH: 158
<212> TYPE: PRT
<213> ORGANISM: Klebsiella pneumoniae

<400> SEQUENCE: 12

Met Lys Gly Asp Thr Lys Val Ile Asn Tyr Leu Asn Lys Leu Leu Gly
1               5                   10                  15

```
Asn Glu Leu Val Ala Ile Asn Gln Tyr Phe Leu His Ala Arg Met Phe
            20                  25                  30

Lys Asn Trp Gly Leu Lys Arg Leu Asn Asp Val Glu Tyr His Glu Ser
        35                  40                  45

Ile Asp Glu Met Lys His Ala Asp Arg Tyr Ile Glu Arg Ile Leu Phe
    50                  55                  60

Leu Glu Gly Leu Pro Asn Leu Gln Asp Leu Gly Lys Leu Asn Ile Gly
 65                 70                  75                  80

Glu Asp Val Glu Glu Met Leu Arg Ser Asp Leu Ala Leu Glu Leu Asp
                85                  90                  95

Gly Ala Lys Asn Leu Arg Glu Ala Ile Gly Tyr Ala Asp Ser Val His
                100                 105                 110

Asp Tyr Val Ser Arg Asp Met Met Ile Glu Ile Leu Arg Asp Glu Glu
            115                 120                 125

Gly His Ile Asp Trp Leu Glu Thr Glu Leu Asp Leu Ile Gln Lys Met
130                 135                 140

Gly Leu Gln Asn Tyr Leu Gln Ala Gln Ile Arg Glu Glu Gly
145                 150                 155

<210> SEQ ID NO 13
<211> LENGTH: 158
<212> TYPE: PRT
<213> ORGANISM: Klebsiella pneumoniae

<400> SEQUENCE: 13

Met Lys Gly Asp Val Lys Ile Ile Asn Tyr Leu Asn Lys Leu Leu Gly
 1               5                  10                  15

Asn Glu Leu Val Ala Ile Asn Gln Tyr Phe Leu His Ala Arg Met Phe
            20                  25                  30

Lys Asn Trp Gly Leu Met Arg Leu Asn Asp Val Glu Tyr His Glu Ser
        35                  40                  45

Ile Asp Glu Met Lys His Ala Asp Lys Tyr Ile Glu Arg Ile Leu Phe
    50                  55                  60

Leu Glu Gly Ile Pro Asn Leu Gln Asp Leu Gly Lys Leu Gly Ile Gly
 65                 70                  75                  80

Glu Asp Val Glu Glu Met Leu Gln Ser Asp Leu Arg Leu Glu Leu Glu
                85                  90                  95

Gly Ala Lys Asp Leu Arg Glu Ala Ile Ala Tyr Ala Asp Ser Val His
                100                 105                 110

Asp Tyr Val Ser Arg Asp Met Met Ile Glu Ile Leu Ala Asp Glu Glu
            115                 120                 125

Gly His Ile Asp Trp Leu Glu Thr Glu Leu Asp Leu Ile Gly Lys Ile
130                 135                 140

Gly Leu Gln Asn Tyr Leu Gln Ser Gln Ile Lys Val Lys Asp
145                 150                 155

<210> SEQ ID NO 14
<211> LENGTH: 158
<212> TYPE: PRT
<213> ORGANISM: Klebsiella pneumoniae

<400> SEQUENCE: 14

Met Lys Gly Asp Val Lys Ile Ile Ser Tyr Leu Asn Lys Leu Leu Gly
 1               5                  10                  15

Asn Glu Leu Val Ala Ile Asn Gln Tyr Phe Leu His Ala Arg Met Phe
            20                  25                  30
```

```
Lys Asn Trp Gly Leu Met Arg Leu Asn Asp Ile Glu Tyr His Glu Ser
            35                  40                  45

Ile Asp Glu Met Lys His Ala Asp Lys Tyr Ile Glu Arg Ile Leu Phe
 50                      55                  60

Leu Glu Gly Ile Pro Asn Leu Gln Asp Leu Gly Lys Leu Gly Ile Gly
 65                  70                  75                  80

Glu Asp Val Glu Glu Met Leu Arg Ser Asp Leu Arg Leu Glu Leu Glu
                85                  90                  95

Gly Ala Gln Asn Leu Arg Glu Ala Ile Ala Tyr Ala Asp Ser Val His
            100                 105                 110

Asp Tyr Val Ser Arg Asp Met Met Ile Glu Ile Leu Glu Asp Glu Glu
            115                 120                 125

Gly His Ile Asp Trp Leu Glu Thr Glu Leu Asp Leu Ile Gly Lys Ile
        130                 135                 140

Gly Leu Gln Asn Tyr Leu Gln Ser Gln Ile Lys Val Ser Asp
145                 150                 155

<210> SEQ ID NO 15
<211> LENGTH: 158
<212> TYPE: PRT
<213> ORGANISM: Klebsiella pneumoniae

<400> SEQUENCE: 15

Met Lys Gly Asp Val Lys Ile Ile Ser Tyr Leu Asn Lys Leu Leu Gly
 1               5                  10                  15

Asn Glu Leu Val Ala Ile Asn Gln Tyr Phe Leu His Ala Arg Met Phe
                20                  25                  30

Lys Asn Trp Gly Leu Met Arg Leu Asn Asp Thr Glu Tyr His Glu Ser
            35                  40                  45

Ile Asp Glu Met Lys His Ala Asp Lys Tyr Ile Glu Arg Ile Leu Phe
 50                      55                  60

Leu Glu Gly Ile Pro Asn Leu Gln Asp Leu Gly Lys Leu Gly Ile Gly
 65                  70                  75                  80

Glu Asp Val Glu Glu Met Leu Arg Ser Asp Leu Arg Leu Glu Leu Glu
                85                  90                  95

Gly Ala Gln Asn Leu Arg Glu Ala Ile Ala Tyr Ala Asp Ser Val His
            100                 105                 110

Asp Tyr Val Ser Arg Asp Met Met Ile Glu Ile Leu Ala Asp Glu Glu
            115                 120                 125

Gly His Ile Asp Trp Leu Glu Thr Glu Leu Asp Leu Ile Gly Lys Ile
        130                 135                 140

Gly Leu Gln Asn Tyr Leu Gln Ser Gln Ile Lys Val Ser Asp
145                 150                 155

<210> SEQ ID NO 16
<211> LENGTH: 158
<212> TYPE: PRT
<213> ORGANISM: Klebsiella pneumoniae

<400> SEQUENCE: 16

Met Lys Gly Asp Val Lys Ile Ile Ser Tyr Leu Asn Lys Leu Leu Gly
 1               5                  10                  15

Asn Glu Leu Val Ala Ile Asn Gln Tyr Phe Leu His Ala Arg Met Phe
                20                  25                  30

Lys Asn Trp Gly Leu Met Arg Leu Asn Asp Ile Glu Tyr His Glu Ser
            35                  40                  45
```

```
Ile Asp Glu Met Lys His Ala Asp Lys Tyr Ile Glu Arg Ile Leu Phe
 50                  55                  60

Leu Glu Gly Ile Pro Asn Leu Gln Asp Leu Gly Lys Leu Ser Ile Gly
 65                  70                  75                  80

Glu Asp Val Glu Glu Met Leu Arg Ser Asp Leu Arg Leu Glu Leu Glu
                 85                  90                  95

Gly Ala Gln Asn Leu Arg Glu Ala Ile Ala Tyr Ala Asp Ser Val His
                100                 105                 110

Asp Tyr Val Ser Arg Asp Met Met Ile Glu Ile Leu Ala Asp Glu Glu
                115                 120                 125

Gly His Ile Asp Trp Leu Glu Thr Glu Leu Asp Leu Ile Gly Lys Ile
            130                 135                 140

Gly Leu Gln Asn Tyr Leu Gln Ser Gln Ile Lys Val Ser Asp
145                 150                 155
```

<210> SEQ ID NO 17
<211> LENGTH: 158
<212> TYPE: PRT
<213> ORGANISM: Klebsiella pneumoniae

<400> SEQUENCE: 17

```
Met Lys Gly Asp Val Lys Ile Ile Ser Tyr Leu Asn Lys Leu Leu Gly
 1               5                  10                  15

Asn Glu Leu Val Ala Ile Asn Gln Tyr Phe Leu His Ala Arg Met Phe
                 20                  25                  30

Lys Asn Trp Gly Leu Met Arg Leu Asn Asp Ile Glu Tyr His Glu Ser
             35                  40                  45

Ile Asp Glu Met Lys His Ala Asp Lys Tyr Ile Glu Arg Ile Leu Phe
 50                  55                  60

Leu Glu Gly Ile Pro Asn Leu Gln Asp Leu Gly Lys Leu Gly Ile Gly
 65                  70                  75                  80

Glu Asp Val Glu Glu Met Leu Arg Ser Asp Leu Arg Leu Glu Leu Glu
                 85                  90                  95

Gly Ala Gln Asn Leu Arg Glu Ala Ile Ala Tyr Ala Asp Arg Val His
                100                 105                 110

Asp Tyr Val Ser Arg Asp Met Met Ile Glu Ile Leu Ala Asp Glu Glu
                115                 120                 125

Gly His Ile Asp Trp Leu Glu Thr Glu Leu Asp Leu Ile Gly Lys Ile
            130                 135                 140

Gly Leu Gln Asn Tyr Leu Gln Ser Gln Ile Lys Val Ser Asp
145                 150                 155
```

<210> SEQ ID NO 18
<211> LENGTH: 158
<212> TYPE: PRT
<213> ORGANISM: Klebsiella pneumoniae

<400> SEQUENCE: 18

```
Met Lys Gly Asp Val Lys Ile Ile Ser Tyr Leu Asn Lys Leu Leu Gly
 1               5                  10                  15

Asn Glu Leu Val Ala Ile Asn Gln Tyr Phe Leu His Ala Arg Met Phe
                 20                  25                  30

Lys Asn Trp Gly Leu Leu Arg Leu Asn Asp Ile Glu Tyr His Glu Ser
             35                  40                  45

Ile Asp Glu Met Lys His Ala Asp Lys Tyr Ile Glu Arg Ile Leu Phe
 50                  55                  60
```

```
Leu Glu Gly Ile Pro Asn Leu Gln Asp Leu Gly Lys Leu Gly Ile Gly
 65                  70                  75                  80

Glu Asp Val Glu Glu Met Leu Arg Ser Asp Leu Arg Leu Glu Leu Glu
                 85                  90                  95

Gly Ala Gln Asn Leu Arg Glu Ala Ile Ala Tyr Ala Asp Ser Val His
            100                 105                 110

Asp Tyr Val Ser Arg Asp Met Met Ile Glu Ile Leu Ala Asp Glu Glu
        115                 120                 125

Gly His Ile Asp Trp Leu Glu Thr Glu Leu Asp Leu Ile Gly Lys Ile
    130                 135                 140

Gly Leu Gln Asn Tyr Leu Gln Ser Gln Ile Lys Val Ser Asp
145                 150                 155

<210> SEQ ID NO 19
<211> LENGTH: 160
<212> TYPE: PRT
<213> ORGANISM: Klebsiella pneumoniae

<400> SEQUENCE: 19

Met Lys Gly Asp Lys Met Ile Ser His Leu Asn Lys Leu Leu Gly
 1               5                  10                  15

Asn Glu Leu Val Ala Ile Asn Gln Tyr Phe Leu His Ala Arg Met Phe
                 20                  25                  30

Lys Asn Trp Gly Leu Ile Lys Leu Asn Asn Lys Glu Tyr Glu Glu Ser
            35                  40                  45

Ile Asp Glu Met Lys His Ala Asp Glu Tyr Ile Glu Arg Ile Leu Phe
        50                  55                  60

Leu Glu Gly Ile Pro Asn Leu Gln Asp Leu Gly Lys Leu His Ile Gly
 65                  70                  75                  80

Glu Asp Val Glu Glu Met Leu Lys Ser Asp Leu Gln Leu Glu Leu Asp
                 85                  90                  95

Gly Ala Lys Asp Leu Arg Glu Ala Ile Ala Tyr Ala Asp Ser Lys His
            100                 105                 110

Asp Tyr Val Ser Arg Asp Leu Met Ile Lys Ile Leu Ala Glu Glu Glu
        115                 120                 125

Ser His Ile Asp Trp Leu Glu Thr Gln Leu Asp Leu Ile Ala Arg Val
    130                 135                 140

Gly Leu Gln Asn Tyr Gln Gln Ala Gln Met Ala Asp Ala Asp Thr Glu
145                 150                 155                 160

<210> SEQ ID NO 20
<211> LENGTH: 158
<212> TYPE: PRT
<213> ORGANISM: Klebsiella pneumoniae
<220> FEATURE:
<221> NAME/KEY: MOD_RES
<222> LOCATION: (88)..(88)
<223> OTHER INFORMATION: Any amino acid

<400> SEQUENCE: 20

Met Lys Gly Asp Val Lys Ile Ile Ser Tyr Leu Asn Lys Leu Leu Gly
 1               5                  10                  15

Asn Glu Leu Val Ala Ile Asn Gln Tyr Phe Leu His Ala Arg Met Phe
                 20                  25                  30

Lys Asn Trp Gly Leu Met Arg Leu Asn Asp Ile Glu Tyr His Glu Ser
            35                  40                  45

Ile Asp Glu Met Lys His Ala Asp Lys Tyr Ile Glu Arg Ile Leu Phe
        50                  55                  60
```

```
Leu Glu Gly Ile Pro Asn Leu Gln Asp Leu Gly Lys Leu Gly Ile Gly
 65                  70                  75                  80

Glu Asp Val Glu Met Leu Xaa Ser Asp Leu Arg Leu Glu Leu Glu
                 85                  90                  95

Gly Ala Gln Asn Leu Arg Glu Ala Ile Ala Tyr Ala Asp Ser Val His
            100                 105                 110

Asp Tyr Val Ser Arg Asp Met Met Ile Glu Ile Leu Ala Asp Glu Glu
        115                 120                 125

Gly His Ile Asp Trp Leu Glu Thr Glu Leu Asp Leu Ile Gly Lys Ile
130                 135                 140

Gly Leu Gln Asn Tyr Leu Gln Ser Gln Ile Lys Val Ser Asp
145                 150                 155

<210> SEQ ID NO 21
<211> LENGTH: 73
<212> TYPE: PRT
<213> ORGANISM: Pseudomonas aeruginosa

<400> SEQUENCE: 21

Met Tyr Val Cys Leu Cys Gln Gly Val Thr Asp Asn Gln Ile Arg Asp
  1               5                  10                  15

Ala Ile Tyr Glu Gly Cys Cys Ser Tyr Arg Glu Val Arg Glu Ala Thr
             20                  25                  30

Gly Val Gly Thr Gln Cys Gly Lys Cys Ala Cys Leu Ala Lys Gln Val
         35                  40                  45

Val Arg Glu Thr Leu Asn Asp Leu Gln Ser Ala Gln Pro Val Pro Ala
 50                  55                  60

Phe Gly Thr Thr Ala Phe Val Ala Ala
 65                  70

<210> SEQ ID NO 22
<211> LENGTH: 66
<212> TYPE: PRT
<213> ORGANISM: Acinetobacter baumannii

<400> SEQUENCE: 22

Met Tyr Val Cys Leu Cys Glu Ala Val Thr Asp Lys Gln Ile Arg Ser
  1               5                  10                  15

Ala Val Arg Gln Tyr His Val Thr Ser Leu Lys Gly Leu Arg Gln Ile
             20                  25                  30

Leu Pro Val Gly Arg Glu Cys Gly Lys Cys Ile Arg Gln Thr Arg Glu
         35                  40                  45

Ile Leu Asn Asp Glu Leu Ala Leu Ala Glu His Ile Cys Ile Ala Glu
 50                  55                  60

Val Ala
 65

<210> SEQ ID NO 23
<211> LENGTH: 69
<212> TYPE: PRT
<213> ORGANISM: Acinetobacter baumannii

<400> SEQUENCE: 23

Met Tyr Val Cys Ile Cys Asn Gly Val Thr Asp His Gln Ile Arg Glu
  1               5                  10                  15

Ala Ala Ser His Gly Val Ser Thr Val Ala Glu Leu Thr Met Arg Thr
             20                  25                  30
```

```
Gly Cys Gly Ala Thr Cys Gly Ser Cys Leu Asp Met Ala Gly Asp Leu
            35                  40                  45

Leu Ala Lys Ala Arg Ala Thr His Asp Leu Pro Leu Pro Val Leu Gly
 50                  55                  60

Leu Ala Gln Val Ala
 65
```

<210> SEQ ID NO 24
<211> LENGTH: 64
<212> TYPE: PRT
<213> ORGANISM: Acinetobacter baumannii

<400> SEQUENCE: 24

```
Met Tyr Val Cys Leu Cys Arg Gly Ile Thr Asp Gln Asp Ile Lys Asp
 1               5                  10                  15

Ala Ile Glu Asn Gly Ala Glu Ser Tyr Arg Glu Ile Arg Asp Leu Leu
             20                  25                  30

Asp Leu Gly Thr Cys Cys Gly Arg Cys Ala Pro Glu Ala Arg Ala Ile
            35                  40                  45

Ile Ser Glu Glu Leu Ala Glu Ile Ala Ala Arg Ile Ser Val Ala Ala
 50                  55                  60
```

<210> SEQ ID NO 25
<211> LENGTH: 60
<212> TYPE: PRT
<213> ORGANISM: Acinetobacter baumannii

<400> SEQUENCE: 25

```
Met Cys Arg Gly Ile Thr Asp Gln Asp Ile Lys Asp Ala Ile Glu Asn
 1               5                  10                  15

Gly Ala Glu Ser Tyr Arg Glu Ile Arg Asp Leu Leu Asp Leu Gly Thr
             20                  25                  30

Cys Cys Gly Arg Cys Ala Pro Glu Ala Arg Ala Ile Ile Ser Glu Glu
            35                  40                  45

Leu Ala Glu Ile Ala Ala Arg Ile Ser Val Ala Ala
 50                  55                  60
```

<210> SEQ ID NO 26
<211> LENGTH: 65
<212> TYPE: PRT
<213> ORGANISM: Klebsiella pneumoniae

<400> SEQUENCE: 26

```
Met Tyr Val Cys Leu Cys His Gly Val Ser Asp Lys Lys Ile Ile Ser
 1               5                  10                  15

Thr Val His Lys His Gln Ile Arg Thr Ile Asn Gln Leu Arg Gln Ile
             20                  25                  30

Leu Pro Val Gly Ser Cys Cys Gly Lys Cys Ile Arg Gln Ala Arg Gln
            35                  40                  45

Leu Ile Asp Asp Glu Gln His Leu Leu Tyr Pro Gln Ile Ser Glu Val
            50                  55                  60

Ala
 65
```

<210> SEQ ID NO 27
<211> LENGTH: 64
<212> TYPE: PRT
<213> ORGANISM: Klebsiella pneumoniae

<400> SEQUENCE: 27

```
Met Tyr Val Cys Leu Cys Asn Gly Ile Ser Asp Lys Ile Arg Gln
1               5                   10                  15

Ala Val Arg Gln Phe Ser Pro His Ser Phe Gln Leu Lys Lys Phe
            20                  25                  30

Ile Pro Val Gly Asn Gln Cys Gly Lys Cys Val Arg Ala Ala Arg Glu
            35                  40                  45

Val Met Glu Asp Glu Leu Met Gln Leu Pro Glu Phe Lys Glu Ser Ala
    50                  55                  60
```

<210> SEQ ID NO 28
<211> LENGTH: 64
<212> TYPE: PRT
<213> ORGANISM: Klebsiella pneumoniae

<400> SEQUENCE: 28

```
Met Tyr Val Cys Leu Cys Asn Gly Val Ser Asp Lys Lys Ile Arg Gln
1               5                   10                  15

Ala Val Arg Gln Phe His Pro Gln Ser Phe Gln Leu Arg Lys Phe
            20                  25                  30

Ile Pro Val Gly Asn Gln Cys Gly Lys Cys Ile Arg Ala Ala Arg Glu
            35                  40                  45

Val Met Gln Asp Glu Leu Met Gln Met Pro Glu Phe Lys Glu Ile Ala
    50                  55                  60
```

<210> SEQ ID NO 29
<211> LENGTH: 64
<212> TYPE: PRT
<213> ORGANISM: Klebsiella pneumoniae

<400> SEQUENCE: 29

```
Met Tyr Val Cys Leu Cys Asn Gly Val Ser Asp Lys Lys Ile Arg Gln
1               5                   10                  15

Val Val Arg Gln Phe Gln Pro Gln Ser Phe Gln Gln Leu Arg Lys Phe
            20                  25                  30

Val Pro Val Gly Asn Gln Cys Gly Lys Cys Val Arg Ala Ala Arg Glu
            35                  40                  45

Val Met Glu Asp Glu Leu Thr Thr Met Pro Glu Phe Lys Glu Ile Ala
    50                  55                  60
```

<210> SEQ ID NO 30
<211> LENGTH: 63
<212> TYPE: PRT
<213> ORGANISM: Klebsiella pneumoniae

<400> SEQUENCE: 30

```
Met Tyr Val Cys Leu Cys Asn Ala Ile Ser Asp Lys Ala Ile Arg Asn
1               5                   10                  15

Ala Val Arg Gln Asn Lys Val His Ser Ile Gly Glu Leu Arg Lys Ile
            20                  25                  30

Ile Pro Val Gly Thr Glu Cys Gly Lys Cys Ile Arg His Ala Lys Ala
            35                  40                  45

Val Ile Ala Glu Glu His Met Ser Val Pro Val Asp Arg Val Ala
    50                  55                  60
```

<210> SEQ ID NO 31
<211> LENGTH: 64
<212> TYPE: PRT
<213> ORGANISM: Klebsiella pneumoniae
<220> FEATURE:

```
<221> NAME/KEY: MOD_RES
<222> LOCATION: (9)..(9)
<223> OTHER INFORMATION: Any amino acid

<400> SEQUENCE: 31

Met Tyr Val Cys Leu Cys Asn Gly Xaa Ser Asp Lys Lys Ile Arg Gln
1               5                   10                  15

Val Val Arg Gln Phe Gln Pro Gln Ser Phe Gln Gln Leu Arg Lys Phe
            20                  25                  30

Val Pro Val Gly Asn Gln Cys Gly Lys Cys Val Arg Ala Ala Arg Glu
        35                  40                  45

Val Met Glu Asp Glu Leu Thr Thr Met Pro Gly Phe Lys Glu Ile Ala
    50                  55                  60

<210> SEQ ID NO 32
<211> LENGTH: 158
<212> TYPE: PRT
<213> ORGANISM: Acinetobacter baumannii

<400> SEQUENCE: 32

Met Lys Gly Asp Lys Val Ile Gln His Leu Asn Lys Ile Leu Gly
1               5                   10                  15

Asn Glu Leu Ile Ala Ile Asn Gln Tyr Phe Leu His Ser Arg Met Trp
            20                  25                  30

Asn Asp Trp Gly Leu Lys Arg Leu Gly Ala His Glu Tyr His Glu Ser
        35                  40                  45

Ile Asp Glu Met Lys His Ala Asp Lys Leu Ile Glu Arg Ile Leu Phe
    50                  55                  60

Leu Glu Gly Leu Pro Asn Leu Gln Asp Leu Gly Lys Leu Leu Ile Gly
65                  70                  75                  80

Glu Asn Thr Gln Glu Met Leu Gln Cys Asp Leu Asn Leu Glu Leu Lys
                85                  90                  95

Ala Thr Lys Asp Leu Arg Glu Ala Ile Val His Cys Glu Gln Val His
            100                 105                 110

Asp Tyr Val Ser Arg Asp Leu Leu Lys Asp Ile Leu Glu Ser Glu Glu
        115                 120                 125

Glu His Ile Asp Tyr Leu Glu Thr Gln Leu Gly Leu Ile Gln Lys Val
    130                 135                 140

Gly Leu Glu Asn Tyr Leu Gln Ser His Met His Glu Asp Asp
145                 150                 155

<210> SEQ ID NO 33
<211> LENGTH: 73
<212> TYPE: PRT
<213> ORGANISM: Acinetobacter baumannii

<400> SEQUENCE: 33

Met Tyr Val Cys Leu Cys Gln Gly Val Thr Asp Asn Gln Ile Arg Asp
1               5                   10                  15

Ala Ile Tyr Glu Gly Cys Cys Ser Tyr Arg Glu Val Arg Glu Ala Thr
            20                  25                  30

Gly Val Gly Thr Gln Cys Gly Lys Cys Ala Cys Leu Ala Lys Gln Val
        35                  40                  45

Val Arg Glu Thr Leu Asn Asp Leu Gln Ser Ala Gln Pro Val Pro Ala
    50                  55                  60

Phe Gly Thr Thr Ala Phe Val Ala Ala
65                  70
```